(12) United States Patent
Wildum et al.

(10) Patent No.: US 9,296,720 B2
(45) Date of Patent: Mar. 29, 2016

(54) CARBOXAMIDE-SUBSTITUTED HETEROARYL-PYRAZOLES AND THE USE THEREOF

(71) Applicant: AiCuris GmbH & Co. KG, Wuppertal (DE)

(72) Inventors: Steffen Wildum, Gevelsberg (DE); Burkhard Klenke, Wuppertal (DE); Astrid Wendt, Wuppertal (DE)

(73) Assignee: AICURIS GMBH & CO. KG, Wuppertal (DE)

( * ) Notice: Subject to any disclaimer, the term of this patent is extended or adjusted under 35 U.S.C. 154(b) by 0 days.

(21) Appl. No.: 14/361,126

(22) PCT Filed: Nov. 29, 2012

(86) PCT No.: PCT/EP2012/073944
§ 371 (c)(1),
(2) Date: May 28, 2014

(87) PCT Pub. No.: WO2013/079586
PCT Pub. Date: Jun. 6, 2013

(65) Prior Publication Data
US 2015/0105388 A1    Apr. 16, 2015

(30) Foreign Application Priority Data

Nov. 29, 2011  (DE) .......................... 10 2011 055 815

(51) Int. Cl.
| | | |
|---|---|---|
| *A61K 31/4439* | (2006.01) | |
| *A61K 31/496* | (2006.01) | |
| *A61K 31/5377* | (2006.01) | |
| *C07D 401/04* | (2006.01) | |
| *C07D 401/14* | (2006.01) | |
| *C07D 417/14* | (2006.01) | |
| *A61K 45/06* | (2006.01) | |

(52) U.S. Cl.
CPC .......... *C07D 401/04* (2013.01); *A61K 31/4439* (2013.01); *A61K 31/496* (2013.01); *A61K 31/5377* (2013.01); *A61K 45/06* (2013.01); *C07D 401/14* (2013.01); *C07D 417/14* (2013.01)

(58) Field of Classification Search
CPC ............ A61K 31/4439; A61K 31/496; A61K 31/5377; C07D 401/04; C07D 401/14; C07D 417/14
See application file for complete search history.

(56) References Cited

U.S. PATENT DOCUMENTS

| | | | |
|---|---|---|---|
| 7,622,471 B2 * | 11/2009 | Kanaya et al. ............. | 514/252.1 |
| 8,314,089 B2 | 11/2012 | Schohe-Loop et al. | |
| 8,399,682 B2 | 3/2013 | Thede et al. | |
| 2006/0128685 A1 | 6/2006 | Kanaya et al. | |
| 2011/0124618 A1 | 5/2011 | Thede et al. | |
| 2011/0172207 A1 | 7/2011 | Schohe-Loop et al. | |

FOREIGN PATENT DOCUMENTS

| | | |
|---|---|---|
| DE | 102008015032 A1 | 9/2009 |
| DE | 102008015033 A1 | 9/2009 |
| EP | 1591443 A1 | 11/2005 |

OTHER PUBLICATIONS

International Search Report dated Feb. 14, 2013 issued in corresponding PCT/EP2012/073944 application (pp. 1-4).
Database PubChem [Online] NCBI; (Jun. 22, 2011) XP002690138.
Database PubChem [Online] NCBI; (Jun. 22, 2011) XP002690145.
Database PubChem [Online] NCBI; (Jun. 22, 2011) XP002691369.
Database PubChem [Online] NCBI; (Jun. 22, 2011) XP002691370.
Database PubChem [Online] NCBI; (Jun. 22, 2011) XP002691371.
Database PubChem [Online] NCBI; (Jun. 22, 2011) XP002691372.
Database PubChem [Online] NCBI; (Jun. 22, 2011) XP002691373.
Database PubChem [Online] NCBI; (Jun. 22, 2011) XP002691374.
Database PubChem [Online] NCBI; (Jun. 22, 2011) XP002691375.
Database PubChem [Online] NCBI; (Jun. 22, 2011) XP002691377.
Database PubChem [Online] NCBI; (Jun. 22, 2011) XP002691378.
Database PubChem [Online] NCBI; (Jun. 22, 2011) XP002691379.
Database PubChem [Online] NCBI; (Jun. 22, 2011) XP002691380.
Database PubChem [Online] NCBI; (Jun. 22, 2011) XP002691381.
Database PubChem [Online] NCBI; (Jun. 22, 2011) XP002691410.

* cited by examiner

*Primary Examiner* — Samantha Shterengarts
(74) *Attorney, Agent, or Firm* — Millen White Zelano and Branigan, PC; John Sopp; Anthony Zelano

(57) ABSTRACT

This invention relates to new carboxamide-substituted heteroaryl-pyrazoles, method for their production, their use for the treatment and/or prophylaxis of diseases, as well as their use for the production of pharmaceutical agents for the treatment and/or prophylaxis of diseases, in particular retroviral diseases, in humans and/or animals.

15 Claims, No Drawings

CARBOXAMIDE-SUBSTITUTED HETEROARYL-PYRAZOLES AND THE USE THEREOF

This invention relates to new carboxamide-substituted heteroaryl-pyrazoles, method for their production, their use for treatment and/or prophylaxis of diseases, as well as their use for the production of pharmaceutical agents for treatment and/or prophylaxis of diseases, in particular retroviral diseases, in humans and/or animals.

The human immunodeficiency virus (HIV) causes a chronic-persistent, progressive infection. The disease proceeds over various stages from the asymptomatic infection to the AIDS (Acquired Immunodeficiency Syndrome) clinical picture. AIDS is the final stage of the disease caused by the infection. The long, clinical latency period with persistent viremia, which in the final stage leads to the failure of the immune defense, is characteristic of the HIV/AIDS disease.

By the introduction of the anti-HIV combination therapy, it was possible in the 1990s to effectively slow down the progression of the disease and thus to extend the life expectancy of HIV-infected patients substantially (Palella et al., *N. Engl. J. Med* 1998, 238, 853-860).

The anti-HIV substances currently found on the market inhibit the replication of the HI virus by inhibition of the essential viral enzymes reverse transcriptase (RT), protease or integrase or the entry of HIV into the target cell (Overview in Flexner, *Nature Reviews Drug Discovery* 2007, 6, 959-966). There are two classes of RT inhibitors: nucleosidic and nucleotidic RT inhibitors (NRTI) act by competitive inhibition or chain termination in DNA polymerization. Non-nucleosidic RT inhibitors (NNRTI) bind allosterically to a hydrophobic pocket near the active center of the RT and mediate a change in conformation of the enzyme. The currently available protease inhibitors (PI) block the active center of the viral protease and thus prevent the maturation of merging particles into infectious virions. The single currently allowed integrase inhibitor Raltegravir binds in the active center of the HIV integrase and prevents the integration of the proviral DNA into the host cell genome. Entry inhibitors (fusion inhibitors and co-receptor antagonists) prevent the HIV infection of cells by interaction with the HIV coating protein or by blocking the cellular co-receptors CCR5 or CXCR4.

Since the monotherapy with the temporarily available anti-HIV medications leads to therapy failure by selection-resistant viruses within a short time, a combination therapy with several anti-HIV substances that consist of various classes is usually carried out (highly active antiretroviral therapy=HAART; Carpenter et al., *J. Am. Med. Assoc.* 2000, 283, 381-390).

Despite advances in antiretroviral chemotherapy, more recent studies show that with the available medications, an eradication of HIV and the associated healing of the HIV infection cannot be expected. The latent virus remains in the dormant lymphocytes and represents a reservoir for a reactivation and thus for a renewed propagation of the virus (Finzi et al., *Nature Med.* 1999, 5, 512-517; Lewin et al., J Int AIDS Soc. 2011 Jan. 24; 14:4.). HIV-infected patients must therefore rely on an efficient antiviral therapy for their whole lives. Despite combination therapy, selection-resistant viruses result after some time. Since resistance mutations that are characteristic of each therapeutic class accumulate, the failure of a therapy often means a loss of effectiveness of the entire substance class. This cross-resistance problem is most pronounced in the class of NNRTIs, since here often an individual point mutation in the RT can already be sufficient to produce a loss of effectiveness of all NNRTIs (Overview in Kavlick & Mitsuya, *Antiretroviral Chemotherapy* (Editors De Clercq E.), 2001, ASM Press, 279-312). In most cases, the development of resistances is promoted by the poor compliance of patients, which is caused by an unfavorable profile of side effects and/or complicated metering scheme of the anti-HIV medications.

There is thus an urgent need for new therapeutic options for combating the HIV infection. To this end, a top priority purpose of therapy research relative to HIV is to identify new chemical guide structures that either address a new target in the replication of HIV and/or are effective against the growing number of resistant clinical HIV isolates.

U.S. Pat. No. 5,624,941 and EP 576357 describe pyrazoles as cannabinoid-receptor-antagonists, EP 418845, EP 554829 and WO 04/050632, i.a., for treatment of inflammatory and thrombotic diseases, WO 03/037274 as sodium-ion-channel inhibitors for treatment of pain, WO 06/015860 as adenosine-receptor ligands for treatment of inflammatory and obstructive respiratory diseases, EP 1762568 as inhibitors of platelet aggregation, WO 07/002559 as modulators of the activity of nuclear receptors, WO 07/020388 and WO 05/080343 as cannabinoid-receptor modulators, i.a., for treatment of obesity and psychiatric and neurological disorders, WO 07/009701 and EP 1743637 for treatment of cardiovascular risk factors, DE 10 2004 054 666 for combating harmful plants or for growth regulation of plants.

WO 2011/058149 describes tricyclic pyrazole derivatives as PI3k inhibitors for treatment of autoimmune diseases. WO 2008/074982 describes pyrazole derivatives as CB1-receptor modulators in the treatment of excess weight. Pyrazole derivatives as agents against blood platelet aggregation for treatment of ischemic diseases were described in WO 2004/069824 and WO 2006/004027. Pyrazole derivates as COX-1 inhibitors were described in WO 2004/050632 and US 2004/0116475. WO 2008/017932 describes various arylsulfonamides, also including a pyrazole-containing example, as carbonic anhydrase inhibitors.

DE 10 2008 015 033 and DE 10 2008 015 032 describe phenyl-substituted pyrazoles and their use for treatment and prophylaxis of infections with retroviruses.

One object of this invention is to make available new compounds with the same or improved antiviral action for treatment of viral infectious diseases in humans and animals, which do not have the above-described disadvantages.

Surprisingly enough, it was found that the carboxamide-substituted heteroaryl-pyrazoles described in this invention are effective antivirally.

Compounds of the formula

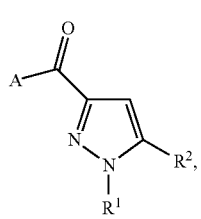

(I)

in which
R¹ stands for phenyl or pyridyl,
whereby phenyl is substituted with 1 to 3, preferably 2, substituents, whereby the substituents are selected independently of one another from the group that consists of halogen, hydroxy, amino, cyano, nitro, ($C_1$-$C_4$)-alkyl, ($C_3$-$C_6$)-cycloalkyl, ($C_1$-$C_4$)-alkylamino and ($C_1$-$C_4$)-alkoxy,
in which
alkyl, cycloalkyl, alkylamino and alkoxy, for their part, can be substituted in one to three places, in the same way or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl, and 4- to 7-membered heterocyclyl, and
whereby pyridyl can be substituted with 1 or 2 substituents, whereby the substituents, independently of one another, are selected from the group that consists of halogen, hydroxy, amino, cyano, nitro, ($C_1$-$C_4$)-alkyl, ($C_3$-$C_6$)-cycloalkyl, and ($C_1$-$C_4$)-alkoxy, and whereby the nitrogen atom of the pyridyl can form an N-oxide,
in which
alkyl, cycloalkyl and alkoxy, for their part, can be substituted in one to three places, in the same way or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl, and 4- to 7-membered heterocyclyl,
$R^2$ stands for phenyl or pyridyl,
whereby phenyl is substituted with 1 to 3, preferably 2, substituents, whereby the substituents, independently of one another, are selected from the group that consists of halogen, hydroxy, amino, cyano, nitro, ($C_1$-$C_4$)-alkyl, ($C_3$-$C_6$)-cycloalkyl, ($C_1$-$C_4$)-alkylamino, and ($C_1$-$C_4$)-alkoxy,
in which
alkyl, cycloalkyl, alkylamino, and alkoxy, for their part, can be substituted in one to three places, in the same way or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl, and 4- to 7-membered heterocyclyl, and
whereby pyridyl can be substituted with 1 or 2 substituents, whereby the substituents, independently of one another, are selected from the group that consists of halogen, hydroxy, amino, cyano, nitro, ($C_1$-$C_4$)-alkyl, ($C_3$-$C_6$)-cycloalkyl, and ($C_1$-$C_4$)-alkoxy, and whereby the nitrogen atom of pyridyl can form an N-oxide,
in which
alkyl, cycloalkyl, and alkoxy, for their part, can be substituted in one to three places, in the same way or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl, and 4- to 7-membered heterocyclyl, and
A stands for a 5- to 8-membered heterocyclic compound bonded via nitrogen,
whereby the heterocyclic compound can be substituted with 1 to 3 substituents, whereby the substituents, independently of one another, are selected from the group that consists of halogen, hydroxy, hydroxymethyl, formyl, amino, oxo, trifluoromethyl, trifluoromethoxy, ($C_1$-$C_4$)-alkyl, ($C_1$-$C_4$)-alkoxy, and ($C_1$-$C_4$)-alkoxycarbonyl,
whereby $R^2$ stands for pyridyl, when $R^1$ stands for phenyl,
whereby $R^2$ stands for phenyl, when $R^1$ stands for pyridyl, and whereby when $R^1$ stands for 3-pyridyl, the latter cannot be substituted with unsubstituted alkoxy,
and their salts, their solvates, and the solvates of their salts, except for the following compounds

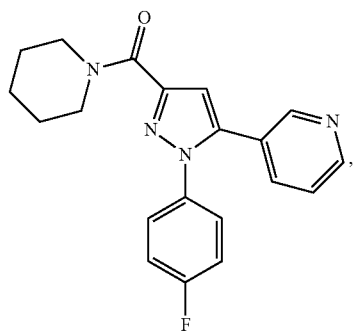

,

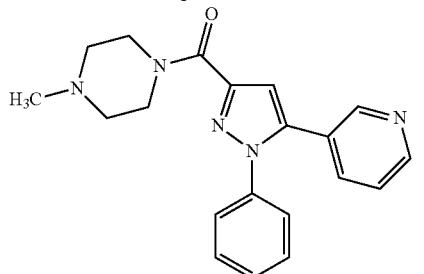

and

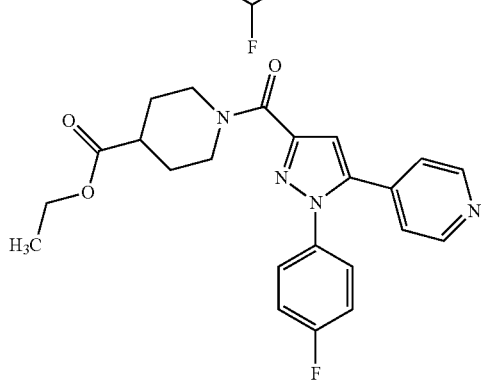

are the subject matter of the invention.

Compounds according to the invention are the compounds of Formulas (I), (Ia), (Ib), (Ic), and (Id) and their salts, solvates, and solvates of salts, as well as the compounds comprised by Formulas (I), (Ia), (Ib), (Ic), and (Id) and mentioned below as embodiment(s), and their salts, solvates, and solvates of salts, to the extent that the compounds comprised by Formulas (I), (Ia), (Ib), (Ic), and (Id) and mentioned below are not already salts, solvates, and solvates of salts.

The compounds according to the invention can exist in stereoisomeric forms (enantiomers, diastereomers) depending on their structure. The invention therefore comprises enantiomers or diastereomers and their respective mixtures. From such mixtures of enantiomers and/or diastereomers, the stereoisomerically uniform components can be isolated in a known way.

If the compounds according to the invention can occur in tautomeric forms, this invention comprises all tautomeric forms.

Within the scope of this invention, physiologically harmless salts of the compounds according to the invention are preferred as salts. Salts that are themselves unsuitable for pharmaceutical applications but can be used, for example, for the isolation or purification of the compounds according to the invention are also comprised, however.

Physiologically harmless salts of the compounds according to the invention comprise acid addition salts of mineral acids, carboxylic acids, and sulfonic acids, e.g., salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid, and benzoic acid.

Physiologically harmless salts of the compounds according to the invention also comprise salts of conventional bases, such as by way of example and preferably alkali metal salts (e.g., sodium and potassium salts), alkaline-earth salts (e.g., calcium and magnesium salts), and ammonium salts, derived from ammonia or organic amines with 1 to 16 C atoms, such as by way of example and preferably ethylamine, diethylamine, triethylamine, ethyldiisopropylamine, monoethanolamine, diethanolamine, tri-ethanolamine, dicyclohexylamine, dimethylaminoethanol, procaine, dibenzylamine, N-methylmorpholine, arginine, lysine, ethylenediamine, and N-methylpiperidine.

Within the scope of the invention, those forms of the compounds according to the invention that form a complex in the solid or liquid state by coordination with solvent molecules are referred to as solvates. Hydrates are a special form of solvates, in which the coordination with water takes place.

Within the scope of this invention, unless otherwise specified, the substituents have the following meaning:

Alkyl as well as the alkyl parts in alkoxy and alkoxycarbonyl stand for straight or branched alkyl and comprise, unless otherwise indicated, $(C_1-C_6)$-alkyl, in particular $(C_1-C_4)$-alkyl, such as, e.g., methyl, ethyl, propyl, isopropyl, butyl, isobutyl, tert-butyl.

Within the scope of the invention, alkoxy preferably stands for a straight-chain or branched alkoxy radical in particular with 1 to 6, 1 to 4, or 1 to 3 carbon atoms. A straight-chain or branched alkoxy radical with 1 to 3 carbon atoms is preferred. By way of example and preferably, the following can be mentioned: methoxy, ethoxy, n-propoxy, isopropoxy, t-butoxy, n-pentoxy, and n-hexoxy.

By way of example and preferably, alkoxycarbonyl stands for methoxycarbonyl, ethoxycarbonyl, n-propoxycarbonyl, isopropoxycarbonyl, t-butoxycarbonyl, n-pentoxycarbonyl, and n-hexoxycarbonyl.

Heterocyclyl stands for a monocyclic, heterocyclic radical with 4 to 8, preferably 5 to 6, ring atoms, and up to 3, preferably up to 2, heteroatoms, and/or hetero groups from the series N, O, S, SO, $SO_2$, whereby a nitrogen atom can also form an N-oxide. The heterocyclic compound can be saturated or partially unsaturated. Preferred are 5- to 7-membered, monocyclic, saturated heterocyclic compounds with up to two heteroatoms from the series O, N and S, by way of example and preferably for 1,4-oxazepanyl, pyrrolidin-1-yl, pyrrolidin-2-yl, pyrrolin-3-yl, tetrahydrofuranyl, tetrahydrothienyl, pyranyl, 1,3-thiazolidinyl, piperidin-1-yl, piperidin-2-yl, piperidin-3-yl, piperidin-4-yl, thiopyranyl, morpholin-2-yl, morpholin-3-yl, morpholin-4-yl, thiomorpholin-2-yl, thiomorpholin-3-yl, thiomorpholin-4-yl, perhydroazepinyl, piperazin-1-yl, piperazin-2-yl.

Halogen stands for fluorine, chlorine, bromine, or iodine, whereby fluorine and chlorine are preferred, unless otherwise indicated.

Within the scope of the invention, $(C_3-C_6)$-cycloalkyl stands for a monocyclic, saturated carbocyclic compound with 3 to 6 ring-carbon atoms. By way of example and preferably, the following can be mentioned: cyclopropyl, cyclobutyl, cyclo-pentyl, and cyclohexyl.

The above-cited radical definitions that are indicated in general or in preferred areas apply both for the end products of Formula (I) and in a corresponding manner for the starting substances or intermediate products required in each case for production.

The radical definitions indicated in particular in the respective combinations or preferred combinations of radicals are also replaced arbitrarily by radical definitions of other combinations independently of the respective indicated combinations of radicals.

Compounds of Formula (I), in which
$R^1$ stands for phenyl or pyridyl,
  whereby phenyl is substituted with 1 or 2 substituents, whereby the substituents, independently of one another, are selected from the group that consists of halogen, amino, methyl, and trifluoromethyl, and whereby pyridyl can be substituted with 1 or 2 substituents, whereby the substituents, independently of one another, are selected from the group that consists of halogen, amino, methyl, and trifluoromethyl, and whereby the nitrogen atom of the pyridyl can form an N-oxide,
$R^2$ stands for phenyl or pyridyl,
  whereby phenyl is substituted with 1 or 2 substituents, whereby the substituents, independently of one another, are selected from the group that consists of halogen, cyano, $(C_1-C_4)$-alkyl, $(C_3-C_6)$-cycloalkyl, and $(C_1-C_4)$-alkoxy,
  in which
    alkyl, cycloalkyl, and alkoxy, for their part, can be substituted with 1 to 3 fluorine atoms, and
    whereby pyridyl can be substituted with 1 or 2 substituents, whereby the substituents, independently of one another, are selected from the group that consists of halogen, cyano, $(C_1-C_4)$-alkyl, $(C_3-C_6)$-cycloalkyl, and $(C_1-C_4)$-alkoxy, and whereby the nitrogen atom of pyridyl can form an N-oxide,
  in which
    alkyl, cycloalkyl, and alkoxy, for their part, can be substituted with 1 to 3 fluorine atoms, and
A stands for pyrrolidin-1-yl, morpholin-4-yl, thiomorpholin-4-yl, 1,3-thiazolidin-3-yl, piperidin-1-yl, piperazin-1-yl or 1,4-oxazepan-4-yl,
  whereby pyrrolidin-1-yl, morpholin-4-yl, thiomorpholin-4-yl, 1,3-thiazolidin-3-yl, piperidin-1-yl, piperazin-1-yl or 1,4-oxazepan-4-yl can be substituted with 1 to 3 substituents, whereby the substituents, independently of one another, are selected from the group that consists of halogen, hydroxy, hydroxymethyl, formyl, amino, oxo, trifluoromethyl, trifluoromethoxy, $(C_1-C_4)$-alkyl, $(C_1-C_4)$-alkoxy, and $(C_1-C_4)$-alkoxycarbonyl,
  whereby $R^2$ stands for pyridyl, when $R^1$ stands for phenyl,
  whereby $R^2$ stands for phenyl, when $R^1$ stands for pyridyl,
  and their salts, their solvates, and the solvates of their salts are also the subject matter of the invention.

Compounds of Formula (I), in which
$R^1$ stands for pyridyl,
  whereby pyridyl can be substituted with 1 or 2 substituents, whereby the substituents, independently of one another, are selected from the group that consists of halogen, amino, methyl, and trifluoromethyl, and whereby the nitrogen atom of pyridyl can form an N-oxide, $R^2$ stands for phenyl,
whereby phenyl is substituted with 1 to 2 substituents, whereby the substituents, independently of one another, are selected from the group that consists of halogen, cyano, $(C_1-C_4)$-alkyl, $(C_3-C_6)$-cycloalkyl, and $(C_1-C_4)$-alkoxy,
in which
alkyl, cycloalkyl, and alkoxy, for their part, can be substituted with 1 to 3 fluorine atoms, and A stands for pyrrolidin-1-yl, morpholin-4-yl, 1,3-thiazolidin-3-yl or piperazin-1-yl,
whereby pyrrolidin-1-yl, morpholin-4-yl, 1,3-thiazolidin-3-yl or piperazin-1-yl can be substituted with 1 to 3 substituents, whereby the substituents, independently of one another, are selected from the group that consists of hydroxy, amino, oxo, $(C_1-C_4)$-alkyl, and $(C_1-C_4)$-alkoxy, and their salts, their solvates, and the solvates of their salts, are also the subject matter of the invention.

Compounds of Formula (I), in which
$R^1$ stands for 3-pyridyl or 4-pyridyl,
whereby pyridyl can be substituted with a halogen substituent,
$R^2$ stands for phenyl,
whereby phenyl is substituted with 1 or 2 substituents, whereby the substituents, independently of one another, are selected from the group that consists of halogen, trifluoroalkoxy, and difluoroalkoxy,
A stands for pyrrolidin-1-yl, morpholin-4-yl, 1,3-thiazolidin-3-yl or piperazin-1-yl,
whereby pyrrolidin-1-yl, morpholin-4-yl, 1,3-thiazolidin-3-yl or piperazin-1-yl can be substituted with 1 to 3 substituents, whereby the substituents, independently of one another, are selected from the group that consists of oxo and $(C_1-C_4)$-alkyl, and their salts, their solvates, and the solvates of their salts, are also the subject matter of the invention.

Compounds of Formula

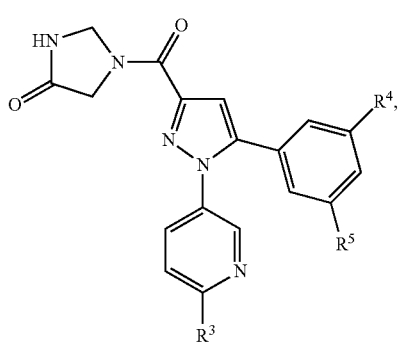

(Ia)

in which
$R^3$ stands for hydrogen, halogen, amino, trifluoromethyl or $(C_1-C_4)$-alkyl,
$R^4$ stands for hydrogen, halogen, $(C_1-C_4)$-alkyl or $(C_1-C_4)$-alkoxy, in which alkyl and alkoxy can be substituted with 1 to 3 fluorine atoms, and
$R^5$ stands for hydrogen, halogen, cyano, $(C_1-C_4)$-alkyl, $(C_3-C_6)$-cycloalkyl or $(C_1-C_4)$-alkoxy, whereby $R^4$ and $R^5$ cannot be hydrogen at the same time, and their salts, their solvates, and the solvates of their salts, are also the subject matter of the invention.

Compounds of Formula (Ia),
in which
$R^3$ stands for hydrogen or methyl,
$R^4$ stands for fluorine, difluoromethoxy or trifluoromethoxy, and
$R^5$ stands for fluorine, chlorine, bromine, or methoxy,
and their salts, their solvates, and the solvates of their salts, are also the subject matter of the invention.

Compounds of Formula

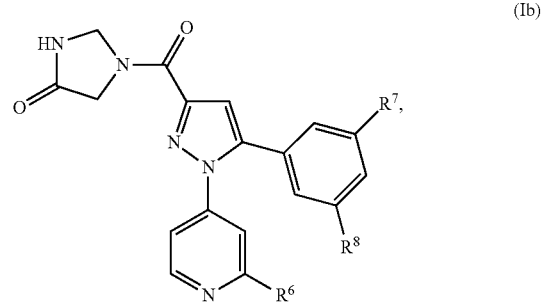

(Ib)

in which
$R^6$ stands for hydrogen, halogen, trifluoromethyl, $(C_1-C_4)$-alkyl or $(C_1-C_4)$-alkoxy,
$R^7$ stands for hydrogen, halogen, $(C_1-C_4)$-alkyl or $(C_1-C_4)$-alkoxy, in which alkyl and alkoxy can be substituted with 1 to 3 fluorine atoms, and
$R^8$ stands for hydrogen, halogen, cyano, $(C_1-C_4)$-alkyl, $(C_3-C_6)$-cycloalkyl or $(C_1-C_4)$-alkoxy,
whereby $R^7$ and $R^8$ cannot be hydrogen at the same time, and their salts, their solvates, and the solvates of their salts, are also the subject matter of the invention.

Compounds of Formula (Ib),
in which
$R^6$ stands for chlorine, trifluoromethyl, methyl, or methoxy,
$R^7$ stands for fluorine, methoxy, difluoromethoxy, or trifluoromethoxy, and
$R^8$ stands for fluorine, chlorine, bromine, or methoxy,
and their salts, their solvates, and the solvates of their salts, are also the subject matter of the invention.

Compounds of Formula

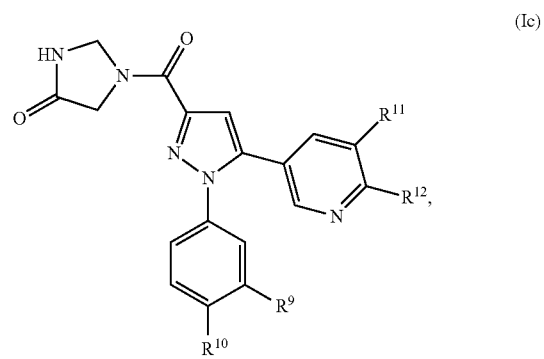

(Ic)

in which
$R^9$ stands for hydrogen, halogen, cyano, $(C_1-C_4)$-alkyl or $(C_1-C_4)$-alkoxy, in which alkyl and alkoxy can be substituted with 1 to 3 fluorine atoms, $R^{10}$ stands for hydrogen, halogen, trifluoromethyl, ($C_1$-$C_4$)-alkyl or ($C_1$-$C_4$)-alkoxy, $R^{11}$ stands for hydrogen, halogen, cyano, ($C_1$-$C_4$)-alkyl or ($C_1$-$C_4$)-alkoxy, in which alkyl and alkoxy can be substituted with 1 to 3 fluorine atoms, and $R^{12}$ stands for hydrogen or halogen, whereby $R^9$ and $R^{11}$ cannot be hydrogen at the same time, and their salts, their solvates, and the solvates of their salts, are also the subject matter of the invention.

Compounds of Formula (Id)

in which $R^{13}$ stands for hydrogen, halogen, cyano, ($C_1$-$C_4$)-alkyl or ($C_1$-$C_4$)-alkoxy, in which alkyl and alkoxy can be substituted with 1 to 3 fluorine atoms, $R^{14}$ stands for hydrogen, halogen, trifluoromethyl, ($C_1$-$C_4$)-alkyl or ($C_1$-$C_4$)-alkoxy, and $R^{15}$ stands for hydrogen, halogen, cyano, ($C_1$-$C_4$)-alkyl or ($C_1$-$C_4$)-alkoxy, in which alkyl and alkoxy can be substituted with 1 to 3 fluorine atoms, whereby $R^{13}$ and $R^{14}$ cannot be hydrogen at the same time, and their salts, their solvates, and the solvates of their salts, are also the subject matter of the invention.

In addition, a method for the production of the compounds of Formulas (I), (Ia), (Ib), (Ic) and (Id), whereby a compound of Formula (II)

in which $R^1$ and $R^2$ have the above-indicated meaning,
is reacted with a 5- to 8-membered heterocyclic compound or a salt thereof,
is the subject matter of the invention.

In general, the reaction takes place in inert solvents, in the presence of a dehydrating reagent, optionally in the presence of a base, preferably in a temperature range of −30° C. to 50° C. at normal pressure.

Inert solvents are, for example, halogenated hydrocarbons, such as dichloromethane or trichloromethane; hydrocarbons, such as benzene or toluene, nitromethane, tetrahydrofuran, 1,4-dioxane, dimethylformamide or acetonitrile. It is also possible to use mixtures of the solvent. Dichloromethane, dimethylformamide, tetrahydrofuran or toluene are especially preferred.

Bases are, for example, alkali carbonates, such as, e.g., sodium or potassium carbonate or -bicarbonate, or organic bases such as trialkylamines, e.g., triethylamine, N-methylmorpholine, N-methylpiperidine, 4-dimethylaminopyridine or diisopropylethylamine.

In this connection, for example, carbodiimides, such as, e.g., N,N'-diethyl-, N,N,'-dipropyl-, N,N'-diisopropyl-, N,N'-dicyclohexylcarbodiimide, N-(3-di-methylaminoisopropyl)-N'-ethylcarbodiimide-hydrochloride (EDC), N-cyclohexyl-carbodiimide-N'-propyloxymethyl-polystyrene (PS-carbodiimide) or carbonyl compounds, such as carbonyldiimidazole, or 1,2-oxazolium compounds such as 2-ethyl-5-phenyl-1,2-oxazolium-3-sulfate or 2-tert-butyl-5-methyl-isoxazolium-perchlorate, or acylamino compounds, such as 2-ethoxy-1-ethoxycarbonyl-1,2-di-hydroquinoline, or propanephosphonic acid anhydride, or isobutyl chloroformate, or bis-(2-oxo-3-oxazolidinyl)-phosphoryl chloride, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)-phosphonium hexafluorophosphate (BOP), or benzotriazol-1-yloxytris(pyrrolidino)-phosphonium hexafluorophosphate (PyBOP), or N-hydroxysuccinimide, or mixtures of the latter, with bases, are suitable as dehydrating reagents.

Preferably, the condensation is carried out with HATU or with EDC in the presence of HOBt.

In an alternative method, a compound of Formula (II) can be reacted first with thionyl chloride and in the second stage with a 5- to 8-membered heterocyclic compound or a salt thereof in the presence of a base, such as, e.g., triethylamine.

The compounds of Formulas (I), (Ia), (Ib), (Ic) and (Id), produced according to the above-indicated method, optionally carry protective groups, which can be cleaved according to the conditions known to one skilled in the art in order to obtain additional compounds of Formulas (I), (Ia), (Ib), (Ic) und (Id).

The compounds of Formulas (I), (Ia), (Ib), (Ic) and (Id), produced according to the above-indicated method, can be converted by selective oxidation with oxidizing agents known to one skilled in the art into additional compounds of Formulas (I), (Ia), (Ib), (Ic) and (Id).

The compounds of Formula (II) are known or can be produced by the ester being saponified with a base in a compound of Formula (III)

in which $R^1$ and $R^2$ have the above-indicated meaning.

The saponification of the ester with a base is carried out in general in inert solvents, preferably in a temperature range from room temperature to reflux of the solvent at normal pressure.

Bases are, for example, alkali hydroxides such as sodium, lithium, or potassium hydroxide, or alkali carbonates such as cesium carbonate, sodium or potassium carbonate; lithium, potassium or sodium hydroxide are preferred.

Inert solvents are, for example, halogenated hydrocarbons, such as methylene chloride, trichloromethane, tetrachloromethane, trichloroethane, tetrachloroethane, 1,2-dichloroethane or trichloroethylene; ethers, such as diethyl ether, methyl-tert-butyl ether, 1,2-dimethoxyethane, 1,4-dioxane, tetrahydrofuran, glycol dimethyl ether or diethylene glycol dimethyl ether; alcohols, such as methanol, ethanol, n-propanol, iso-propanol, n-butanol or tert-butanol; hydrocarbons, such as benzene, xylene, toluene, hexane, cyclohexane or crude oil fractions; or other solvents, such as dimethylformamide, dimethylacetamide, dimethyl sulfoxide, acetonitrile or pyridine, or water, or mixtures of solvents. As solvents, 1,4-dioxane, tetrahydrofuran and/or methanol are preferred. Lithium hydroxide in tetrahydrofuran- or 1,4-dioxane-water mixtures or potassium hydroxide in methanol is preferred.

The compounds of Formula (III) are known or can be produced by a compound of Formula

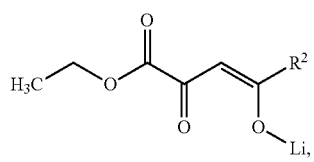

(IV)

in which
$R^2$ has the above-indicated meaning,
being reacted with a compound of Formula

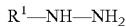

(V), or a salt of a compound of Formula (V),
in which
$R^1$ has the above-indicated meaning,
and being heated in the second stage in acetic acid.

The reaction of the first stage is carried out in general in inert solvents, preferably in a temperature range from room temperature to reflux of the solvent at normal pressure.

Inert solvents are, for example, alcohols, such as methanol, ethanol, n-propanol, iso-propanol, n-butanol, tert-butanol or 2-methoxyethanol; ethanol is preferred.

The reaction of the second stage in acetic acid is carried out in general in a temperature range from room temperature to reflux of the acetic acid at normal pressure. The reaction can also be carried out in methanol, ethanol, or dioxane in a temperature range from room temperature to reflux of the solvent. Mixtures of methanol, ethanol or dioxane with acetic acid in a volume ratio of 0.5/99.5 to 99.5/0.5 are suitable. Also, mixtures of methanol, ethanol, dioxane or acetic acid with other acids, such as, e.g., hydrochloric acid, methanesulfonic acid, p-toluenesulfonic acid, camphorsulfonic acid, or trifluoroacetic acid can be used under the above-mentioned conditions. The reaction in acetic acid is preferably performed under reflux.

The compounds of Formulas (IV) are known, can be synthesized from the corresponding educts according to known methods, or can be produced by a compound of Formula

(VI)

in which
$R^2$ has the above-indicated meaning,
being reacted with an oxalic acid dialkyl ester in the presence of lithium bases.

The reaction is carried out in general in inert solvents, preferably in a temperature range of −78° C. to room temperature.

Inert solvents are, for example, hexane, heptane, cyclohexane, petroleum ether, diethyl ether, diisopropyl ether, tert-butyl methyl ether, tetrahydrofuran, 2-methyl-tetrahydrofuran, 1,4-dioxane and mixtures of the above-mentioned solvent; tetrahydrofuran is preferred. Preferred lithium bases are, for example, n-butyl lithium and lithium hexamethyldisilazide.

The compounds of Formulas (V) and (VI) are known or can be synthesized according to known methods from the corresponding educts.

The production of the compounds according to the invention can be illustrated by the following synthesis diagram.

Synthesis Diagram:

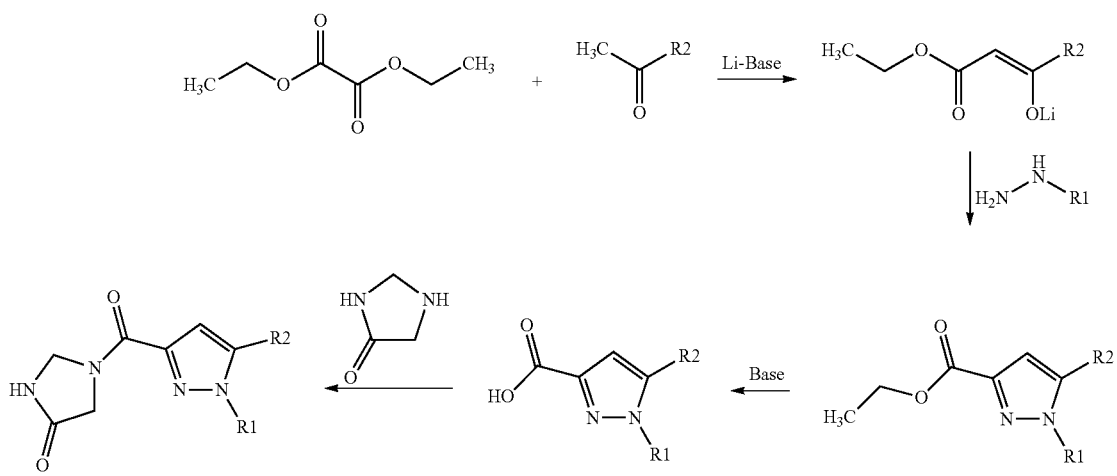

The compounds according to the invention show an unpredictable, valuable pharmacological spectrum of action.

They are therefore suitable for use as pharmaceutical agents for treatment and/or prophylaxis of diseases in humans and animals.

The compounds of this invention are distinguished in particular by an advantageous anti-retroviral spectrum of action.

Another subject of this invention is the use of the compounds according to the invention for treatment and/or prophylaxis of diseases that are caused by retroviruses, in particular HI viruses.

Another subject of this invention is the use of the compounds according to the invention for treatment and/or prophylaxis of diseases, in particular of the above-mentioned diseases.

Another subject of this invention is the use of the compounds according to the invention for the production of a pharmaceutical agent for treatment and/or prophylaxis of diseases, in particular of the above-mentioned diseases.

Another subject of this invention is a method for treatment and/or prophylaxis of diseases, in particular of the above-mentioned diseases, with use of a therapeutically effective amount of the compounds according to the invention.

As types of indications in human medicine, the following can be mentioned, for example:
1.) The treatment and prophylaxis of human retrovirus infections
2.) The treatment and prophylaxis of infections and diseases (AIDS) caused by HIV-1 (human immunodeficiency virus; earlier called HTLV III/LAV) and HIV-2 and the thus associated stages such as ARC (AIDS-related complex) and LAS (Lymphadenopathy syndrome) as well as the immunodeficiency syndrome and encephalopathy caused by this virus.
3.) The treatment of HIV infections caused by single- or multi-resistant HI viruses.
   The term resistant HI viruses means, e.g., viruses with resistance against nucleosidic inhibitors (NRTI), non-nucleosidic inhibitors (NNRTI), integrase inhibitors (II), protease inhibitors (PI) or viruses with resistance against other principles of action, e.g., T20 (fusion inhibitors).
4.) The treatment or the prophylaxis of the AIDS-carrier state (AIDS-exchanger state).
5.) The treatment or the prophylaxis of an HTLV-I or HTLV-II infection.

As indications in veterinary medicine, for example, the following can be cited:
Infections with
a) Maedi-visna (in sheep and goats)
b) Progressive pneumonia virus (PPV) (in sheep and goats)
c) Caprine arthritis encephalitis virus (in sheep and goats)
d) Zwoegerziekte virus (in sheep)
e) Infectious virus of anemia (of horses)
f) Infections caused by the feline leukemia virus
g) Infections caused by the feline immunodeficiency virus (FIV)
h) Infections caused by the simian immunodeficiency virus (SIV)

From the type of indication in human medicine, the above-cited points 2, 3 and 4 are preferred.

The substances for combating HI viruses, which show resistance against known non-nucleosidic inhibitors of reverse transcriptase, such as, e.g., efavirenz or nevirapine, are especially suitable.

Pharmaceutical agents that contain at least one compound according to the invention and at least one or more other active ingredients, in particular for treatment and/or prophylaxis of the above-mentioned diseases, are another subject matter of this invention.

The compounds according to the invention can, in particular in the above-cited points 2, 3, and 4, also be used advantageously as components of a combination therapy with one or more other compounds that are active in these applications. By way of example, these compounds can be used in combination with effective doses of antivirally effective substances, which are based on the principles of action cited below:
Inhibitors of the HIV protease; by way of example, the following can be mentioned: saquinavir, indinavir, ritonavir, nelfinavir, amprenavir, lopinavir, atazanavir, fosamprenavir, tipranavir, darunavir;
Nucleosidic, nucleotidic and non-nucleosidic inhibitors of the HIV reverse transcriptase; by way of example, the following can be mentioned: zidovudine, lamivudine, didanosine, zalcitabine, stavudine, lamivudine, abacavir, tenofovir, adefovir, emtricitabine, amdoxovir, apricitabine, racivir, nevirapine, delavirdine, efavirenz, etravirine, rilpivirine, lersivirine;
Inhibitors of the HIV integrase; by way of example, the following can be mentioned: raltegravir, elvitegravir;
Inhibitors of the HIV fusion; by way of example, the following can be mentioned: enfuvirtide;
Inhibition of CXCR4/CCR5/gp120 interaction; by way of example, the following can be mentioned: maraviroc, vicriviroc, INCB009471, AMD-070;
Inhibition of polyprotein maturation; by way of example, the following can be mentioned: bevirimat.

This selection is to be used for illustrating the possible combinations, but not for limiting the examples cited here. In principle, any combination of the compounds according to the invention with antivirally effective substances is to be considered as within the scope of the invention.

The compounds according to the invention can act systemically and/or locally. For this purpose, they can be administered in a suitable way, such as, e.g., orally, parenterally, pulmonarily, nasally, sublingually, lingually, bucally, rectally, dermally, transdermally, conjunctivally, otically or as an implant or stent.

For these application methods, the compounds according to the invention can be administered in suitable forms of application.

For oral application, forms of application that release the compounds according to the invention in a quick-acting and/or modified way according to the state of the art and that contain the compounds according to the invention in crystalline and/or amorphized and/or dissolved form, such as, e.g., tablets (uncoated or coated tablets, for example with gastric juice-resistant or slow-dissolving or insoluble coatings, which control the release of the compound according to the invention), tablets or films/wafers that quickly dissolve in the oral cavity, films/lyophilisates, capsules (for example, hard- or soft-gelatin capsules), coated tablets, granulates, pellets, powder, emulsions, suspensions, aerosols or solutions, are suitable.

Parenteral administration can be done by bypassing a resorption step (e.g., by intravenous, intraarterial, intracardial, intraspinal or intralumbar means) or by including resorption (e.g., by intramuscular, subcutaneous, intracutaneous, percutaneous or intraperitoneal means). For parenteral administration, i.a., injection and infusion preparations in the form of solutions, suspensions, emulsions, lyophilisates, or sterile powders are suitable as forms of application.

For the other administration methods, e.g., inhalation forms of medication (i.a., powder inhalers, nebulizers), nose drops, nasal solutions, nasal sprays; tablets that are to be administered lingually, sublingually or buccally; films/wafers or capsules, suppositories, ear or eye preparations, vaginal capsules, aqueous suspensions (lotions, shaking mixtures), lipophilic suspensions, ointments, creams, transdermal therapeutic systems (such as, for example, patches), milk, pastes, foams, scattered powders, implants or stents, are suitable.

The compounds according to the invention can be converted into the cited forms of application. This can take place in a way that is known in the art by mixing with inert, non-toxic, pharmaceutically suitable adjuvants. These adjuvants include, i.a., vehicles (for example, microcrystalline cellulose, lactose, mannitol), solvents (e.g., liquid polyethylene glycols), emulsifiers and dispersing agents or wetting agents (for example, sodium dodecyl sulfate, polyoxysorbitanoleate), binders (for example, polyvinylpyrrolidone), synthetic and natural polymers (for example, albumin), stabilizers (e.g., antioxidants, such as, for example, ascorbic acid), dyes (e.g., inorganic pigments, such as, for example, iron oxides), and flavoring and/or odor correctives.

Other subjects of this invention are pharmaceutical agents that contain at least one compound according to the invention, usually together with one or more inert, non-toxic, pharmaceutically suitable adjuvants, as well as their use for the above-mentioned purposes.

In general, it has proven advantageous, in both human and veterinary medicine, to administer the active ingredient or active ingredients according to the invention in total amounts of 0.1 to 200 mg/kg, preferably 1 to 100 mg/kg, of body weight every 24 hours, optionally in the form of several individual administrations, to achieve the desired result. An individual administration contains the active ingredient or active ingredients preferably in amounts of 1 to 80 mg/kg, in particular 1 to 30 mg/kg of body weight.

Nevertheless, it may optionally be necessary to deviate from the above-mentioned amounts, specifically based on body weight, administration method, individual behavior relative to the active ingredient, type of preparation, and time or interval at which the administration is done. Thus, in some cases, it may be sufficient to get by with less than the above-mentioned minimum amount, while in other cases, the above-mentioned upper limit must be exceeded. In the case of the administration of larger amounts, it may be advisable to distribute the latter in several individual administrations over the day.

The percentages in the following tests and examples are, unless otherwise indicated, percents by weight; parts are parts by weight. Solvent ratios, dilution ratios, and concentration information of liquid/liquid solutions in each case relate to the volume. The notation "w/v" means "weight/volume" (Gewicht/Volumen). Thus, for example, "10% w/v" means: 100 ml of solution or suspension contains 10 g of substance.

A EXAMPLES

Abbreviations and Acronyms bs Broad Singlet (in NMR)
bd Broad Doublet (in NMR)
cat. Catalytic
CI Chemical Ionization (in MS)
dd Doublet of Doublet (in NMR)
DMF Dimethylformamide
DMSO Dimethyl Sulfoxide
dt Doublet of Triplet (in NMR)
d. Th. Of Theory (in Yield)
EI Electron Impact Ionization (in MS)
eq. Equivalent(s)
ESI Electrospray-Ionization (in MS)
Et Ethyl
ges. Saturated
h Hour(s)
HPLC High-Pressure, High-Power Liquid Chromatography
konz. Concentrated
LC-MS Liquid-Chromatography-Coupled Mass Spectrometry
LHMDS Lithium Hexamethyldisilazide
m Multiplet (in NMR)
Me Methyl
min Minute(s)
MS Mass Spectrometry
NMR Nuclear Resonance Spectrometry
Ph Phenyl
q Quartet (in NMR)
quint Quintet (in NMR)
RT Room Temperature
$R_t$ Retention Time (in HPLC)
s Singlet (in NMR)
TFA Trifluoroacetic Acid
THF Tetrahydrofuran
UV Ultraviolet Spectrometry
wässr. Aqueous, Aqueous Solution
LC-, MS- and HPLC-Methods:
Method 1 (LC-MS):
  Instrument: Waters ACQUITY SQD UPLC System; column: Waters Acquity UPLC HSS T3 1.8µ 50 mm×1 mm; eluant A: 1 l of water+0.25 ml of 99% formic acid, eluant B: 1 l of acetonitrile+0.25 ml of 99% formic acid; gradient: 0.0 min 90% A→1.2 min 5% A→2.0 min 5% A; oven: 50° C.; flow: 0.40 ml/min; UV detection: 210-400 nm.
Method 2 (LC-MS):
  Instrument: Micromass Quattro Premier with Waters UPLC Acquity; column: Thermo Hypersil GOLD 1.9µ 50×1 mm; eluant A: 1 l of water+0.5 ml of 50% formic acid, eluant B: 1 l of acetonitrile+0.5 ml of 50% formic acid; gradient: 0.0 min 97% A→0.5 min 97% A→3.2 min 5% A 4.0 min 5% A oven: 50° C.; flow: 0.3 ml/min; UV detection: 210 nm.
Method 3 (LC-MS):
  Instrument: Waters ACQUITY SQD UPLC System; column: Waters Acquity UPLC HSS T3 1.8µ 30×2 mm; eluant A: 1 l of water+0.25 ml of 99% formic acid, eluant B: 1 l of acetonitrile+0.25 ml of 99% formic acid; gradient: 0.0 min 90% A→1.2 min 5% A→2.0 min 5% A oven: 50° C.; flow: 0.60 ml/min; UV detection: 208-400 nm.

In purifications of compounds according to the invention per preparative HPLC according to the above-described methods, in which the eluants contain additives such as, for example, trifluoroacetic acid, formic acid, or ammonia, the compounds according to the invention can accumulate in salt form, for example as trifluoroacetate, formate, or ammonium salt, if the compounds according to the invention contain a sufficient basic or acid functionality. Such a salt can be converted into the corresponding free base or acid by various methods that are known to one skilled in the art.

Starting Compounds and Intermediate Compounds:
Starting Compounds:
  The (hetero)arylhydrazines and methyl-(hetero)arylketones that are used are commercially available or were synthesized according to methods known in the literature.
  By way of example, the following references to the synthesis of (hetero)arylhydrazines can be mentioned: K. H. Pilgram Synthetic Communications 1985, 15 (8), 697-706; M. T. Makhija Bioorganic & Medicinal Chemistry 2004, 12

(9), 2317-2333; A. Reisinger Organic & Biomolecular Chemistry 2004, 2 (2), 246-256; V. S. Padalkar Synthetic Communications 2011, 41 (6), 925-938; H. Y. Lo Bioorganic & Medicinal Chemistry Letters 2010, 20 (22), 6379-6383; M. G. C. Kahn Bioorganic & Medicinal Chemistry Letters 2006, 16 (13), 3454-3458; WO 2007/064872; WO 2009/068617; US 2005/0215577; WO 2008/034008; WO 2011/033018.

By way of example, the following references to the synthesis of methyl-(hetero)arylketones can be mentioned: D. B. Bolstad Journal of Medicinal Chemistry 2008, 51 (21), 6839-6852; D. Xu Tetrahedron Letters 2008, 49 (42), 6104-6107; M. A. Chowdhury Journal of Medicinal Chemistry 2009, 52 (6), 1525-1529; J. Zheng Chemical Communications 2007, 48, 5149-5151; US 2009/0209529; WO 2007/064553; WO 2007/031440; WO 2009/077954.

Intermediate Compounds:

Below, the syntheses of the intermediate compounds are described; as a reference, WO 2009/115213 is also pointed out.

Example 1A

Lithium-1-(3-chloro-5-fluorophenyl)-4-ethoxy-3,4-dioxobut-1-en-1-olate

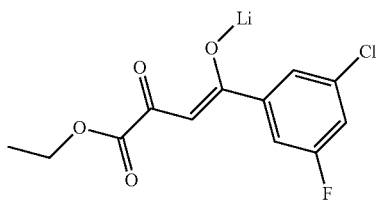

A solution of LHMDS (1 N in THF, 14 ml, 14 mmol) is diluted with diethyl ether (7 ml) and cooled to −78° C. A solution of 3-chloro-5-fluoroacetophenone (2.1 g, 12.2 mmol) in diethyl ether (18 ml) is added, and the mixture is stirred for 45 minutes at −78° C. Then, diethyl oxalate (2 ml, 14.6 mmol) is added in drops at −78° C., heated to room temperature, and the reaction mixture is stirred overnight at room temperature. After the solvent is removed i. vac., 3.9 g is obtained with 85% purity (115% of theory) of the title compound, which is used without further purification in the next step.

LC-MS (Method 1): $R_t$=1.19 min; MS (ESIpos): m/z=272 [M-Li+2H]$^+$.

Example 2A

Lithium-1-(3-bromo-5-fluorophenyl)-4-ethoxy-3,4-dioxobut-1-en-1-olate

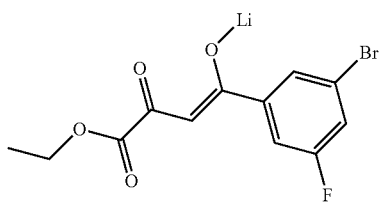

The production of the title compound is carried out starting from 3-bromo-5-fluoroacetophenone (1.76 g, 7.30 mmol) and diethyl oxalate (1.2 ml, 8.76 mmol) analogously to the synthesis of the compound of Example 1A. 2.65 g is obtained with 70% purity (78% of theory) of the title compound, which is used without further purification in the next step.

LC-MS (Method 1): $F_t$=1.19 min; MS (ESIpos): m/z=315 [M-Li]$^-$.

Example 3A

Lithium-1-(3-fluoro-5-trifluoromethoxyphenyl)-4-ethoxy-3,4-dioxobut-1-en-1-olate

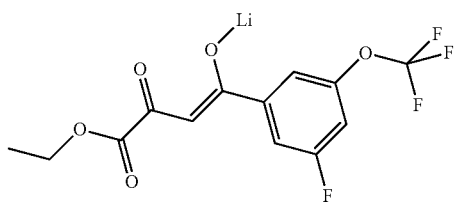

The production of the title compound is carried out starting from 3-fluoro-5-trifluoromethoxyacetophenone (1.08 g, 4.88 mmol) and diethyl oxalate (0.8 ml, 5.86 mmol) analogously to the synthesis of the compound of Example 1A. 1.82 g is obtained with 85% purity (114% of theory) of the title compound, which is used without further purification in the next step.

LC-MS (Method 1): $R_t$=1.19 min; MS (ESIpos): m/z=321 [M−Li+2H]$^+$.

Example 4A

Lithium-1-(3-chloro-5-trifluoromethoxyphenyl)-4-ethoxy-3,4-dioxobut-1-en-1-olate

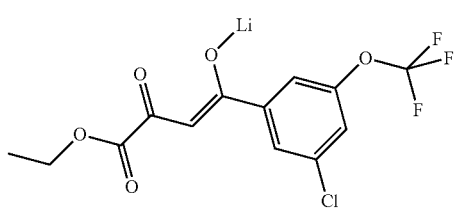

The production of the title compound is carried out starting from 3-chloro-5-trifluoromethoxyacetophenone (2.43 g, 10.19 mmol) and diethyl oxalate (1.66 ml, 12.22 mmol) analogously to the synthesis of the compound of Example 1A. 3.87 g is obtained with 84% purity (92% of theory) of the title compound, which is used without further purification in the next step.

LC-MS (Method 1): $R_t$=1.29 min; MS (ESIpos): m/z=337 [M-Li]$^-$.

Example 5A

Lithium-1-(3-bromo-5-trifluoromethoxyphenyl)-4-ethoxy-3,4-dioxobut-1-en-1-olate

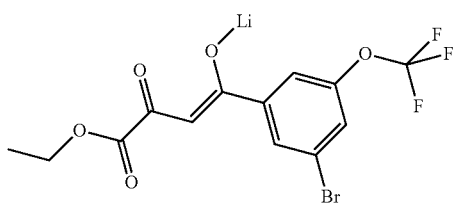

The production of the title compound is carried out starting from 3-bromo-5-trifluoromethoxyacetophenone (2.10 g, 7.42 mmol) and diethyl oxalate (1.22 ml, 8.90 mmol) analogously to the synthesis of the compound of Example 1A. 3.30 g is obtained with 85% purity (114% of theory) of the title compound, which is used without further purification in the next step.

LC-MS (Method 1): $R_t$=1.33 min; MS (ESIpos): m/z=381 [M-Li]$^-$.

Example 6A

Lithium-1-(3-bromo-5-methoxyphenyl)-4-ethoxy-3,4-dioxobut-1-en-1-olate

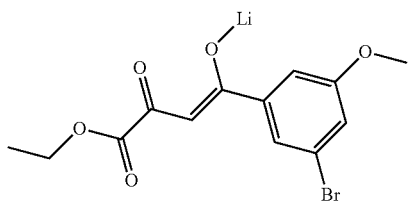

The production of the title compound is carried out starting from 3-bromo-5-methoxyacetophenone (1.05 g, 4.59 mmol) and diethyl oxalate (0.75 ml, 5.51 mmol) analogously to the synthesis of the compound of Example 1A. 1.85 g is obtained with 80% purity (120% of theory) of the title compound, which is used without further purification in the next step.

LC-MS (Method 1): $R_t$=1.22 min; MS (ESIpos): m/z=327 [M-Li]$^-$.

Example 7A

Lithium-1-(3-difluoromethoxy-5-fluorophenyl)-4-ethoxy-3,4-dioxobut-1-en-1-olate

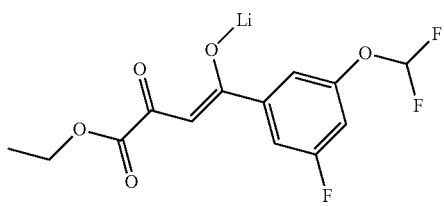

The production of the title compound is carried out starting from 3-difluoromethoxy-5-fluoroacetophenone (1.05 g, 5.12 mmol) and diethyl oxalate (0.83 ml, 6.14 mmol) analogously to the synthesis of the compound of Example 1A. 1.77 g is obtained with 53% purity (59% of theory) of the title compound, which is used without further purification in the next step.

LC-MS (Method 1): $R_t$=1.11 min; MS (ESIpos): m/z=303 [M-Li]$^-$.

Example 8A

Lithium-1-(3-chloro-5-difluoromethoxyphenyl)-4-ethoxy-3,4-dioxobut-1-en-1-olate

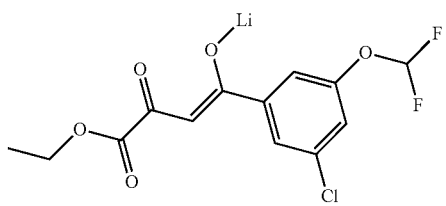

The production of the title compound is carried out starting from 3-chloro-5-difluoromethoxyacetophenone (235 mg, 1.07 mmol) and diethyl oxalate (170 µl, 1.28 mmol) analogously to the synthesis of the compound of Example 1A. 356 mg is obtained with 75% purity (78% of theory) of the title compound, which is used without further purification in the next step.

LC-MS (Method 1): $R_t$=1.21 min; MS (ESIpos): m/z=319 [M-Li]$^-$.

Example 9A

Lithium-1-(3-bromo-5-difluoromethoxyphenyl)-4-ethoxy-3,4-dioxobut-1-en-1-olate

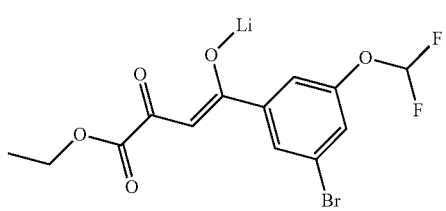

The production of the title compound is carried out starting from 3-bromo-5-difluoromethoxyacetophenone (319 mg, 1.21 mmol) and diethyl oxalate (200 µl, 1.45 mmol) analogously to the synthesis of the compound of Example 1A. 495 mg is obtained with 90% purity (110% of theory) of the title compound, which is used without further purification in the next step.

LC-MS (Method 1): $R_t$=1.24 min; MS (ESIpos): m/z=363 [M-Li]$^-$.

Example 10A

Lithium-1-(3-methoxy-5-trifluoromethoxyphenyl)-4-ethoxy-3,4-dioxobut-1-en-1-olate

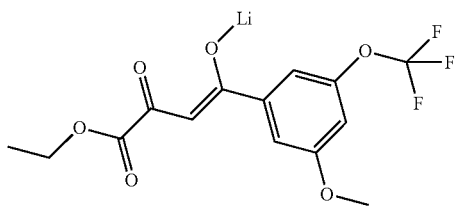

The production of the title compound is carried out starting from 3-methoxy-5-trifluoromethoxyacetophenone (1.10 g, 4.23 mmol) and diethyl oxalate (0.69 ml, 5.07 mmol) analogously to the synthesis of the compound of Example 1A. 1.66 g is obtained with 88% purity (102% of theory) of the title compound, which is used without further purification in the next step.

LC-MS (Method 1): $R_t$=1.24 min; MS (ESIpos): m/z=333 [M-Li]$^-$.

Example 11A

Lithium-1-(3-cyano-5-trifluoromethoxyphenyl)-4-ethoxy-3,4-dioxobut-1-en-1-olate

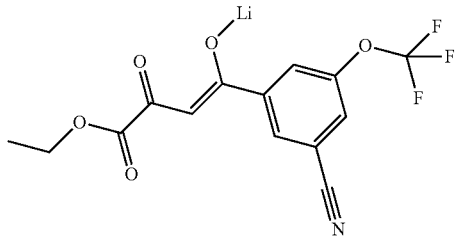

The production of the title compound is carried out starting from 3-cyano-5-trifluoromethoxyacetophenone (611 mg, 2.67 mmol) and diethyl oxalate (0.44 ml, 3.20 mmol) analogously to the synthesis of the compound of Example 1A. 952 mg is obtained with 90% purity (106% of theory) of the title compound, which is used without further purification in the next step.

LC-MS (Method 3): $R_t$=1.19 min; MS (ESIpos): m/z=328 [M-Li]$^-$.

Example 12A

Lithium-1-(3-fluoro-5-[2',2',2'-trifluoroethoxy]phenyl)-4-ethoxy-3,4-dioxobut-1-en-1-olate

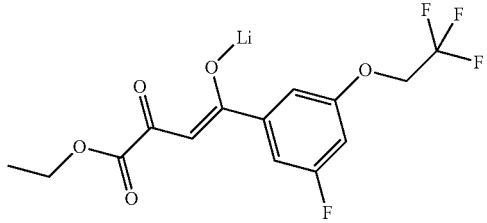

The production of the title compound is carried out starting from 3-fluoro-5-[2',2',2'-trifluoroethoxy]acetophenone (1.53 g, 6.46 mmol) and diethyl oxalate (1.06 ml, 8.76 mmol) analogously to the synthesis of the compound of Example 1A. 2.41 g is obtained with 90% purity (109% of theory) of the title compound, which is used without further purification in the next step.

LC-MS (Method 3): $R_t$=1.25 min; MS (ESIpos): m/z=335 [M-Li]$^-$.

Example 13A

Lithium-1-(5-fluoropyridin-3-yl)-4-ethoxy-3,4-dioxobut-1-en-1-olate

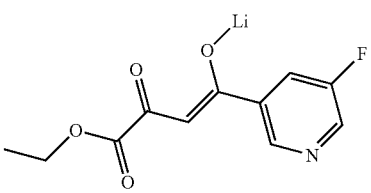

The production of the title compound is carried out starting from 1-(5-fluoro-3-pyridinyl)ethanone (1.50 g, 10.78 mmol) and diethyl oxalate (1.76 ml, 12.94 mmol) analogously to the synthesis of the compound of Example 1A. 3.30 g is obtained with 85% purity (106% of theory) of the title compound, which is used without further purification in the next step.

LC-MS (Method 1): $R_t$=0.94 min; MS (ESIpos): m/z=238 [M-Li]$^-$.

Example 14A

Lithium-1-(5-chloropyridin-3-yl)-4-ethoxy-3,4-dioxobut-1-en-1-olate

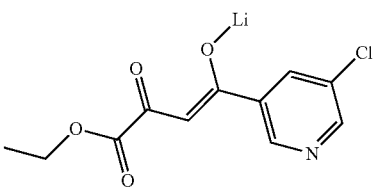

The production of the title compound is carried out starting from 1-(5-chloro-3-pyridinyl)ethanone (1.50 g, 9.64 mmol) and diethyl oxalate (1.57 ml, 11.57 mmol) analogously to the synthesis of the compound of Example 1A. 3.82 g is obtained with 71% purity (107% of theory) of the title compound, which is used without further purification in the next step.

LC-MS (Method 1): $R_t$=0.94 min; MS (ESIpos): m/z=254 [M-Li]$^-$.

Example 15A

Lithium-1-(5-chloro-6-fluoropyridin-3-yl)-4-ethoxy-3,4-dioxobut-1-en-1-olate

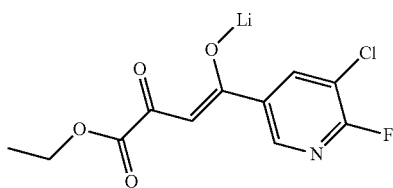

The production of the title compound is carried out starting from 1-(4-chloro-5-fluoro-3-pyridinyl)ethanone (300 mg, 1.73 mmol) and diethyl oxalate (0.28 ml, 2.07 mmol) analogously to the synthesis of the compound of Example 1A. 480 mg is obtained with 100% purity (45% of theory) of the title compound, which is used without further purification in the next step.

LC-MS (Method 3): $R_t$=1.10 min; MS (ESIpos): m/z=272 [M-Li]$^-$.

Example 16A

Lithium-1-(5-methoxypyridin-3-yl)-4-ethoxy-3,4-dioxobut-1-en-1-olate

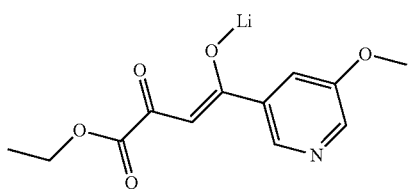

The production of the title compound is carried out starting from 1-(5-methoxy-3-pyridinyl)ethanone (1.43 g, 8.30 mmol) and diethyl oxalate (1.35 ml, 9.96 mmol) analogously to the synthesis of the compound of Example 1A. 2.76 g is obtained with 57% purity (73% of theory) of the title compound, which is used without further purification in the next step.

LC-MS (Method 1): $R_t$=0.83 min; MS (ESIpos): m/z=250 [M-Li]$^-$.

Example 17A

Lithium-1-(5-difluoromethoxypyridin-3-yl)-4-ethoxy-3,4-dioxobut-1-en-1-olate

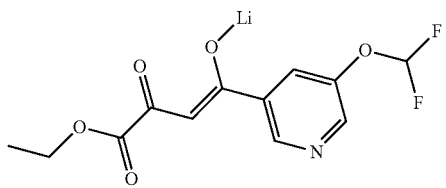

The production of the title compound is carried out starting from 1-(5-difluoromethoxy-3-pyridinyl)ethanone (380 mg, 2.03 mmol) and diethyl oxalate (0.33 ml, 2.44 mmol) analogously to the synthesis of the compound of Example 1A. 662 mg is obtained with 85% purity (111% of theory) of the title compound, which is used without further purification in the next step.

Example 18A

Lithium-1-(5-trifluoromethoxypyridin-3-yl)-4-ethoxy-3,4-dioxobut-1-en-1-olate

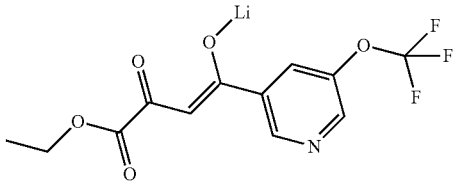

The production of the title compound is carried out starting from 1-(5-trifluoromethoxy-3-pyridinyl)ethanone (1.27 g, 6.72 mmol) and diethyl oxalate (1.10 ml, 8.06 mmol) analogously to the synthesis of the compound of Example 1A. 2.26 g is obtained with 85% purity (114% of theory) of the title compound, which is used without further purification in the next step.

LC-MS (Method 1): $R_t$=0.97 min; MS (ESIpos): m/z=288 [M-Li]$^-$.

Example 19A

Lithium-1-(2-chloropyridin-4-yl)-4-ethoxy-3,4-dioxobut-1-en-1-olate

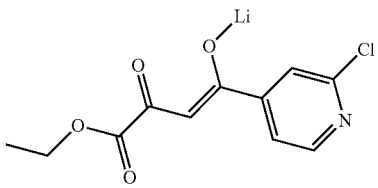

The production of the title compound is carried out starting from 1-(2-chloro-4-pyridinyl)ethanone (1.00 g, 6.43 mmol) and diethyl oxalate (1.05 ml, 7.71 mmol) analogously to the synthesis of the compound of Example 1A. 1.68 g is obtained with 100% purity (100% of theory) of the title compound, which is used without further purification in the next step.

Example 20A 5-(3-Chloro-5-fluorophenyl)-1-(pyridin-2-yl)-1H-pyrazole-3-carboxylic acid

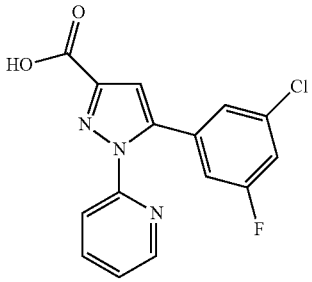 [SMILES: O=C(O)c1cc(-c2cc(F)cc(Cl)c2)n(-c2ccccn2)n1]

A solution of 1.30 g (3.97 mmol) of the compound of Example 1A and 866 mg (5.95 mmol) of 2-pyridylhydrazine hydrochloride in 6 ml of ethanol is stirred for 5 hours at room temperature. The solvent is removed i. vac., and the residue is dissolved in 6 ml of glacial acetic acid. The solution is stirred under reflux for 2 hours, diluted with ethyl acetate, and washed twice with water, twice with saturated sodium bicarbonate solution, and once with saturated sodium chloride solution. The organic phase is dried on sodium sulfate, and the solvent is removed i. vac. The residue is dissolved in acetonitrile/DMSO, filtered over a Millipore, and purified in two portions via preparative HPLC (mobile solvent: acetonitrile/water gradient). 856 mg (62% of theory) of the ethyl ester of the title compound is obtained.

The compound obtained in the first stage is introduced into 10 ml of THF, and a solution of 998 mg (23.80 mmol) of lithium hydroxide monohydrate in 3 ml of water is added to the solution. The reaction mixture is stirred overnight at room temperature, made acidic with 1 N hydrochloric acid, and diluted with ethyl acetate. The aqueous phase is separated and discarded. The organic phase is washed twice with water and once with saturated sodium chloride solution, dried on sodium sulfate, and concentrated by evaporation i. vac. The residue is stirred with diethyl ether/pentane, filtered, and dried. 722 mg (57% of theory) of the title compound is obtained.

$^{1}$H-NMR (400 MHz, DMSO-$d_6$): δ=7.12-7.18 (m, 1H), 7.21 (s, 1H), 7.23 (s, 1H), 7.46 (dt, 11H), 7.51 (dd, 1H), 7.82 (d, 1H), 8.11 (dt, 1H), 8.36 (d, 1H), 13.18 (bs, 1H).

LC-MS (Method 1): $R_t$=0.89 min; MS (ESIpos): m/z=318 [M+H]$^+$.

Example 21A 5-(3-Chloro-5-fluorophenyl)-1-(6-chloropyridin-2-yl)-1H-pyrazole-3-carboxylic acid

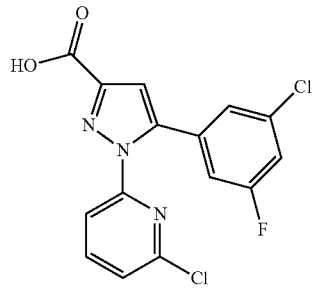 [SMILES: O=C(O)c1cc(-c2cc(F)cc(Cl)c2)n(-c2cccc(Cl)n2)n1]

1.30 g (3.97 mmol) of the compound of Example 1A is reacted analogously to the synthesis of the compound of Example 20A with 854 mg (5.95 mmol) of 6-chloropyridin-2-yl-hydrazine. After hydrolysis, 815 mg (58% of theory) of the title compound is obtained.

$^{1}$H-NMR (400 MHz, DMSO-$d_6$): δ=7.22 (s, 1H), 7.26 (d, 1H), 7.32 (s, 1H), 7.52 (dt, 1H), 7.61 (d, 1H), 7.83 (d, 1H), 8.13 (t, 1H), 13.30 (bs, 1H).

LC-MS (Method 1): $R_t$=1.01 min; MS (ESIpos): m/z=352 [M+H]$^+$.

Example 22A 5-(3-Chloro-5-fluorophenyl)-1-(pyridin-3-yl)-1H-pyrazole-3-carboxylic acid

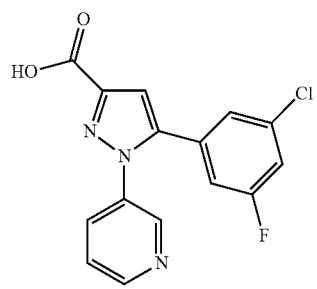

807 mg (2.90 mmol) of the compound of Example 1A is reacted analogously to the synthesis of the compound of Example 20A with 464 mg (3.19 mmol) of 3-pyridylhydrazine hydrochloride. After hydrolysis, 353 mg (38% of theory) of the title compound is obtained.

$^{1}$H-NMR (400 MHz, DMSO-$d_6$): δ=7.19 (d, 1H), 7.25 (d, 2H), 7.48-7.59 (m, 2H), 7.85 (d, 1H), 8.58 (d, 1H), 8.66 (d, 1H); COOH, undetectable.

LC-MS (Method 1): $R_t$=0.81 min; MS (ESIpos): m/z=318 [M+H]$^+$.

Example 23A 5-(3-Chloro-5-fluorophenyl)-1-(6-chloropyridin-3-yl)-1H-pyrazole-3-carboxylic acid

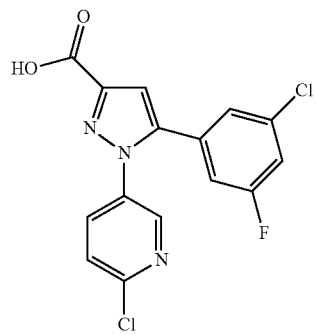 [SMILES: O=C(O)c1cc(-c2cc(F)cc(Cl)c2)n(-c2ccc(Cl)nc2)n1]

1.21 g (4.35 mmol) of the compound of Example 1A is reacted analogously to the synthesis of the compound of Example 20A with 1.04 g (4.78 mmol) of 4-chloropyridin-3-yl-hydrazine dihydrochloride. After hydrolysis, 220 mg (14% of theory) of the title compound is obtained.

$^{1}$H-NMR (400 MHz, DMSO-$d_6$): δ=7.24 (dt, 1H), 7.27 (s, 1H), 7.32 (s, 1H), 7.54 (dt, 1H), 7.68 (d, 1H), 7.86-7.92 (m, 1H), 8.46 (d, 1H), 13.23 (bs, 1H).

LC-MS (Method 1): $R_t$=0.95 min; MS (ESIpos): m/z=352 [M+H]$^+$.

Example 24A 5-(3-Chloro-5-fluorophenyl)-1-(6-methylpyridin-3-yl)-1H-pyrazole-3-carboxylic acid

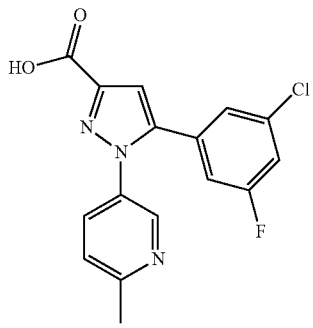 [SMILES: Cc1ccc(-n2nc(C(=O)O)cc2-c2cc(F)cc(Cl)c2)cn1]

785 g (2.25 mmol) of the compound of Example 1A is reacted analogously to the synthesis of the compound of Example 20A with 599 mg (3.38 mmol) of 6-methylpyridin-3-yl-hydrazine hydrochloride. After hydrolysis, 60 mg (8% of theory) of the title compound is obtained.

$^1$H-NMR (400 MHz, DMSO-$d_6$): δ=2.49-2.56 (m, 3H), 7.18 (dt, 1H), 7.25 (s, 1H), 7.27 (s, 1H), 7.40 (d, 1H), 7.51 (dt, 1H), 7.72 (dd, 1H), 8.44 (d, 1H), 13.14 (bs, 1H).

LC-MS (Method 1): $R_t$=0.88 min; MS (ESIpos): m/z=332 [M+H]$^+$.

Example 25A 5-(3-Chloro-5-fluorophenyl)-1-(6-aminopyridin-3-yl)-1H-pyrazole-3-carboxylic acid

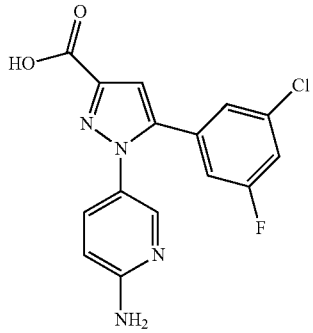 [SMILES: Nc1ccc(-n2nc(C(=O)O)cc2-c2cc(F)cc(Cl)c2)cn1]

70 mg (80%, 0.16 mmol) of the compound of Example 23A is mixed with ammonia solution (14 N, 1.5 ml) and kept in the microwave in a sealed tube for 13 hours at 150° C., whereby a pressure of 20 bar develops. After cooling to room temperature, the ammonia solution is removed i. vac., and the residue is purified via preparative HPLC (mobile solvent: acetonitrile/water gradient). 20 mg (38% of theory) of the title compound is obtained.

$^1$H-NMR (400 MHz, DMSO-$d_6$): δ=6.41 (s, 1), 6.47 (d, 1H), 7.17 (d, 1H), 7.20 (s, 1H), 7.24 (s, 1H), 7.39 (dd, 1H), 7.48 (dt, 1H), 7.86 (d, 1H); COOH, undetectable.

LC-MS (Method 1): $R_t$=0.72 min; MS (ESIpos): m/z=333 [M+H]$^+$.

Example 26A 5-(3-Chloro-5-fluorophenyl)-1-(5-chloropyridin-3-yl)-1H-pyrazole-3-carboxylic acid

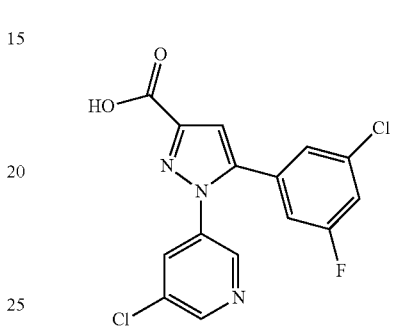

785 mg (2.25 mmol) of the compound of Example 1A is reacted analogously to the synthesis of the compound of Example 20A with 608 mg (3.38 mmol) of 5-chloropyridin-3-yl-hydrazine hydrochloride. After hydrolysis, 270 mg (34% of theory) of the title compound is obtained.

$^1$H-NMR (400 MHz, DMSO-$d_6$): δ=7.24 (dt, 1H), 7.29 (s, 1H), 7.31 (s, 1H), 7.55 (dt, 1H), 8.13 (t, 1H), 8.50 (d, 1H), 8.75 (d, 1H), 13.25 (bs, 1H).

LC-MS (Method 1): $R_t$=0.97 min; MS (ESIpos): m/z=352 [M+H]$^+$.

Example 27A 5-(3-Chloro-5-fluorophenyl)-1-(pyridin-4-yl)-1H-pyrazole-3-carboxylic acid

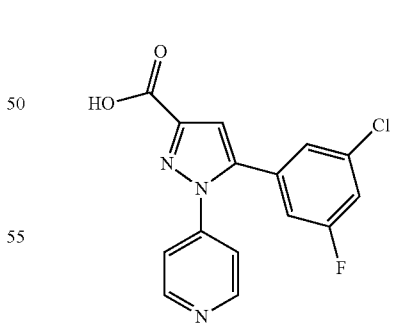

1.30 g (3.97 mmol) of the compound of Example 1A is reacted analogously to the synthesis of the compound of Example 20A with 1.08 g (5.95 mmol) of 4-pyridylhydrazine dihydrochloride. After hydrolysis, 9 mg (0.7% of theory) of the title compound is obtained.

LC-MS (Method 1): $R_t$=0.74 min; MS (ESIpos): m/z=318 [M+H]$^+$.

Example 28A 5-(3-Chloro-5-fluorophenyl)-1-(2-chloropyridin-4-yl)-1H-pyrazole-3-carboxylic acid

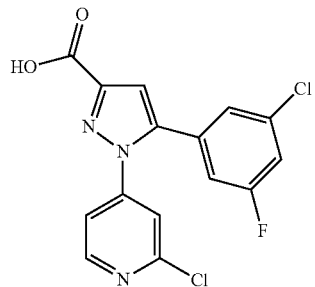

807 mg (2.90 mmol) of the compound of Example 1A is reacted analogously to the synthesis of the compound of Example 20A with 574 mg (3.19 mmol) of 2-chloropyridin-4-yl-hydrazine hydrochloride. After hydrolysis, 248 mg (24% of theory) of the title compound is obtained.

$^1$H-NMR (400 MHz, DMSO-d$_6$): δ=7.27 (s, 1H), 7.28-7.34 (m, 2H), 7.37-7.40 (m, 1H), 7.57 (d, 1H), 7.60 (dt, 1H), 8.48 (d, 1H), 13.35 (bs, 1H).

LC-MS (Method 1): R$_t$=0.98 min; MS (ESIpos): m/z=352 [M+H]$^+$.

Example 29A 5-(3-Chloro-5-fluorophenyl)-1-(2-trifluoromethylpyridin-4-yl)-1H-pyrazole-3-carboxylic acid

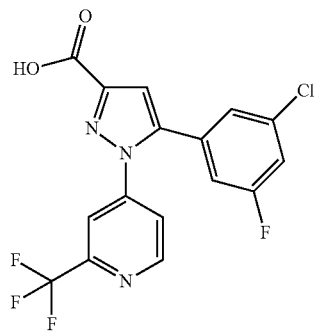 [SMILES: O=C(O)c1cc(-c2cc(F)cc(Cl)c2)n(-c2ccnc(C(F)(F)F)c2)n1]

500 mg (1.53 mmol) of the compound of Example 1A is reacted analogously to the synthesis of the compound of Example 20A with 358 mg (1.68 mmol) of 2-trifluoromethylpyridin-4-yl-hydrazine hydrochloride. After hydrolysis, 444 mg (75% of theory) of the title compound is obtained.

$^1$H-NMR (400 MHz, DMSO-d$_6$): δ=7.27 (s, 1H), 7.34 (d, 1H), 7.41 (s, 1H), 7.58-7.64 (m, 2H), 7.85 (d, 1H), 8.82 (d, 1H); COOH, undetectable.

LC-MS (Method 1): R$_t$=0.99 min; MS (ESIpos): m/z=386 [M+H]$^+$.

Example 30A 5-(3-Chloro-5-fluorophenyl)-1-(2-methylpyridin-4-yl)-1H-pyrazole-3-carboxylic acid

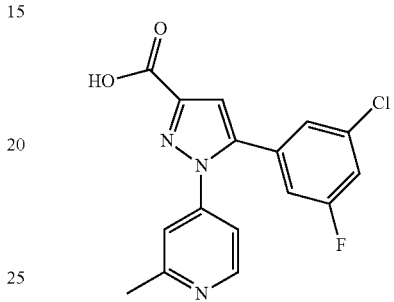

500 mg (1.53 mmol) of the compound of Example 1A is reacted analogously to the synthesis of the compound of Example 20A with 342 mg (1.68 mmol) of 2-methylpyridin-4-yl-hydrazine hydrobromide. After hydrolysis, 425 mg (84% of theory) of the title compound is obtained.

$^1$H-NMR (400 MHz, DMSO-d$_6$): δ=2.47-2.53 (m, 3H), 7.06 (dd, 1H), 7.20-7.27 (m, 2H), 7.30 (s, 1H), 7.37 (d, 1H), 7.53-7.59 (m, 1H), 8.49 (d, 1H), 13.24 (bs, 1H).

LC-MS (Method 2): R$_t$=1.73 min; MS (ESIpos): m/z=332 [M+H]$^+$.

Example 31A 5-(3-Chloro-5-fluorophenyl)-1-(2-methoxypyridin-4-yl)-1H-pyrazole-3-carboxylic acid

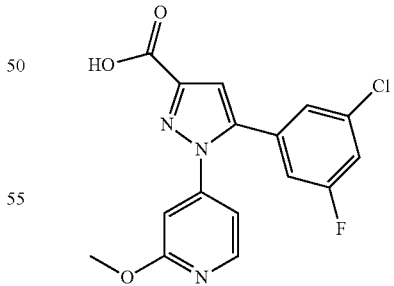

500 mg (1.53 mmol) of the compound of Example 1A is reacted analogously to the synthesis of the compound of Example 20A with 295 mg (1.68 mmol) of 2-methoxypyridin-4-yl-hydrazine hydrochloride. After hydrolysis, 8 mg (1.5% of theory) of the title compound is obtained.

LC-MS (Method 1): R$_t$=0.93 min; MS (ESIpos): m/z=348 [M+H]$^+$.

Example 32A 5-(3-Bromo-5-fluorophenyl)-1-(pyridin-3-yl)-1H-pyrazole-3-carboxylic acid

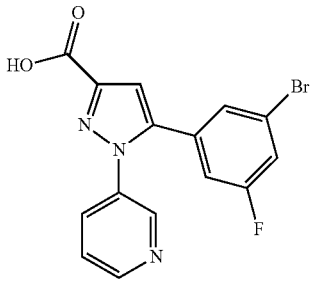 [SMILES: O=C(O)c1cc(-c2cc(F)cc(Br)c2)n(-c2cccnc2)n1]

600 mg (1.30 mmol) of the compound of Example 2A is reacted analogously to the synthesis of the compound of Example 20A with 208 mg (1.43 mmol) of 3-pyridylhydrazine hydrochloride. After hydrolysis, 406 mg (86% of theory) of the title compound is obtained.

$^1$H-NMR (400 MHz, DMSO-d$_6$): δ=7.23 (d, 1H), 7.28 (s, 1H), 7.36 (s, 1H), 7.56 (dd, 1H), 7.63 (dt, 1H), 7.86 (dt, 1H), 8.59 (d, 1H), 8.67 (d, 1H), 13.18 (bs, 1H).

LC-MS (Method 1): R$_t$=0.88 min; MS (ESIpos): m/z=362 [M+H]$^+$.

Example 33A 5-(3-Bromo-5-fluorophenyl)-1-(2-chloropyridin-4-yl)-1H-pyrazole-3-carboxylic acid

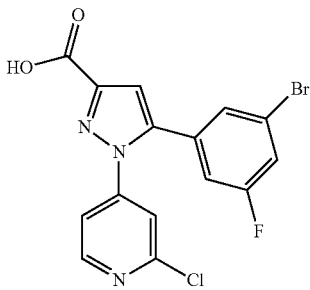 [SMILES: O=C(O)c1cc(-c2cc(F)cc(Br)c2)n(-c2ccnc(Cl)c2)n1]

600 mg (1.30 mmol) of the compound of Example 2A is reacted analogously to the synthesis of the compound of Example 20A with 257 mg (1.43 mmol) of 2-chloropyridin-4-yl-hydrazine hydrochloride. After hydrolysis, 175 mg (34% of theory) of the title compound is obtained.

$^1$H-NMR (400 MHz, DMSO-d$_6$): δ=7.27 (s, 1H), 7.31 (dd, 1H), 7.35 (dt, 1H), 7.49 (s, 1H), 7.57 (d, 1H), 7.71 (dt, 1H), 8.48 (d, 1H), 13.35 (bs, 1H).

LC-MS (Method 1): R$_t$=1.00 min; MS (ESIpos): m/z=396 [M+H]$^+$.

Example 34A 5-(3-Fluoro-5-trifluoromethoxyphenyl)-1-(pyridin-3-yl)-1H-pyrazole-3-carboxylic acid

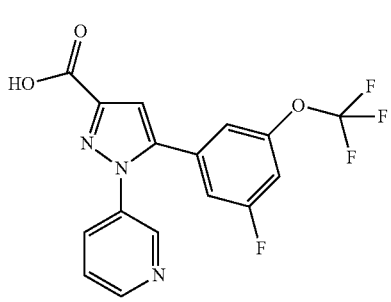 [SMILES: O=C(O)c1cc(-c2cc(F)cc(OC(F)(F)F)c2)n(-c2cccnc2)n1]

1.82 g (4.71 mmol) of the compound of Example 3A is reacted analogously to the synthesis of the compound of Example 20A with 1.03 g (7.07 mmol) of 3-pyridylhydrazine hydrochloride. After hydrolysis, 1.12 g (65% of theory) of the title compound is obtained.

$^1$H-NMR (400 MHz, DMSO-d$_6$): δ=7.03 (s, 1H), 7.32 (s, 1H), 7.41 (d, 1H), 7.48 (d, 1H), 7.55 (dd, 1H), 7.83-7.89 (m, 1H), 8.58 (d, 1H), 8.67 (dd, 1H), 13.20 (bs, 1H).

LC-MS (Method 1): R$_t$=0.87 min; MS (ESIpos): m/z=368 [M+H]$^+$.

Example 35A 5-(3-Fluoro-5-trifluoromethoxyphenyl)-1-(2-chloropyridin-4-yl)-1H-pyrazole-3-carboxylic acid

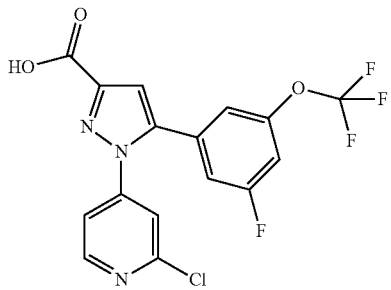 [SMILES: O=C(O)c1cc(-c2cc(F)cc(OC(F)(F)F)c2)n(-c2ccnc(Cl)c2)n1]

500 mg (1.37 mmol) of the compound of Example 3A is reacted analogously to the synthesis of the compound of Example 20A with 272 mg (1.51 mmol) of 2-chloropyridin-4-yl-hydrazine hydrochloride. After hydrolysis, 261 mg (47% of theory) of the title compound is obtained.

LC-MS (Method 3): R$_t$=1.04 min; MS (ESIpos): m/z=402 [M+H]$^+$.

Example 36A 5-(3-Chloro-5-trifluoromethoxyphenyl)-1-(pyridin-3-yl)-1H-pyrazole-3-carboxylic acid

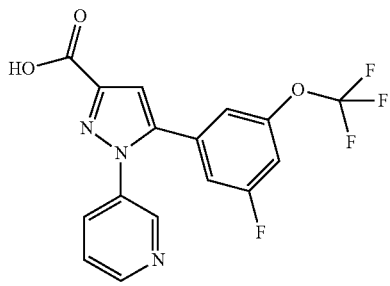 [SMILES: O=C(O)c1cc(-c2cc(F)cc(OC(F)(F)F)c2)n(-c2cccnc2)n1]

500 mg (1.23 mmol) of the compound of Example 4A is reacted analogously to the synthesis of the compound of Example 20A with 197 mg (1.36 mmol) of 3-pyridylhydrazine hydrochloride. After hydrolysis, 203 mg (43% of theory) of the title compound is obtained.

$^1$H-NMR (400 MHz, DMSO-d$_6$): δ=7.16 (s, 1H), 7.34 (s, 1H), 7.55 (dd, 1H), 7.58-7.61 (m, 2H), 7.64 (s, 1H), 7.86 (dt, 1H), 8.67 (dd, 1H), 13.19 (bs, 1H).

LC-MS (Method 3): R$_t$=0.98 min; MS (ESIpos): m/z=384 [M+H]$^+$.

Example 37A 5-(3-Bromo-5-trifluoromethoxyphenyl)-1-(pyridin-2-yl)-1H-pyrazole-3-carboxylic acid

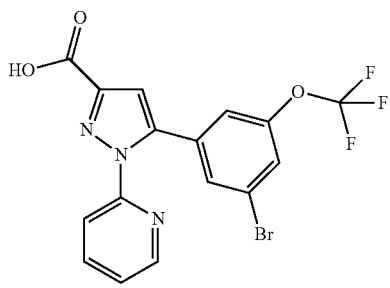 [SMILES: O=C(O)c1cc(-c2cc(Br)cc(OC(F)(F)F)c2)n(-c2ccccn2)n1]

1.10 g (2.40 mmol) of the compound of Example 5A is reacted analogously to the synthesis of the compound of Example 20A with 525 mg (3.61 mmol) of 2-pyridylhydrazine hydrochloride. After hydrolysis, 557 mg (54% of theory) of the title compound is obtained.

$^1$H-NMR (400 MHz, DMSO-d$_6$): δ=7.19 (s, 1H), 7.29 (s, 1H), 7.51 (dd, 1H), 7.66-7.72 (m, 2H), 7.84 (d, 1H), 8.11 (dt, H), 8.32 (d, 1H), 13.20 (bs, 1H).

LC-MS (Method 1): R$_t$=1.04 min; MS (ESIpos): m/z=428 [M+H]$^+$.

Example 38A 5-(3-Bromo-5-trifluoromethoxyphenyl)-1-(6-chloropyridin-2-yl)-1H-pyrazole-3-carboxylic acid

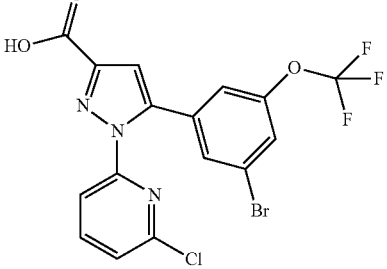

1.10 g (2.40 mmol) of the compound of Example 5A is reacted analogously to the synthesis of the compound of Example 20A with 518 mg (3.61 mmol) of 6-chloropyridin-2-yl-hydrazine. After hydrolysis, 737 mg (66% of theory) of the title compound is obtained.

$^1$H-NMR (400 MHz, DMSO-d$_6$): δ=7.27 (s, 1H), 7.29 (s, 1H), 7.60 (d, 1H), 7.73-7.79 (m, 2H), 7.85 (d, 1H), 8.13 (t, 1H), 13.31 (bs, 1H).

LC-MS (Method 1): R$_t$=1.14 min; MS (ESIpos): m/z=462 [M+H]$^+$.

Example 39A 5-(3-Bromo-5-trifluoromethoxyphenyl)-1-(pyridin-3-yl)-1H-pyrazole-3-carboxylic acid

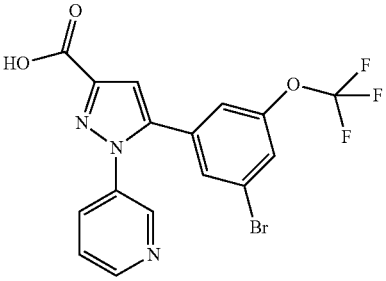 [SMILES: O=C(O)c1cc(-c2cc(Br)cc(OC(F)(F)F)c2)n(-c2cccnc2)n1]

600 mg (1.39 mmol) of the compound of Example 5A is reacted analogously to the synthesis of the compound of Example 20A with 303 mg (2.08 mmol) of 3-pyridylhydrazine hydrochloride. After hydrolysis, 355 mg (60% of theory) of the title compound is obtained.

$^1$H-NMR (400 MHz, DMSO-d$_6$): δ=7.20 (s, 1H), 7.34 (s, 1H), 7.55 (dd, 1H), 7.69-7.75 (m, 2H), 7.86 (dt, 1H), 8.59 (d, 1H), 8.67 (dd, 1H), 13.18 (bs, 1H).

LC-MS (Method 1): R$_t$=0.94 min; MS (ESIpos): m/z=428 [M+H]$^+$.

Example 40A 5-(3-Bromo-5-trifluoromethoxyphenyl)-1-(6-chloropyridin-3-yl)-1H-pyrazole-3-carboxylic acid

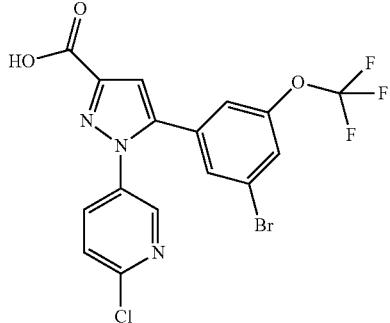 [SMILES: O=C(O)c1cc(-c2cc(Br)cc(OC(F)(F)F)c2)n(-c2ccc(Cl)nc2)n1]

280 mg (0.72 mmol) of the compound of Example 5A is reacted analogously to the synthesis of the compound of Example 20A with 171 mg (0.79 mmol) of 6-chloropyridin-3-yl-hydrazine dihydrochloride. After hydrolysis, 202 mg (61% of theory) of the title compound is obtained.

$^1$H-NMR (400 MHz, DMSO-d$_6$): δ=7.24 (s, 1H), 7.33 (s, 1H), 7.68 (d, 1H), 7.73-7.78 (m, 1H), 7.91 (dd, 1H), 8.28 (s, 1H), 8.46 (d, 1H), 13.23 (bs, 1H).

LC-MS (Method 1): R$_t$=1.07 min; MS (ESIpos): m/z=462 [M+H]$^+$.

Example 41A 5-(3-Bromo-5-trifluoromethoxyphenyl)-1-(6-methylpyridin-3-yl)-1H-pyrazole-3-carboxylic acid

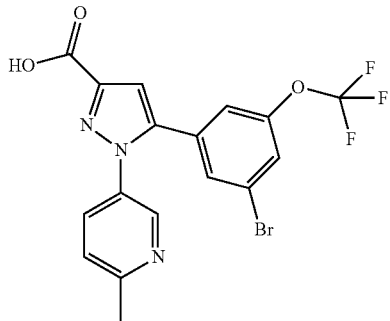 [SMILES: Cc1ccc(-n2nc(C(=O)O)cc2-c2cc(Br)cc(OC(F)(F)F)c2)cn1]

656 g (1.35 mmol) of the compound of Example 5A is reacted analogously to the synthesis of the compound of Example 20A with 359 mg (2.02 mmol) of 6-methylpyridin-3-yl-hydrazine hydrochloride. After hydrolysis, 53 mg (9% of theory) of the title compound is obtained.

$^1$H-NMR (400 MHz, DMSO-d$_6$): δ=2.52 (s, 3H), 7.18 (s, 1H), 7.31 (s, 1H), 7.39 (d, 1H), 7.69-7.76 (m, 3H), 8.43 (d, 1H), 13.15 (bs, 1H).

LC-MS (Method 1): R$_t$=1.02 min; MS (ESIpos): m/z=4432 [M+H]$^+$.

Example 42A 5-(3-Bromo-5-trifluoromethoxyphenyl)-1-(6-fluoropyridin-3-yl)-1H-pyrazole-3-carboxylic acid

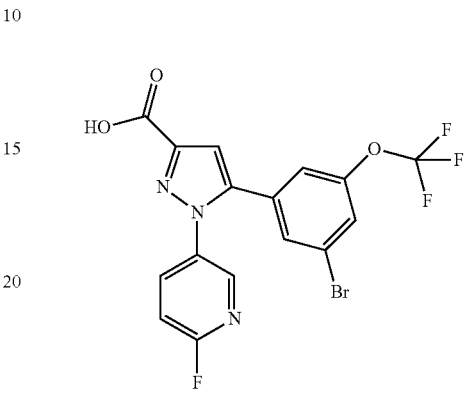

500 mg (1.16 mmol) of the compound of Example 5A is reacted analogously to the synthesis of the compound of Example 20A with 284 mg (1.74 mmol) of 6-fluoropyridin-3-yl-hydrazine hydrochloride. After hydrolysis, 256 mg (49% of theory) of the title compound is obtained.

$^1$H-NMR (400 MHz, DMSO-d$_6$): δ=7.21 (s, 1H), 7.34 (s, 1H), 7.37 (dd, 1H), 7.72-7.78 (m, 2H), 8.04-8.12 (m, 1H), 8.31 (d, 1H), 13.21 (bs, 1H).

LC-MS (Method 1): R$_t$=1.03 min; MS (ESIpos): m/z=446 [M+H]$^+$.

Example 43A 5-(3-Bromo-5-trifluoromethoxyphenyl)-1-(5-chloropyridin-3-yl)-1H-pyrazole-3-carboxylic acid

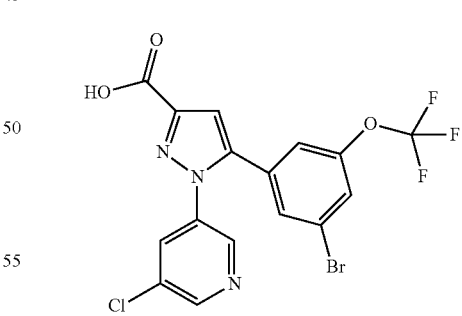

656 g (1.35 mmol) of the compound of Example 5A is reacted analogously to the synthesis of the compound of Example 20A with 364 mg (2.02 mmol) of 5-chloropyridin-3-yl-hydrazine hydrochloride. After hydrolysis, 278 mg (45% of theory) of the title compound is obtained.

$^1$H-NMR (400 MHz, DMSO-d$_6$): δ=7.24 (dt, 1H), 7.35 (s, 1H), 7.77 (d, 2H), 8.12 (t, 1H), 8.54 (d, 1H), 8.76 (d, 1H), 13.25 (bs, 1H).

Example 44A 5-(3-Bromo-5-trifluoromethoxyphenyl)-1-(5-fluoro-pyridin-3-yl)-1H-pyrazole-3-carboxylic acid

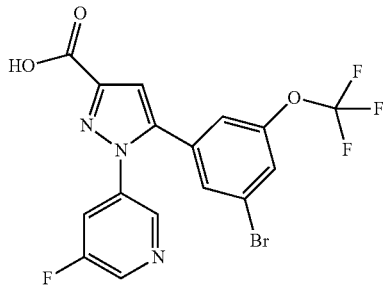 [SMILES: O=C(O)c1cc(-c2cc(Br)cc(OC(F)(F)F)c2)n(-c2cncc(F)c2)n1]

500 mg (1.16 mmol) of the compound of Example 5A is reacted analogously to the synthesis of the compound of Example 20A with 265 mg (1.62 mmol) of 5-fluoropyridin-3-yl-hydrazine hydrochloride. After hydrolysis, 340 mg (66% of theory) of the title compound is obtained.

$^1$H-NMR (400 MHz, DMSO-$d_6$): δ=7.23 (s, 1H), 7.36 (s, 1H), 7.74-7.79 (md, 2H), 7.97 (dt, 1H), 8.47 (s, 1H), 8.74 (d, 1H), 13.26 (bs, 1H).

LC-MS (Method 1): $R_t$=1.01 min; MS (ESIpos): m/z=446 [M+H]$^+$.

Example 45A 5-(3-Bromo-5-trifluoromethoxyphenyl)-1-(pyridin-4-yl)-1H-pyrazole-3-carboxylic acid

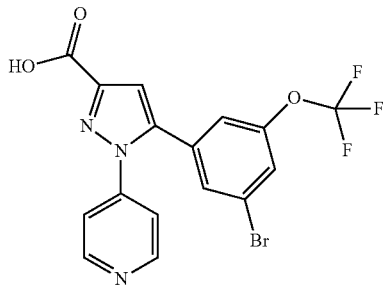 [SMILES: O=C(O)c1cc(-c2cc(Br)cc(OC(F)(F)F)c2)n(-c2ccncc2)n1]

1.10 g (2.40 mmol) of the compound of Example 5A is reacted analogously to the synthesis of the compound of Example 20A with 656 mg (3.61 mmol) of 4-pyridylhydrazine dihydrochloride. After hydrolysis, 23 mg (2% of theory) of the title compound is obtained.

$^1$H-NMR (400 MHz, DMSO-$d_6$): δ=7.25 (s, 1H), 7.32 (s, 1H), 7.36-7.39 (m, 2H), 7.74-7.80 (m, 2H), 8.65-8.69 (m, 2H), 13.27 (bs, 1H).

Example 46A 5-(3-Bromo-5-trifluoromethoxyphenyl)-1-(2-chloro-pyridin-4-yl)-1H-pyrazole-3-carboxylic acid

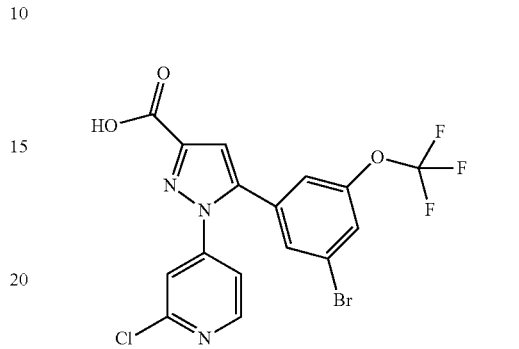

690 mg (1.77 mmol) of the compound of Example 5A is reacted analogously to the synthesis of the compound of Example 20A with 350 mg (1.94 mmol) of 2-chloropyridin-4-yl-hydrazine hydrochloride. After hydrolysis, 475 mg (58% of theory) of the title compound is obtained.

$^1$H-NMR (400 MHz, DMSO-$d_6$): δ=7.33 (s, 2H), 7.36 (s, 1H), 7.53 (s, 1H), 7.82 (s, 2H), 8.49 (d, 1H), 13.37 (bs, 1H).

LC-MS (Method 1): $R_t$=1.10 min; MS (ESIpos): m/z=462 [M+H]$^+$.

Example 47A 5-(3-Bromo-5-trifluoromethoxyphenyl)-1-(2-trifluoromethylpyridin-4-yl)-1H-pyrazole-3-carboxylic acid

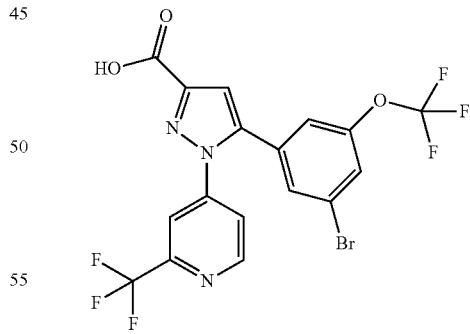

500 mg (1.16 mmol) of the compound of Example 5A is reacted analogously to the synthesis of the compound of Example 20A with 370 mg (1.74 mmol) of 2-trifluoromethylpyridin-4-yl-hydrazine hydrochloride. After hydrolysis, 307 mg (53% of theory) of the title compound is obtained.

$^1$H-NMR (400 MHz, DMSO-$d_6$): δ=7.34 (s, 1H), 7.35 (s, 1H), 7.70 (dd, 1H), 7.79 (d, 1H), 7.81-7.86 (m, 2H), 8.85 (d, 1H), 13.40 (bs, 1H).

LC-MS (Method 3): $R_t$=1.17 min; MS (ESIpos): m/z=496 [M+H]$^+$.

Example 48A 5-(3-Bromo-5-trifluoromethoxyphenyl)-1-(2-methylpyridin-4-yl)-1H-pyrazole-3-carboxylic acid

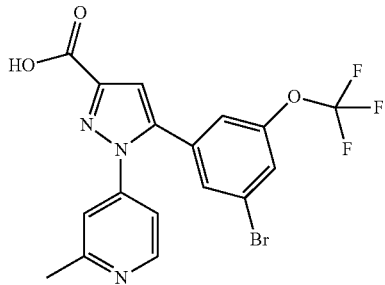 [SMILES: Cc1cc(-n2nc(C(=O)O)cc2-c2cc(Br)cc(OC(F)(F)F)c2)ccn1]

500 mg (1.03 mmol) of the compound of Example 5A is reacted analogously to the synthesis of the compound of Example 20A with 315 mg (1.54 mmol) of 2-methylpyridin-4-yl-hydrazine hydrobromide. After hydrolysis, 182 mg (40% of theory) of the title compound is obtained.

$^1$H-NMR (400 MHz, DMSO-d$_6$): δ=2.47 (s, 3H), 7.10 (dd, 1H), 7.22 (s, 1H), 7.32 (s, 2H), 7.75-7.81 (m, 2H), 8.50 (d, 1H), 13.24 (bs, 1H).

LC-MS (Method 3): $R_t$=0.94 min; MS (ESIpos): m/z=442 [M+H]$^+$.

Example 49A 5-(3-Bromo-5-trifluoromethoxyphenyl)-1-(2-methoxypyridin-4-yl)-1H-pyrazole-3-carboxylic acid

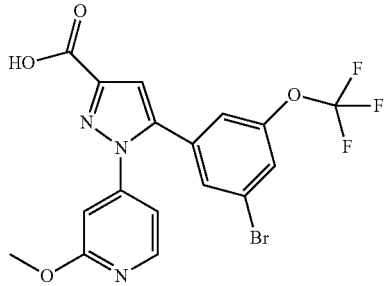 [SMILES: COc1cc(-n2nc(C(=O)O)cc2-c2cc(Br)cc(OC(F)(F)F)c2)ccn1]

500 mg (1.16 mmol) of the compound of Example 5A is reacted analogously to the synthesis of the compound of Example 20A with 305 mg (1.74 mmol) of 2-methoxypyridin-4-yl-hydrazine hydrochloride. After hydrolysis, 18 mg (3% of theory) of the title compound is obtained.

LC-MS (Method 2): $R_t$=2.38 min; MS (ESIpos): m/z=458 [M+H]$^+$.

Example 50A 5-(3-Bromo-5-methoxyphenyl)-1-(pyridin-3-yl)-1H-pyrazole-3-carboxylic acid

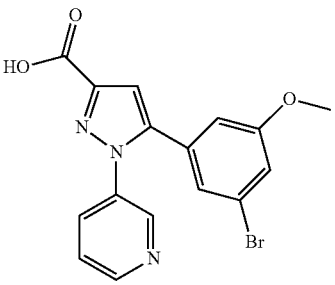 [SMILES: COc1cc(Br)cc(-c2cc(C(=O)O)nn2-c2cccnc2)c1]

500 mg (1.19 mmol) of the compound of Example 6A is reacted analogously to the synthesis of the compound of Example 20A with 260 mg (1.79 mmol) of 3-pyridylhydrazine hydrochloride. After hydrolysis, 240 mg (54% of theory) of the title compound is obtained.

$^1$H-NMR (400 MHz, DMSO-d$_6$): δ=3.69 (s, 3H), 6.84 (t, 1H), 7.04 (t, 1H), 7.19 (t, 1H), 7.22 (s, 1H), 7.55 (dd, 1H), 7.83-7.88 (m, 1H), 8.57 (d, 1H), 8.66 (dd, 1H), 13.14 (bs, 1H).

LC-MS (Method 2): $R_t$=1.95 min; MS (ESIpos): m/z=374 [M+H]$^+$.

Example 51A 5-(3-Bromo-5-methoxyphenyl)-1-(2-chloropyridin-4-yl)-1H-pyrazole-3-carboxylic acid

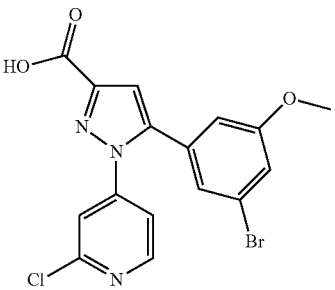 [SMILES: COc1cc(Br)cc(-c2cc(C(=O)O)nn2-c2ccnc(Cl)c2)c1]

500 mg (1.19 mmol) of the compound of Example 6A is reacted analogously to the synthesis of the compound of Example 20A with 322 mg (1.79 mmol) of 2-chloropyridin-4-yl-hydrazine hydrochloride. After hydrolysis, 259 mg (53% of theory) of the title compound is obtained.

$^1$H-NMR (400 MHz, DMSO-d$_6$): δ=3.74 (s, 3H), 6.97 (s, 1H), 7.15 (s, 1H), 7.20 (s, 1H), 7.27 (t, 1H), 7.31 (dd, 1H), 7.55 (d, 1H), 8.47 (d, 1H), 13.27 (bs, 1H).

Example 52A 5-(3-Fluoro-5-difluoromethoxyphenyl)-1-(pyridin-3-yl)-1H-pyrazole-3-carboxylic acid

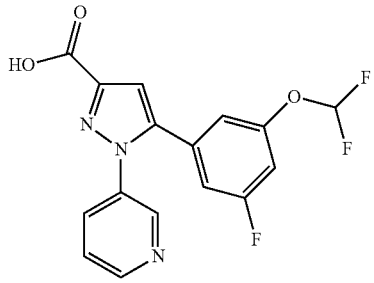 [SMILES: O=C(O)c1cc(-c2cc(F)cc(OC(F)F)c2)n(-c2cccnc2)n1]

590 mg (1.01 mmol) of the compound of Example 7A is reacted analogously to the synthesis of the compound of Example 20A with 161 mg (1.11 mmol) of 3-pyridylhydrazine hydrochloride. After hydrolysis, 150 mg (43% of theory) of the title compound is obtained.

$^1$H-NMR (400 MHz, DMSO-d$_6$): δ=6.96 (s, 1H), 7.05-7.11 (m, 1H), 7.21 (dt, 1H), 7.25 (t, 1H), 7.27 (s, 1H), 7.55 (dd, 1H), 7.83-7.89 (m, 1H), 8.58 (d, 1H), 8.66 (dd, 1H), 13.19 (bs, 1H).

LC-MS (Method 3): R$_t$=0.83 min; MS (ESIpos): m/z=350 [M+H]$^+$.

Example 53A 5-(3-Fluoro-5-difluoromethoxyphenyl)-1-(2-chloropyridin-4-yl)-1H-pyrazole-3-carboxylic acid

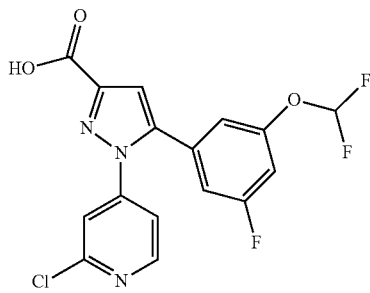 [SMILES: O=C(O)c1cc(-c2cc(F)cc(OC(F)F)c2)n(-c2ccnc(Cl)c2)n1]

590 mg (1.01 mmol) of the compound of Example 7A is reacted analogously to the synthesis of the compound of Example 20A with 200 mg (1.11 mmol) of 2-chloropyridin-4-yl-hydrazine hydrochloride. After hydrolysis, 160 mg (41% of theory) of the title compound is obtained.

$^1$H-NMR (400 MHz, DMSO-d$_6$): δ=7.07 (s, 1H), 7.11, 7.19-7.34, 7.47 (s, m, s, 5H), 7.56 (d, 1H), 8.48 (d, 1H), 13.359 (bs, 1H).

LC-MS (Method 3): R$_t$=0.95 min; MS (ESIpos): m/z=384 [M+H]$^+$.

Example 54A 5-(3-Chloro-5-difluoromethoxyphenyl)-1-(pyridin-3-yl)-1H-pyrazole-3-carboxylic acid

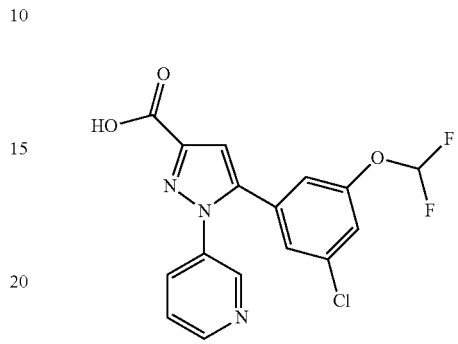

350 mg (0.80 mmol) of the compound of Example 8A is reacted analogously to the synthesis of the compound of Example 20A with 128 mg (0.88 mmol) of 3-pyridylhydrazine hydrochloride. After hydrolysis, 176 mg (60% of theory) of the title compound is obtained.

$^1$H-NMR (400 MHz, DMSO-d$_6$): δ=7.06-7.09 (m, 1H), 7.25 (t, 1H), 7.26-7.30 (m, 2H), 7.38 (t, 1H), 7.55 (dd, 1H), 7.84-7.89 (m, 1H), 8.59 (d, 1H), 8.67 (dd, 1H), 13.18 (bs, 1H).

LC-MS (Method 1): R$_t$=0.85 min; MS (ESIpos): m/z=366 [M+H]$^+$.

Example 55A 5-(3-Bromo-5-difluoromethoxyphenyl)-1-(pyridin-3-yl)-1H-pyrazole-3-carboxylic acid

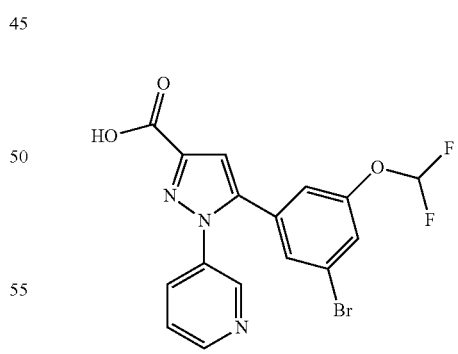

247 mg (0.67 mmol) of the compound of Example 9A is reacted analogously to the synthesis of the compound of Example 20A with 145 mg (1.00 mmol) of 3-pyridylhydrazine hydrochloride. After hydrolysis, 51 mg (19% of theory) of the title compound is obtained.

$^1$H-NMR (400 MHz, DMSO-d$_6$): δ=7.11 (s, 1H), 7.25 (t, 1H), 7.29 (s, 1H), 7.39 (t, 1H), 7.49 (t, 1H), 7.56 (dd, 1H), 7.83-7.89 (m, 1H), 8.58 (d, 1H), 8.67 (dd, 1H), 13.17 (bs, 1H).

Example 56A 5-(3-Methoxy-5-trifluoromethoxyphenyl)-1-(pyridin-3-yl)-1H-pyrazole-3-carboxylic acid

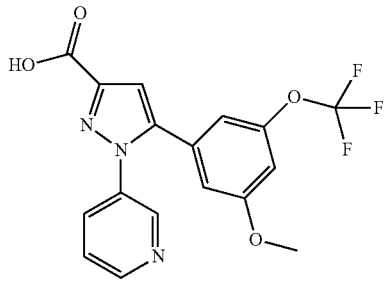 [SMILES: COc1cc(OC(F)(F)F)cc(-c2cc(C(=O)O)nn2-c2cccnc2)c1]

500 mg (1.29 mmol) of the compound of Example 10A is reacted analogously to the synthesis of the compound of Example 20A with 207 mg (1.42 mmol) of 3-pyridylhydrazine hydrochloride. After hydrolysis, 248 mg (51% of theory) of the title compound is obtained.

$^1$H-NMR (400 MHz, DMSO-$d_6$): δ=3.76 (s, 3H), 6.70 (s, 1H), 6.98 (s, 1H), 7.02 (s, 1H), 7.27 (s, 1H), 7.54 (dd, 1H), 7.83-7.88 (m, 1H), 8.56 (d, 1H), 8.65 (m, 1H), 13.15 (bs, 1H).

LC-MS (Method 2): $R_t$=2.05 min; MS (ESIpos): m/z=380 [M+H]$^+$.

Example 57A 5-(3-Methoxy-5-trifluoromethoxyphenyl)-1-(2-chloropyridin-4-yl)-1H-pyrazole-3-carboxylic acid

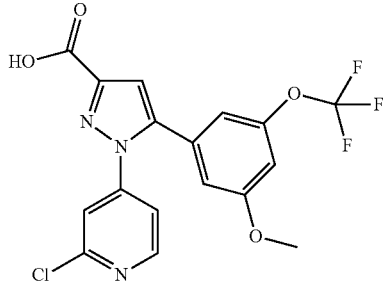 [SMILES: COc1cc(OC(F)(F)F)cc(-c2cc(C(=O)O)nn2-c2ccnc(Cl)c2)c1]

500 mg (1.29 mmol) of the compound of Example 10A is reacted analogously to the synthesis of the compound of Example 20A with 256 mg (1.42 mmol) of 2-chloropyridin-4-yl-hydrazine hydrochloride. After hydrolysis, 149 mg (28% of theory) of the title compound is obtained.

$^1$H-NMR (400 MHz, DMSO-$d_6$): δ=3.81 (s, 3H), 6.81 (s, 1H), 7.06 (s, 1H), 7.14 (s, 1H), 7.27 (s, 1H), 7.35 (dd, 1H), 7.50 (d, 1H), 8.48 (d, 1H), 13.32 (bs, 1H).

LC-MS (Method 1): $R_t$=0.87 min; MS (ESIpos): m/z=410 [M+H]$^+$.

Example 58A 5-(3-Cyano-5-trifluoromethoxyphenyl)-1-(pyridin-3-yl)-1H-pyrazole-3-carboxylic acid

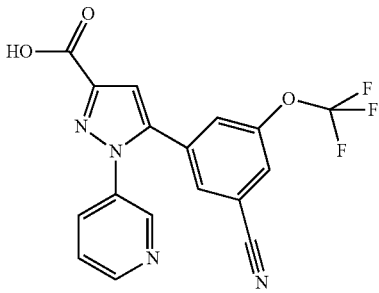 [SMILES: N#Cc1cc(OC(F)(F)F)cc(-c2cc(C(=O)O)nn2-c2cccnc2)c1]

300 mg (0.81 mmol) of the compound of Example 11A is reacted analogously to the synthesis of the compound of Example 20A with 175 mg (1.21 mmol) of 3-pyridylhydrazine hydrochloride. After hydrolysis, 148 mg (49% of theory) of the title compound is obtained.

$^1$H-NMR (400 MHz, DMSO-$d_6$): δ=7.38 (s, 1H), 7.49-7.57 (m, 2H), 7.83-7.88 (m, 1H), 8.04 (t, 1H), 8.08 (s, 1H), 8.59 (d, 1H), 8.67 (dd, 1H), 13.22 (bs, 1H).

LC-MS (Method 2): $R_t$=1.91 min; MS (ESIpos): m/z=375 [M+H]$^+$.

Example 59A 5-(3-Fluoro-5-[2,2,2]-trifluoroethoxyphenyl)-1-(pyridin-3-yl)-1H-pyrazole-3-carboxylic acid

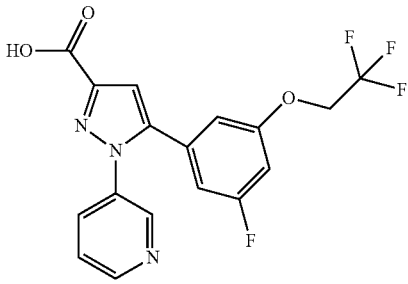 [SMILES: O=C(O)c1cc(-c2cc(F)cc(OCC(F)(F)F)c2)n(-c2cccnc2)n1]

500 mg (1.32 mmol) of the compound of Example 12A is reacted analogously to the synthesis of the compound of Example 20A with 287 mg (1.97 mmol) of 3-pyridylhydrazine hydrochloride. After hydrolysis, 398 mg (79% of theory) of the title compound is obtained.

$^1$H-NMR (400 MHz, DMSO-$d_6$): δ=4.79 (q, 2H), 6.77 (d, 1H), 6.94 (s, 1H), 7.08 (dt, 1H), 7.23 (s, 1H), 7.55 (dd, 1H), 7.82-7.88 (m, 1H), 8.56 (d, 1H), 8.65 (d, 1H), 13.16 (bs, 1H).

LC-MS (Method 1): $R_t$=1.01 min; MS (ESIpos): m/z=414 [M+H]$^+$.

Example 60A 1-(3-Chloro-4-fluorophenyl)-5-(5-fluoropyridin-3-yl)-1H-pyrazole-3-carboxylic acid

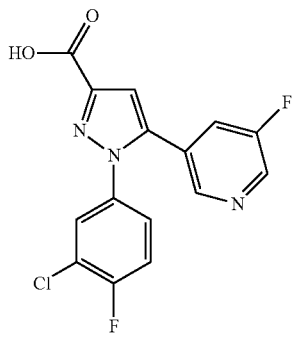 [SMILES: O=C(O)c1cc(-c2cncc(F)c2)n(-c2ccc(F)c(Cl)c2)n1]

1.42 g (4.33 mmol) of the compound of Example 13A is reacted analogously to the synthesis of the compound of Example 20A with 1.28 g (6.50 mmol) of 3-chloro-4-fluorophenylhydrazine hydrochloride. After hydrolysis, 854 mg (59% of theory) of the title compound is obtained.

$^1$H-NMR (400 MHz, DMSO-$d_6$): δ=7.31 (s, 1H), 7.36-7.42 (m, 1H), 7.54 (t, 1H), 7.75 (dt, 1H), 7.79 (dd, 1H), 8.36 (s, 1H), 8.62 (d, 1H), 13.19 (bs, 1H).

LC-MS (Method 1): $R_t$=0.82 min; MS (ESIpos): m/z=336 [M+H]$^+$.

Example 61A 1-(3-Chloro-4-fluorophenyl)-5-(5-chloropyridin-3-yl)-1H-pyrazole-3-carboxylic acid

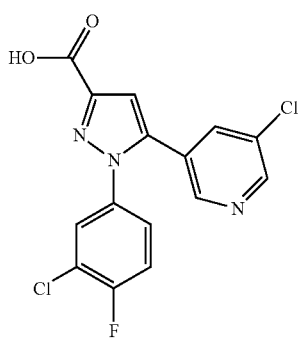 [SMILES: O=C(O)c1cc(-c2cncc(Cl)c2)n(-c2ccc(F)c(Cl)c2)n1]

1.70 g (4.24 mmol) of the compound of Example 14A is reacted analogously to the synthesis of the compound of Example 20A with 1.25 g (6.36 mmol) of 3-chloro-4-fluorophenylhydrazine hydrochloride. After hydrolysis, 896 mg (60% of theory) of the title compound is obtained.

$^1$H-NMR (400 MHz, DMSO-$d_6$): δ=7.33 (s, 1H), 7.37-7.43 (m, 1H), 7.55 (t, 1H), 7.80 (dd, 1H), 7.94 (t, 1H), 8.42 (d, 1H), 8.65 (d, 1H), 13.18 (bs, 1H).

LC-MS (Method 1): $R_t$=0.89 min; MS (ESIpos): m/z=352 [M+H]$^+$.

Example 62A 1-(3-Chloro-4-fluorophenyl)-5-(5-chloro-6-fluoropyridin-3-yl)-1H-pyrazole-3-carboxylic acid

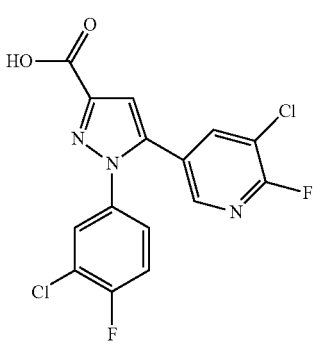 [SMILES: O=C(O)c1cc(-c2cnc(F)c(Cl)c2)n(-c2ccc(F)c(Cl)c2)n1]

240 mg (0.86 mmol) of the compound of Example 15A is reacted analogously to the synthesis of the compound of Example 20A with 253 mg (1.29 mmol) of 3-chloro-4-fluorophenylhydrazine hydrochloride. After hydrolysis, 16 mg (5% of theory) of the title compound is obtained.

LC-MS (Method 1): $R_t$=1.02 min; MS (ESIpos): m/z=370 [M+H]$^+$.

Example 63A 1-(3-Chlorophenyl)-5-(5-chloro-6-fluoropyridin-3-yl)-1H-pyrazole-3-carboxylic acid

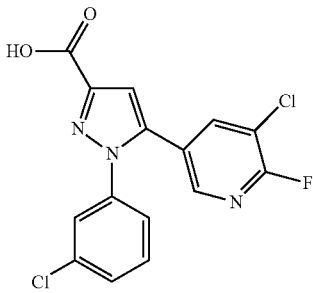 [SMILES: O=C(O)c1cc(-c2cnc(F)c(Cl)c2)n(-c2cccc(Cl)c2)n1]

240 mg (0.86 mmol) of the compound of Example 15A is reacted analogously to the synthesis of the compound of Example 20A with 230 mg (1.29 mmol) of 3-chlorophenylhydrazine hydrochloride. After hydrolysis, 21 mg (7% of theory) of the title compound is obtained.

LC-MS (Method 1): R$_t$1=0.96 min; MS (ESIpos): m/z=352 [M+H]$^+$.

Example 64A 1-(3-Chloro-4-fluorophenyl)-5-(5-methoxypyridin-3-yl)-1H-pyrazole-3-carboxylic acid

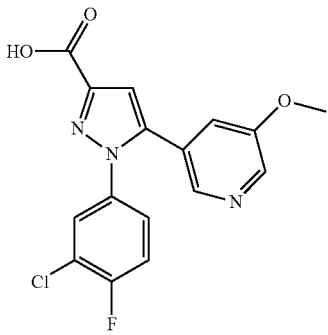 [SMILES: COc1cncc(-c2cc(C(=O)O)nn2-c2ccc(F)c(Cl)c2)c1]

600 mg (1.33 mmol) of the compound of Example 16A is reacted analogously to the synthesis of the compound of Example 20A with 288 mg (1.46 mmol) of 3-chloro-4-fluorophenylhydrazine hydrochloride. After hydrolysis, the entire reaction mixture is reduced to the dry state i. vac. 712 mg (37% purity, 57% of theory) of the title compound, which is used without further purification, is obtained.

LC-MS (Method 1): R$_t$=0.80 min; MS (ESIpos): m/z=348 [M+H]$^+$.

Example 65A 1-(3-Chloro-4-fluorophenyl)-5-(5-difluoromethoxypyridin-3-yl)-1H-pyrazole-3-carboxylic acid

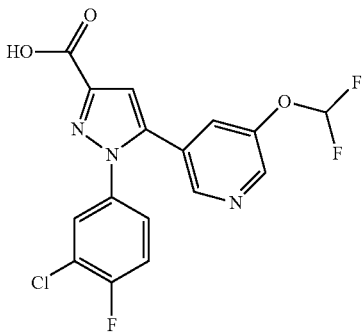 [SMILES: O=C(O)c1cc(-c2cncc(OC(F)F)c2)n(-c2ccc(F)c(Cl)c2)n1]

220 mg (0.64 mmol) of the compound of Example 17A is reacted analogously to the synthesis of the compound of Example 20A with 188 mg (0.96 mmol) of 3-chloro-4-fluorophenylhydrazine hydrochloride. After hydrolysis, 120 mg (49% of theory) of the title compound is obtained.

$^1$H-NMR (400 MHz, DMSO-d$_6$): δ=7.29 (t, 1H), 7.33 (s, 1H), 7.37-7.43 (m, 1H), 7.47, 7.51-7.59 (s, m, 2H), 7.80 (dd, 1H), 8.42 (d, 1H), 8.51 (d, 1H), 13.19 (bs, 1H).

LC-MS (Method 1): R$_t$=0.92 min; MS (ESIpos): m/z=384 [M+H]$^+$.

Example 66A 1-(3-Chloro-4-fluorophenyl)-5-(5-trifluoromethoxypyridin-3-yl)-1H-pyrazole-3-carboxylic acid

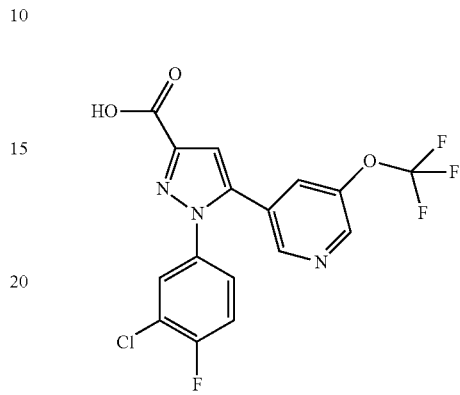

1.13 g (3.25 mmol) of the compound of Example 18A is reacted analogously to the synthesis of the compound of Example 20A with 961 mg (4.88 mmol) of 3-chloro-4-fluorophenylhydrazine hydrochloride. After hydrolysis, 576 mg (44% of theory) of the title compound is obtained.

$^1$H-NMR (400 MHz, DMSO-ds): δ=7.39-7.45 (m, 2H), 7.55 (t, 1H), 7.82 (dd, 1H), 8.11 (s, 1H), 8.81 (d, 1H), 8.99 (s, 1H), 13.19 (bs, 1H).

LC-MS (Method 1): R$_t$=0.93 min; MS (ESIpos): m/z=386 [M+H]$^+$.

Example 67A 1-(3-Chlorophenyl)-5-(5-trifluoromethoxypyridin-3-yl)-1H-pyrazole-3-carboxylic acid

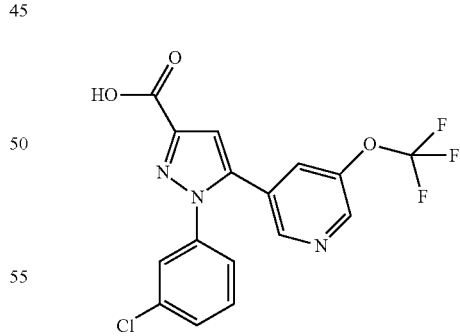

1.13 g (3.25 mmol) of the compound of Example 18A is reacted analogously to the synthesis of the compound of Example 20A with 874 mg (4.88 mmol) of 3-chlorophenylhydrazine hydrochloride. After hydrolysis, 609 mg (49% of theory) of the title compound is obtained.

$^1$H-NMR (400 MHz, DMSO-d$_6$): δ=7.33 (d, 1H), 7.43 (s, 1H), 7.49 (t, 1H), 7.55-7.63 (m, 2H), 8.08 (s, 1H), 8.81 (d, 1H), 8.99 (s, 1H), 13.19 (bs, 1H).

LC-MS (Method 1): $R_t$=0.92 min; MS (ESIpos): m/z=368 [M+H]$^+$.

Example 68A 1-(3-Chloro-4-fluorophenyl)-5-(2-chloropyridin-4-yl)-1H-pyrazole-3-carboxylic acid

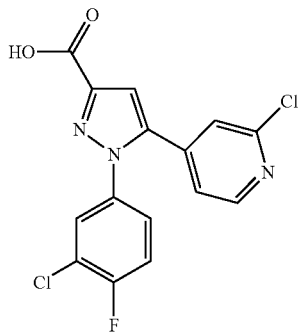 [SMILES: O=C(O)c1cc(-c2ccnc(Cl)c2)n(-c2ccc(F)c(Cl)c2)n1]

560 mg (2.14 mmol) of the compound of Example 19A is reacted analogously to the synthesis of the compound of Example 20A with 464 mg (2.36 mmol) of 3-chloro-4-fluorophenylhydrazine hydrochloride. After hydrolysis, 488 mg (65% of theory) of the title compound is obtained.

$^1$H-NMR (400 MHz, DMSO-d$_6$): δ=7.18 (dd, 1H), 7.30 (s, 1H), 7.35-7.40 (m, 1H), 7.50-7.59 (m, 2H), 7.81 (dd, 1H), 8.38 (d, 1H). COOH, undetectable.

LC-MS (Method 1): $R_t$=0.93 min; MS (ESIpos): m/z=352 [M+H]$^+$.

Example 69A 1-(3-Chlorophenyl)-5-(2-chloropyridin-4-yl)-1H-pyrazole-3-carboxylic acid

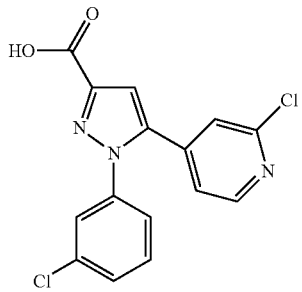 [SMILES: O=C(O)c1cc(-c2ccnc(Cl)c2)n(-c2cccc(Cl)c2)n1]

560 mg (2.14 mmol) of the compound of Example 19A is reacted analogously to the synthesis of the compound of Example 20A with 422 mg (2.36 mmol) of 3-chlorophenylhydrazine hydrochloride. After hydrolysis, 494 mg (69% of theory) of the title compound is obtained.

$^1$H-NMR (400 MHz, DMSO-d$_6$): δ=7.21 (dd, 1H), 7.30-7.35 (m, 1H), 7.42 (s, 1H), 7.49-7.55 (m, 2H), 7.58-7.64 (m, 2H), 8.40 (d, 1H), 13.22 (bs, 1H).

LC-MS (Method 1): $R_t$=0.92 min; MS (ESIpos): m/z=334 [M+H]$^+$.

EMBODIMENTS

Example 1

1-{[5-(3-Chloro-5-fluorophenyl)-1-(pyridin-2-yl)-1H-pyrazol-3-yl]carbonyl}imidazolidin-4-one

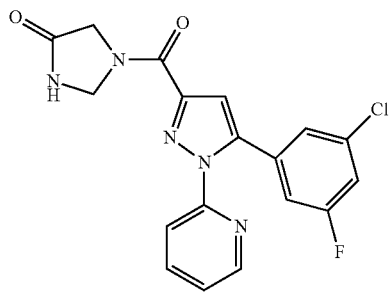 [SMILES: O=C1CN(C(=O)c2cc(-c3cc(F)cc(Cl)c3)n(-c3ccccn3)n2)CN1]

0.12 ml (0.71 mmol) of N,N-diisopropylethylamine as well as 0.5 ml of DMF are added to a solution of 75 mg (0.24 mmol) of the compound of Example 20A, 32 mg (0.26 mmol) of 4-imidazolinone-hydrochloride, and 126 mg (0.33 mmol) of HATU in 1 ml of THF, and the mixture that is obtained is stirred for 16 hours at room temperature. The reaction mixture is diluted with acetonitrile, filtered over a Millipore spray filter, and separated by means of preparative HPLC (mobile solvent: acetonitrile/water gradient). 71 mg (78% of theory) of the title compound is obtained.

$^1$H-NMR (400 MHz, DMSO-d$_6$): δ=3.99/4.47 (s, 2H each), 4.91/5.36 (s, 2H each), 7.13-7.29 (m, 3H), 7.43-7.55 (m, 2H), 7.89 (dd, 1H), 8.07-8.17 (m, 1H), 8.35 (s, 1H), 8.67/8.74 (s, 1H each).

LC-MS (Method 1): $R_t$=0.84 min; MS (ESIpos): m/z=386 [M+H]$^+$.

Example 2

1-{[5-(3-Chloro-5-fluorophenyl)-1-(6-chloropyridin-2-yl)-1H-pyrazol-3-yl]carbonyl}imidazolidin-4-one

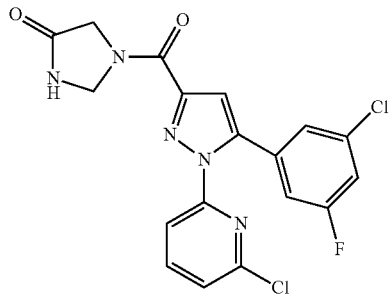 [SMILES: O=C1CN(C(=O)c2cc(-c3cc(F)cc(Cl)c3)n(-c3cccc(Cl)n3)n2)CN1]

75 mg (0.21 mmol) of the compound of Example 21A is reacted analogously to the synthesis of the compound of Example 1 with 29 mg (0.23 mmol) of 4-imidazolinone-hydrochloride. 44 mg (49% of theory) of the title compound is obtained.

$^1$H-NMR (400 MHz, DMSO-d$_6$): δ=4.00/4.48 (s, 2H each), 4.91/5.36 (s, 2H each), 7.20-7.38 (m, 3H), 7.53 (d, 1H), 7.60 (d, 1H), 7.92 (dd, 1H), 8.08-8.18 (m, 1H), 8.70/8.75 (s, 1H each).

LC-MS (Method 1): R$_t$=0.96 min; MS (ESIpos): m/z=420 [M+H]$^+$.

Example 3

1-{[5-(3-Chloro-5-fluorophenyl)-1-(pyridin-3-yl)-1H-pyrazol-3-yl]carbonyl}imidazolidin-4-one

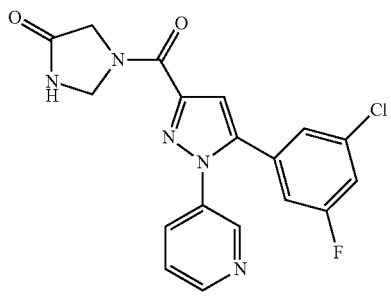 [SMILES: O=C1CN(C(=O)c2cc(-c3cc(F)cc(Cl)c3)n(-c3cccnc3)n2)CN1]

0.11 ml (0.64 mmol) of N,N-diisopropylethylamine is added to a solution of 75 mg (0.21 mmol, 90% purity) of the compound of Example 22A, 28 mg (0.23 mmol) of 4-imidazolinone-hydrochloride, and 113 mg (0.30 mmol) HATU in 2 ml of THF, and the mixture that is obtained is stirred for 3 hours at room temperature. The precipitate is filtered off, washed with some THF, and dried under high vacuum. 36 mg (44% of theory) of the title compound is obtained. The filtrate is separated by means of preparative HPLC (mobile solvent: acetonitrile/water gradient). Another 22 mg (27% of theory) of the title compound is obtained.

$^1$H-NMR (400 MHz, DMSO-d$_6$): δ=3.99/4.44 (s, 2H each), 4.91/5.33 (s, 2H each), 7.14-7.36 (m, 3H), 7.46-7.62 (m, 2H), 7.80-7.94 (m, 1H), 8.56-8.81 (m, 3H).

LC-MS (Method 1): R$_t$=0.84 min; MS (ESIpos): m/z=386 [M+H]$^+$.

Example 4

4-{[5-(3-Chloro-5-fluorophenyl)-1-(pyridin-3-yl)-1H-pyrazol-3-yl]carbonyl}piperazin-2-one

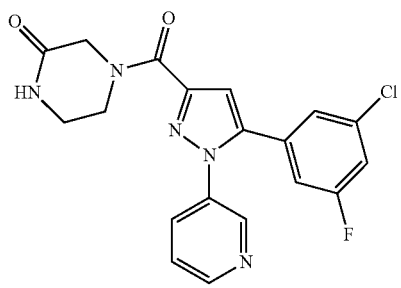 [SMILES: O=C1CN(C(=O)c2cc(-c3cc(F)cc(Cl)c3)n(-c3cccnc3)n2)CCN1]

0.07 ml (0.43 mmol) of N,N-diisopropylethylamine is added to a solution of 75 mg (0.21 mmol, 90% purity) of the compound of Example 22A, 23 mg (0.23 mmol) of 2-oxopiperazine, and 113 mg (0.30 mmol) of HATU in 2 ml of THF, and the mixture that is obtained is stirred for 3 hours at room temperature. The reaction mixture is separated by means of preparative HPLC (mobile solvent: acetonitrile/water gradient), and the title compound is obtained in a quantitative yield (87 mg).

$^1$H-NMR (400 MHz, DMSO-d$_6$): δ=3.24-3.37 (m, 1H), 3.78-3.87/4.09-4.19/4.51-4.58 (m, 5H each), 7.16-7.29 (m, 3H), 7.49-7.59 (m, 2H), 7.85 (d, 1H), 8.15 (s, 1H), 8.58-8.69 (m, 2H).

LC-MS (Method 1): R$_t$=0.82 min; MS (ESIpos): m/z=400 [M+H]$^+$.

Example 5

[5-(3-Chloro-5-fluorophenyl)-1-(pyridin-3-yl)-1H-pyrazol-3-yl](1,3-thiazolidin-3-yl)methanone

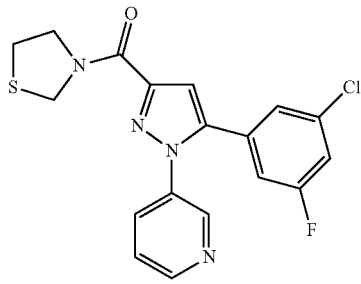 [SMILES: O=C(c1cc(-c2cc(F)cc(Cl)c2)n(-c2cccnc2)n1)N1CCSC1]

150 mg (0.43 mmol) of the compound of Example 22A is reacted analogously to the synthesis of the compound of Example 3 with 41 mg (0.46 mmol) of thiazolidine. After the crude product is purified by means of preparative HPLC (mobile solvent: acetonitrile/water gradient), 122 mg (74% of theory) of the title compound is obtained.

$^1$H-NMR (400 MHz, DMSO-d$_6$): δ=3.08 (t, 1H), 3.12 (t, 1H), 3.87 (t, 1H), 4.22 (t, 1H), 4.70 (s, 1H), 5.04 (s, 1H), 7.20 (d, 1H), 7.25 (d, 1H), 7.50-7.58 (m, 2H), 7.82-7.91 (m, 1H), 8.61-8.69 (m, 2H).

LC-MS (Method 1): R$_t$=0.98 min; MS (ESIpos): m/z=389 [M+H]$^+$.

Example 6

[5-(3-Chloro-5-fluorophenyl)-1-(pyridin-3-yl)-1H-pyrazol-3-yl](1-oxido-1,3-thiazolidin-3-yl)methanone (racemic)

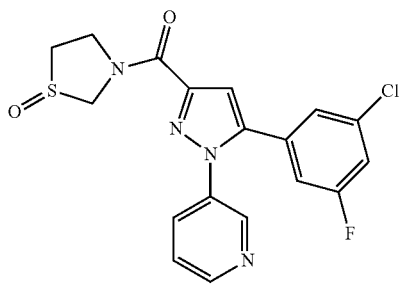 [SMILES: O=C(c1cc(-c2cc(F)cc(Cl)c2)n(-c2cccnc2)n1)N1CCS(=O)C1]

100 mg (0.26 mmol) of the compound of Example 5 is dissolved in 5 ml of dichloromethane, mixed with 63 mg (0.26 mmol, 70% purity) of meta-chloroperbenzoic acid, and stirred for 4 hours at room temperature. The reaction mixture is separated by means of preparative HPLC (mobile solvent: acetonitrile/water gradient). 97 mg (93% of theory) of the title compound is obtained.

¹H-NMR (400 MHz, DMSO-d): δ=2.99-3.38 (m, 2H), 3.99-4.09/4.25-4.37/4.39-4.52/4.57-4.70/4.96/5.46 (m, m, m, m, dd, dd, 4H), 7.18-7.32 (m, 3H), 7.50-7.59 (m, 2H), 7.85-7.93 (m, 1H), 8.63-8.71 (m, 2H).

LC-MS (Method 1): $R_t$=0.75 min; MS (ESIpos): m/z=405 [M+H]⁺.

By preparative HPLC in a chiral phase [Daicel Chiralpak AD-H, 5 μm, 250 mm×20 mm; eluant: isohexane/ethanol 25:75; flow: 15 ml/min; temperature: 45° C.; UV detection: 220 nm], the enantiomers are separated:

Enantiomer 6-1

$R_t$=7.13 min [Daicel Chiralpak AD-H, 5 μm, 250 mm×4.6 mm; eluant: isohexane/isopropanol/diethylamine 500:499:1; flow: 1 ml/min; temperature: 40° C.; UV detection: 220 nm];
$[α]_D^{20}$=+133.10, c=0.440, methanol;

Enantiomer 6-2

$R_t$=9.03 min [Daicel Chiralpak AD-H, 5 μm, 250 mm×4.6 mm; eluant: isohexane/isopropanol/diethylamine 500:499:1; flow: 1 ml/min; temperature: 40° C.; UV detection: 220 nm];
$[α]_D^{20}$=−130.10, c=0.420, methanol.

Example 7

1-{[5-(3-Chloro-5-fluorophenyl)-1-(6-chloropyridin-3-yl)-1H-pyrazol-3-yl]carbonyl}imidazolidin-4-one

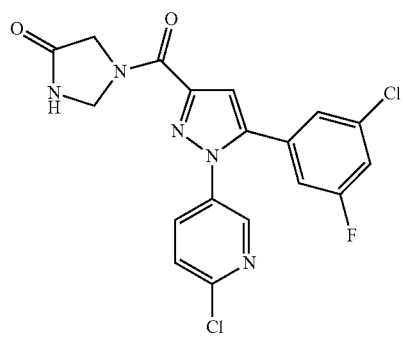 [SMILES: O=C1CN(C(=O)c2cc(-c3cc(F)cc(Cl)c3)n(-c3ccc(Cl)nc3)n2)CN1]

75 mg (0.18 mmol) of the compound of Example 23A is reacted analogously to the synthesis of the compound of Example 3 with 24 mg (0.24 mmol) of 4-imidazolinone-hydrochloride. The precipitate is filtered off, washed with some precipitate, and dried under high vacuum. 52 mg (65% of theory) of the title compound is obtained.

¹H-NMR (400 MI-Hz, DMSO-d₆): δ=3.99/4.44 (s, 2H each), 4.91/5.32 (s, 2H each), 7.21-7.38 (m, 3H), 7.56 (d, 1H), 7.69 (d, 1H), 7.87-7.98 (m, 1H), 8.52 (s, 1H), 8.63-8.78 (m, 1H).

LC-MS (Method 1): $R_t$=0.90 min; MS (ESIpos): m/z=420 [M+H]⁺.

Example 8

4-{[5-(3-Chloro-5-fluorophenyl)-1-(6-chloropyridin-3-yl)-1H-pyrazol-3-yl]carbonyl}piperazin-2-one

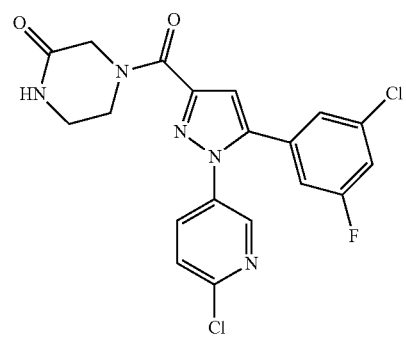 [SMILES: O=C1CN(C(=O)c2cc(-c3cc(F)cc(Cl)c3)n(-c3ccc(Cl)nc3)n2)CCN1]

75 mg (0.18 mmol) of the compound of Example 23A is reacted analogously to the synthesis of the compound of Example 4 with 19 mg (0.19 mmol) of 2-oxopiperazine. 68 mg (87% of theory) of the title compound is obtained.

¹H-NMR (400 MHz, DMSO-d₆): δ=3.25-3.36 (m, 1H), 3.79-3.86/4.07-4.18/4.52 (m, m, s, 5H), 7.18 (s, 1H), 7.24 (d, 1H), 7.33 (s, 1H), 7.52-7.58 (m, 1H), 7.64-7.72 (m, 1H), 7.86-7.93 (m, 1H), 8.12-8.19 (m, 1H), 8.44-8.52 (m, 1H).

LC-MS (Method 1): $R_t$=0.94 min; MS (ESIpos): m/z=434 [M+H]⁺.

Example 9

1-{[5-(3-Chloro-5-fluorophenyl)-1-(5-chloropyridin-3-yl)-1H-pyrazol-3-yl]carbonyl}imidazolidin-4-one

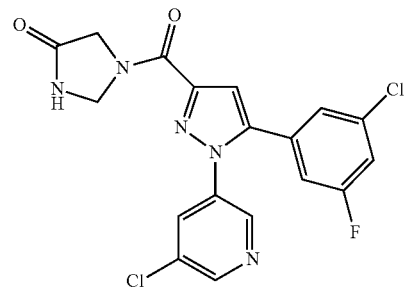 [SMILES: O=C1CN(C(=O)c2cc(-c3cc(F)cc(Cl)c3)n(-c3cncc(Cl)c3)n2)CN1]

75 mg (0.21 mmol) of the compound of Example 26A is reacted analogously to the synthesis of the compound of Example 1 with 29 mg (0.23 mmol) of 4-imidazolinone-hydrochloride. 74 mg (82% of theory) of the title compound is obtained.

¹H-NMR (400 MHz, DMSO-d₆): δ=3.99/4.46 (s, 2H each), 4.91/5.34 (s, 2H each), 7.22-7.36 (m, 3H), 7.56 (d, 1H), 8.15-8.22 (m, 1H), 8.53 (d, 1H), 8.62-8.78 (m, 2H).

LC-MS (Method 1): R$_t$=0.930 min; MS (ESIpos): m/z=420 [M+H-]$^+$.

Example 10

4-{([5-(3-Chloro-5-fluorophenyl)-1-(5-chloropyridin-3-yl)-1H-pyrazol-3-yl]carbonyl}piperazin-2-one

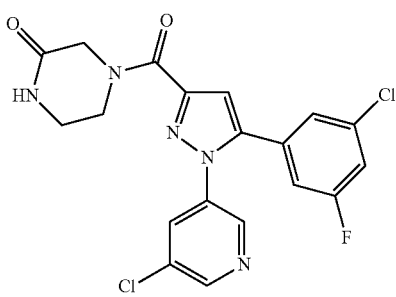 [SMILES: O=C1CN(C(=O)c2cc(-c3cc(F)cc(Cl)c3)n(-c3cncc(Cl)c3)n2)CCN1]

75 mg (0.21 mmol) of the compound of Example 26A is reacted analogously to the synthesis of the compound of Example 1 with 23 mg (0.23 mmol) of 2-oxopiperazine. 77 mg (83% of theory) of the title compound is obtained.

$^1$H-NMR (400 MHz, DMSO-d$_6$): δ=3.24-3.38/3.79-3.86/ 4.08-4.18/4.52 (m, m, m, s, 6H), 7.20 (s, 1H), 7.25 (d, 1H), 7.32 (s, 1H), 7.56 (d, 1H), 8.09-8.20 (m, 2H), 8.48-8.55 (m, 1H), 8.74 (s, 1H).

LC-MS (Method 1): R$_t$=0.91 min; MS (ESIpos): m/z=434 [M+H]$^+$.

Example 11

1-{[5-(3-Chloro-5-fluorophenyl)-1-(6-methylpyridin-3-yl)-1H-pyrazol-3-yl]carbonyl}imidazolidin-4-one

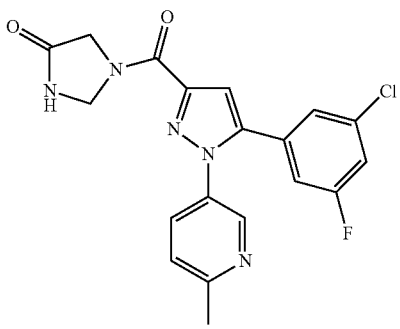 [SMILES: Cc1ccc(-n2nc(C(=O)N3CNC(=O)C3)cc2-c2cc(F)cc(Cl)c2)cn1]

57 mg (0.17 mmol) of the compound of Example 24A is reacted analogously to the synthesis of the compound of Example 1 with 23 mg (0.19 mmol) of 4-imidazolinone-hydrochloride. 58 mg (84% of theory) of the title compound is obtained.

$^1$H-NMR (400 MHz, DMSO-d$_6$): δ=3.98/4.42 (s, 2H each), 4.90/5.31 (s, 2H each), 7.19 (d, 1H), 7.24-7.32 (m, 2H), 7.36-7.44 (m, 1H), 7.53 (d, 1H), 7.70-7.79 (m, 1H), 8.49 (d, 1H), 8.65/8.73 (s, 1H each).

LC-MS (Method 1): R$_t$=0.85 min; MS (ESIpos): m/z=400 [M+H]$^+$.

Example 12

1-{[1-(6-Aminopyridin-3-yl)-5-(3-chloro-5-fluorophenyl)-1H-pyrazol-3-yl]carbonyl}imidazolidin-4-one

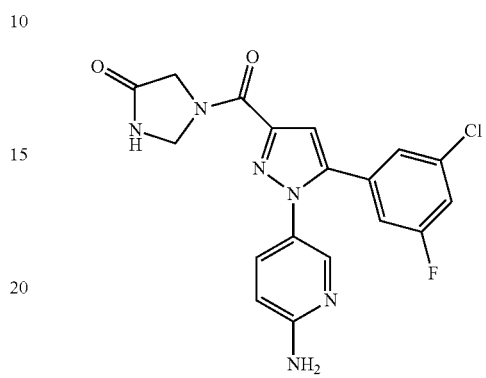

19 mg (0.05 mmol) of the compound of Example 25A is reacted analogously to the synthesis of the compound of Example 3 with 27 mg (0.22 mmol) of 4-imidazolinone-hydrochloride. After the precipitate is filtered and purified by means of preparative HPLC (mobile solvent: acetonitrile/ water gradient), 14 mg (64% of theory) of the title compound is obtained.

58 mg (84% of theory) of the title compound is obtained.

$^1$H-NMR (400 MHz, DMSO-d$_6$): δ=3.97/4.40 (s, 2H each), 4.89/5.28 (s, 2H each), 6.38-6.52 (m, 3H), 7.15-7.28 (m, 3H), 7.38-7.45 (m, 1H), 7.46-7.52 (m, 1H), 7.90 (d, 1H), 8.63/8.71 (s, 1H each).

LC-MS (Method 1): R$_t$=0.71 min; MS (ESIpos): m/z=401 [M+H]$^+$.

Example 13

1-{[5-(3-Chloro-5-fluorophenyl)-1-(pyridin-4-yl)-1H-pyrazol-3-yl]carbonyl}imidazolidin-4-one

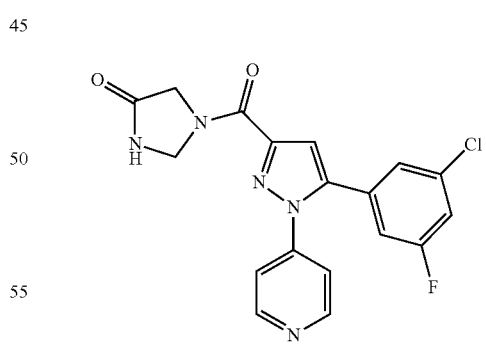

9 mg (0.03 mmol) of the compound of Example 27A is reacted analogously to the synthesis of the compound of Example 1 with 4 mg (0.03 mmol) of 4-imidazolinone-hydrochloride. 4 mg (35% of theory) of the title compound is obtained.

$^1$H-NMR (400 MHz, DMSO-d$_6$): δ=3.99/4.46 (s, 2H each), 4.91/5.35 (s, 2H each), 7.24-7.30 (m, 2H), 7.31-7.35 (m, 1H), 7.39-7.45 (m, 1H), 7.55-7.61 (m, 1H), 8.65-8.77 (m, 3H).

Example 14

1-{[5-(3-Chloro-5-fluorophenyl)-1-(2-chloropyridin-4-yl)-1H-pyrazol-3-yl]carbonyl}imidazolidin-4-one

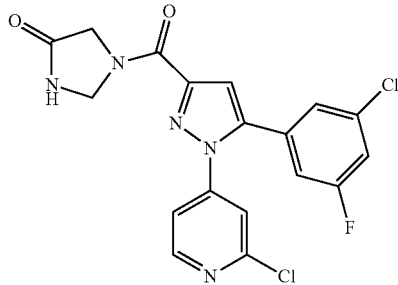 [SMILES: O=C1CN(C(=O)c2cc(-c3cc(F)cc(Cl)c3)n(-c3ccnc(Cl)c3)n2)CN1]

192 mg (0.55 mmol) of the compound of Example 28A is reacted analogously to the synthesis of the compound of Example 3 with 71 mg (0.58 mmol) of 4-imidazolinone-hydrochloride. 152 mg (66% of theory) of the title compound is obtained as a precipitate as well as 57 mg (25% of theory) after the filtrate is purified by means of preparative HPLC (mobile solvent: acetonitrile/water gradient).

$^1$H-NMR (400 MHz, DMSO-$d_6$): δ=3.99/4.48 (s, 2H each), 4.91/5.36 (s, 2H each), 7.29 (d, 1H), 7.30-7.37 (m, 2H), 7.38-7.42 (m, 1H), 7.61 (dt, 1H), 7.64 (dd, 1H), 8.45-8.49 (m, 1H), 8.67/8.75 (s, 1H each).

LC-MS (Method 1): $R_t$=0.94 min; MS (ESIpos): m/z=420 [M+H]$^+$.

Example 15

4-{[5-(3-Chloro-5-fluorophenyl)-1-(2-chloropyridin-4-yl)-1H-pyrazol-3-yl]carbonyl}piperazin-2-one

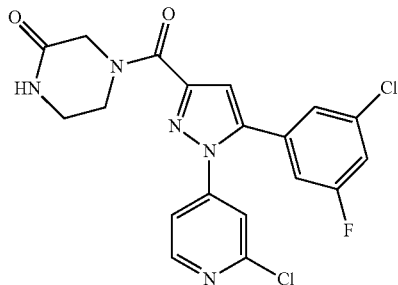 [SMILES: O=C1CN(C(=O)c2cc(-c3cc(F)cc(Cl)c3)n(-c3ccnc(Cl)c3)n2)CCN1]

30 mg (0.09 mmol) of the compound of Example 28A is reacted analogously to the synthesis of the compound of Example 4 with 9 mg (0.09 mmol) of 2-oxopiperazine. 32 mg (87% of theory) of the title compound is obtained.

$^1$H-NMR (400 MHz, DMSO-$d_6$): δ=3.25-3.39 (m, 1H), 3.78-3.88/4.04-4.21/4.50 (m, m, s, 5H), 7.17 (s, 1H), 7.26-7.36 (m, 2H), 7.39 (s, 1H), 7.51-7.66 (m, 2H), 8.17 (s, 1H), 8.42-8.51 (m, 1H).

Example 16

1-({5-(3-Chloro-5-fluorophenyl)-1-[2-(trifluoromethyl)pyridin-4-yl]-1H-pyrazol-3-yl}carbonyl)imidazolidin-4-one

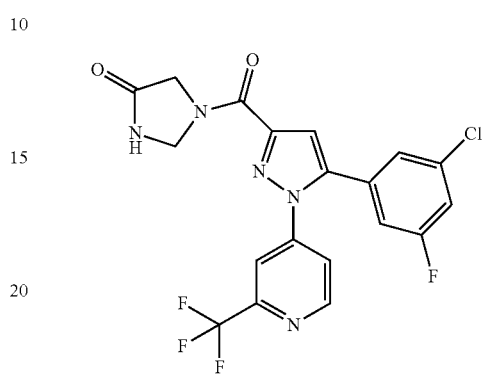

50 mg (0.13 mmol) of the compound of Example 29A is reacted analogously to the synthesis of the compound of Example 3 with 17 mg (0.14 mmol) of 4-imidazolinone-hydrochloride. 49 mg (83% of theory) of the title compound is obtained after the crude product is purified by means of preparative HPLC (mobile solvent: acetonitrile/water gradient).

$^1$H-NMR (400 MHz, DMSO-$d_6$): δ=4.00/4.48 (s, 2H each), 4.92/5.36 (s, 2H each), 7.31 (d, 1H), 7.33-7.39 (m, 1H), 7.40-7.44 (m, 1H), 7.62 (dt, 1H), 7.66-7.74 (m, 1H), 7.83-7.87 (m, 1H), 8.69/8.76 (s, 1H each), 8.84 (t, 1H).

LC-MS (Method 1): $R_t$=0.94 min; MS (ESIpos): m/z=454 [M+H]$^+$.

Example 17

4-({5-(3-Chloro-5-fluorophenyl)-1-[2-(trifluoromethyl)pyridin-4-yl]-1H-pyrazol-3-yl}) carbonyl)piperazin-2-one

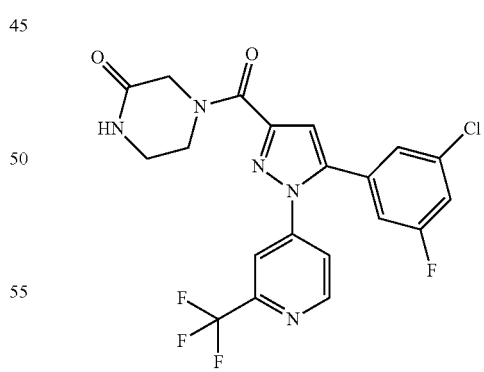

50 mg (0.13 mmol) of the compound of Example 29A is reacted analogously to the synthesis of the compound of Example 4 with 14 mg (0.14 mmol) of 2-oxopiperazine. 51 mg (84% of theory) of the title compound is obtained.

$^1$H-NMR (400 MHz, DMSO-$d_6$): δ=3.25-3.36 (m, 2H), 3.84/4.08 (t, 2H each), 4.16/4.49 (s, 2H each), 7.19 (s, 1H), 7.35 (d, 1H), 7.42 (s, 1H), 7.59-7.67 (m, 2H), 7.81 (s, 1H), 8.17 (s, 1H), 8.83 (d, 1H).

LC-MS (Method 1): R$_t$=0.92 min; MS (ESIpos): m/z=468 [M+H]$^+$.

Example 18

{5-(3-Chloro-5-fluorophenyl)-1-[2-(trifluoromethyl)pyridin-4-yl]-1H-pyrazol-3-yl}(1,3-thiazolidin-3-yl)methanone

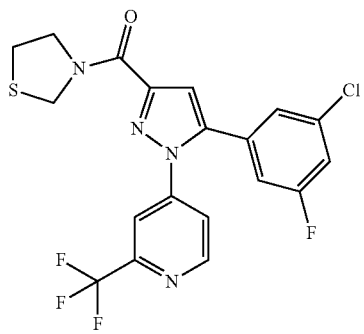 [SMILES: O=C(c1cc(-c2cc(F)cc(Cl)c2)n(-c2ccnc(C(F)(F)F)c2)n1)N1CCSC1]

120 mg (0.31 mmol) of the compound of Example 29A is reacted analogously to the synthesis of the compound of Example 4 with 30 mg (0.33 mmol) of thiazolidine. 85 mg (59% of theory) of the title compound is obtained.

$^1$H-NMR (400 MHz, DMSO-d$_6$): δ=3.09 (t, 1H), 3.15 (t, 1H), 3.88 (t, 1H), 4.21 (t, 1H), 4.70 (s, 1H), 5.04 (s, 1H), 7.26 (s, 1H), 7.34 (d, 1H), 7.41 (s, 1H), 7.59-7.72 (m, 2H), 7.84 (d, 1H), 8.83 (d, 1H).

LC-MS (Method 1): R$_t$=1.20 min; MS (ESIpos): m/z=457 [M+H]$^+$.

Example 19

{5-(3-Chloro-5-fluorophenyl)-1-[2-(trifluoromethyl)pyridin-4-yl]-1H-pyrazol-3-yl}(1-oxido-1,3-thiazolidin-3-yl)methanone

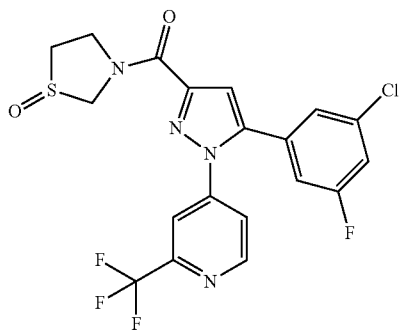 [SMILES: O=C(c1cc(-c2cc(F)cc(Cl)c2)n(-c2ccnc(C(F)(F)F)c2)n1)N1CCS(=O)C1]

36 mg (0.08 mmol) of the compound of Example 18 is reacted analogously to the synthesis of the compound of Example 6 with 19 mg (0.08 mmol, 70%) of meta-chloroperbenzoic acid for 2 hours at room temperature. After the crude product is purified by means of preparative HPLC (mobile solvent: acetonitrile/water gradient), 33 mg (89% of theory) of the title compound is obtained.

$^1$H-NMR (400 MHz, DMSO-d$_6$): δ=3.01-3.38 (m, 2H), 4.00-4.11/4.25-4.37/4.40-4.53/4.56-4.66/4.70 (m, m, m, m, d, 31-1), 4.96/5.45 (dd, 1H each), 7.27-7.45 (m, 3H), 7.62 (d, 1H), 7.68-7.74 (m, 1H), 7.86/7.90 (s, 1H each), 8.84 (d, 1H).

LC-MS (Method 1): R$_t$=0.93 min; MS (ESIpos): m/z=473 [M+H]$^+$.

Example 20

{5-(3-Chloro-5-fluorophenyl)-1-[2-(trifluoromethyl)pyridin-4-yl]-1H-pyrazol-3-yl}(1,1-dioxido-1,3-thiazolidin-3-yl)methanone

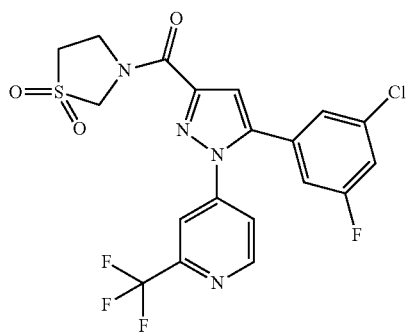 [SMILES: O=C(c1cc(-c2cc(F)cc(Cl)c2)n(-c2ccnc(C(F)(F)F)c2)n1)N1CCS(=O)(=O)C1]

36 mg (0.08 mmol) of the compound of Example 18 is dissolved in 2 ml of dichloromethane, mixed with 39 mg (0.16 mmol, 70% purity) of meta-chloroperbenzoic acid, and stirred for 4 hours at room temperature. After another 7 mg (0.04 mmol, 70% purity) of meta-chloroperbenzoic acid is added and stirred overnight, the reaction mixture is separated by means of preparative HPLC (mobile solvent: acetonitrile/water gradient). 38 mg (99% of theory) of the title compound is obtained.

$^1$H-NMR (400 MHz, DMSO-d$_6$): δ=3.53/3.60 (t, 2H each), 4.10/4.54 (t, 2H each), 4.76/5.20 (s, 2H each), 7.30-7.38 (m, 2H), 7.38-7.44 (m, 1H), 7.63 (dt, 1H), 7.68-7.72/7.74-7.79 (m, 1H each), 7.86/7.91 (s, 1H each), 8.84 (d, 1H).

LC-MS (Method 1): R$_t$=1.05 min; MS (ESIpos): m/z=489 [M+H]$^+$.

Example 21

1-{[5-(3-Chloro-5-fluorophenyl)-1-(2-methylpyridin-4-yl)-1H-pyrazol-3-yl]carbonyl}imidazolidin-4-one

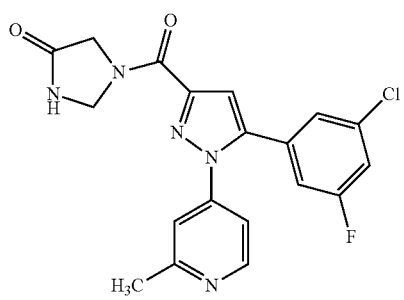 [SMILES: Cc1cc(-n2nc(C(=O)N3CNC(=O)C3)cc2-c2cc(F)cc(Cl)c2)ccn1]

75 mg (0.23 mmol) of the compound of Example 30A is reacted analogously to the synthesis of the compound of Example 3 with 30 mg (0.24 mmol) of 4-imidazolinone-hydrochloride. 81 mg (90% of theory) of the title compound is obtained after the crude product is purified by means of preparative HPLC (mobile solvent: acetonitrile/water gradient).

$^1$H-NMR (400 MHz, DMSO-d$_6$): δ=2.48-2.53 (m, 3H), 3.99/4.45 (s, 2H each), 4.91/5.34 (s, 2H each), 7.08-7.13 (m, 1H), 7.22-7.29 (m, 2H), 7.30-7.33 (m, 1H), 7.38 (dd, 1H), 7.57 (dt, 1H), 8.50 (d, 1H), 8.67/8.75 (s, 1H each).

LC-MS (Method 2): R$_t$=1.74 min; MS (ESIpos): m/z=400 [M+H]$^+$.

Example 22

4-{[5-(3-Chloro-5-fluorophenyl)-1-(2-methylpyridin-4-yl)-1H-pyrazol-3-yl]carbonyl}piperazin-2-one

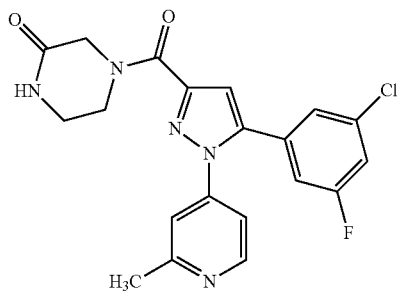 [SMILES: Cc1cc(-n2nc(C(=O)N3CCNC(=O)C3)cc2-c2cc(F)cc(Cl)c2)ccn1]

75 mg (0.23 mmol) of the compound of Example 30A is reacted analogously to the synthesis of the compound of Example 4 with 24 mg (0.24 mmol) of 2-oxopiperazine. 77 mg (82% of theory) of the title compound is obtained.

$^1$H-NMR (400 MHz, DMSO-ds): δ=2.48-2.53 (m, 3H), 3.25-3.36 (m, 2H), 3.83/4.10 (t, 2H each), 4.15/4.51 (s, 2H each), 7.16 (s, 1H), 7.20-7.27 (m, 1H), 7.29-7.37 (m, 2H), 7.57 (d, 11H), 8.17 (s, 1H), 8.46-8.52 (m, 1H).

LC-MS (Method 2): R$_t$=1.69 min; MS (ESIpos): m/z=414 [M+H]$^+$.

Example 23

[5-(3-Chloro-5-fluorophenyl)-1-(2-methylpyridin-4-yl)-1H-pyrazol-3-yl](1,3-thiazolidin-3-yl)methanone

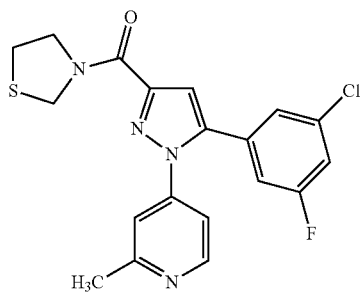 [SMILES: Cc1cc(-n2nc(C(=O)N3CCSC3)cc2-c2cc(F)cc(Cl)c2)ccn1]

150 mg (0.45 mmol) of the compound of Example 30A is reacted analogously to the synthesis of the compound of Example 4 with 43 mg (0.48 mmol) of thiazolidine. 137 mg (74% of theory) of the title compound is obtained.

$^1$H-NMR (400 MHz, DMSO-d$_6$): δ=2.47-2.53 (m, 3H), 3.08/3.14 (t, 2H each), 3.87/4.21 (t, 2H each), 4.69/5.04 (s, 2H each), 7.09 (d, 1H), 7.22/7.24 (s, 2H each), 7.31 (s, 1H), 7.38 (d, 1H), 7.57 (d, 1H), 8.49 (d, 1H).

LC-MS (Method 3): R$_t$=0.99 min; MS (ESIpos): m/z=403 [M+H]$^+$.

Example 24

[5-(3-Chloro-5-fluorophenyl)-1-(2-methylpyridin-4-yl)-1H-pyrazol-3-yl](1-oxido-1,3-thiazolidin-3-yl)methanone

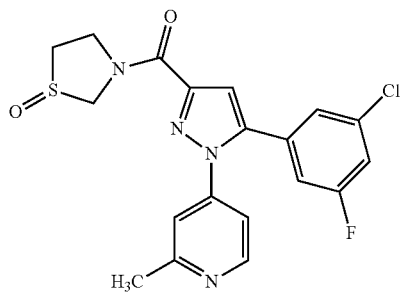 [SMILES: Cc1cc(-n2nc(C(=O)N3CCS(=O)C3)cc2-c2cc(F)cc(Cl)c2)ccn1]

55 mg (0.14 mmol) of the compound of Example 23 is reacted analogously to the synthesis of the compound of Example 6 with 34 mg (0.14 mmol, 70%) of meta-chloroperbenzoic acid for 2 hours at room temperature. After the crude product is purified by means of preparative HPLC (mobile solvent: acetonitrile/water gradient), 53 mg (93% of theory) of the title compound is obtained.

$^1$H-NMR (400 MHz, DMSO-d$_6$): δ=2.48-2.52 (m, 3H), 2.99-3.25 (m, 2H), 4.00-4.13/4.24-4.36/4.39-4.52/4.56-4.73 (m, 3H each), 4.95/5.44 (d, 1H each), 7.12 (d, 1H), 7.21-7.29 (m, 2H), 7.32 (s, 1H), 7.40/7.44 (s, 1H each), 7.57 (d, 1H), 8.50 (d, 1H).

LC-MS (Method 3): R$_t$=0.71 min; MS (ESIpos): m/z=419 [M+H]$^+$.

Example 25

1-{[5-(3-Chloro-5-fluorophenyl)-1-(2-methoxypyridin-4-yl)-1H-pyrazol-3-yl]carbonyl}imidazolidin-4-one

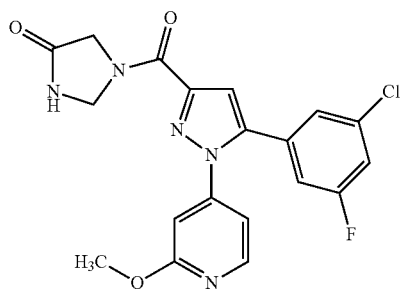 [SMILES: COc1cc(-n2nc(C(=O)N3CNC(=O)C3)cc2-c2cc(F)cc(Cl)c2)ccn1]

8 mg (0.02 mmol) of the compound of Example 31A is reacted analogously to the synthesis of the compound of Example 3 with 3 mg (0.03 mmol) of 4-imidazolinone-hydrochloride. After the crude product is purified by means of preparative HPLC (mobile solvent: acetonitrile/water gradient), 6 mg (63% of theory) of the title compound is obtained.

Example 26

1-({5-[3-Bromo-5-(trifluoromethoxy)phenyl]-1-(pyridin-2-yl)-1H-pyrazol-3-yl}carbonyl)imidazolidin-4-one

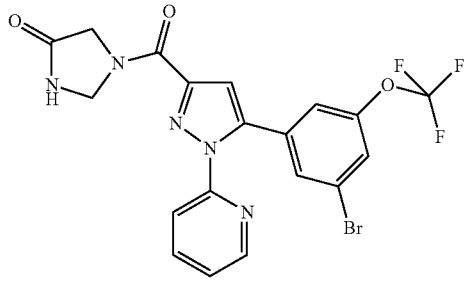 [SMILES: O=C1CN(C(=O)c2cc(-c3cc(Br)cc(OC(F)(F)F)c3)n(-c3ccccn3)n2)CN1]

75 mg (0.18 mmol) of the compound of Example 37A is reacted analogously to the synthesis of the compound of Example 1 with 24 mg (0.19 mmol) of 4-imidazolinone-hydrochloride. 75 mg (87% of theory) of the title compound is obtained.

$^1$H-NMR (400 MHz, DMSO-d$_6$): δ=4.00/4.47 (s, 2H each), 4.92/5.36 (s, 2H each), 7.18-7.24 (m, 1H), 7.28-7.33 (m, 1H), 7.47-7.54 (m, 1H), 7.71 (s, 2H), 7.91 (dd, 1H), 8.07-8.16 (m, 1H), 8.27-8.35 (m, 1H), 8.68/8.74 (s, 1H each).

LC-MS (Method 1): R$_t$=0.99 min; MS (ESIpos): m/z=496 [M+H]$^+$.

Example 27

1-({5-[3-Bromo-5-(trifluoromethoxy)phenyl]-(6-chloropyridin-2-yl)-1H-pyrazol-3-yl}carbonyl)imidazolidin-4-one

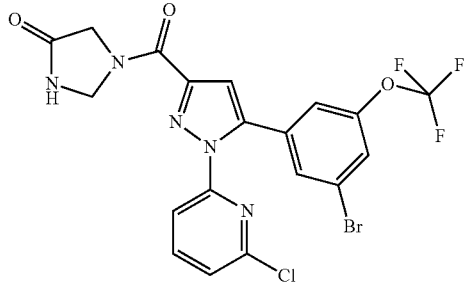 [SMILES: O=C1CN(C(=O)c2cc(-c3cc(Br)cc(OC(F)(F)F)c3)n(-c3cccc(Cl)n3)n2)CN1]

75 mg (0.16 mmol) of the compound of Example 38A is reacted analogously to the synthesis of the compound of Example 1 with 22 mg (0.18 mmol) of 4-imidazolinone-hydrochloride. 65 mg (75% of theory) of the title compound is obtained.

$^1$H-NMR (400 MHz, DMSO-d$_6$): δ=4.00/4.48 (s, 2H each), 4.92/5.36 (s, 2H each), 7.26-7.34 (m, 2H), 7.59 (d, 1H), 7.77 (d, 2H), 7.94 (dd, 1H), 8.10-8.18 (m, 1H), 8.70/8.75 (s, 1H each).

LC-MS (Method 1): R$_t$=1.09 min; MS (ESIpos): m/z=530 [M+H]$^+$.

Example 28

1-({5-[3-Bromo-5-(trifluoromethoxy)phenyl]-1-(pyridin-3-yl)-1H-pyrazol-3-yl}carbonyl)imidazolidin-4-one

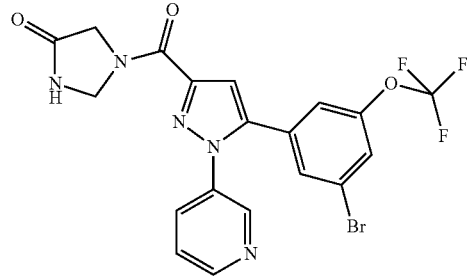 [SMILES: O=C1CN(C(=O)c2cc(-c3cc(Br)cc(OC(F)(F)F)c3)n(-c3cccnc3)n2)CN1]

75 mg (0.16 mmol) of the compound of Example 39A is reacted analogously to the synthesis of the compound of Example 3 with 21 mg (0.17 mmol) of 4-imidazolinone-hydrochloride. After the crude product is purified by means of preparative HPLC (mobile solvent: acetonitrile/water gradient), 73 mg (93% of theory) of the title compound is obtained.

$^1$H-NMR (400 MHz, DMSO-d$_6$): δ=3.99/4.44 (s, 2H each), 4.91/5.32 (s, 2H each), 7.21 (s, 1H), 7.36 (d, 1H), 7.50-7.59 (m, 1H), 7.74 (d, 2H), 7.88 (t, 1H), 8.60-8.78 (m, 3H).

LC-MS (Method 1): R$_t$=0.96 min; MS (ESIpos): m/z=496 [M+H]$^+$.

Example 29

4-({5-[3-Bromo-5-(trifluoromethoxy)phenyl]-1-(pyridin-3-yl)-1H-pyrazol-3-yl}carbonyl)piperazin-2-one

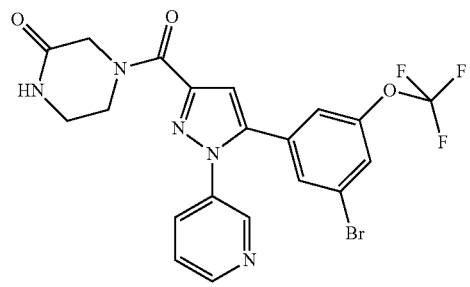 [SMILES: O=C1CN(C(=O)c2cc(-c3cc(Br)cc(OC(F)(F)F)c3)n(-c3cccnc3)n2)CCN1]

75 mg (0.16 mmol) of the compound of Example 39A is reacted analogously to the synthesis of the compound of Example 4 with 17 mg (0.17 mmol) of 2-oxopiperazine. 21 mg (25% of theory) of the title compound is obtained as a fine precipitate as well as 37 mg (46% of theory) of the title compound after the filtrate is purified by means of preparative HPLC (mobile solvent: acetonitrile/water gradient).

$^1$H-NMR (400 MHz, DMSO-d$_6$): δ=3.24-3.39 (m, 1H), 3.79-3.87/4.09-4.19/4.54 (m, m, s, 5H), 7.20 (d, 1H), 7.24 (s, 1H), 7.50-7.58 (m, 1H), 7.73 (d, 2H), 7.85 (d, 1H), 8.16 (s, 1H), 8.58-8.69 (m, 2H).

Example 30

(5-[3-Bromo-5-(trifluoromethoxy)phenyl]-1-(pyridin-3-yl)-1H-pyrazol-3-yl) (1,3-thiazolidin-3-yl)methanone

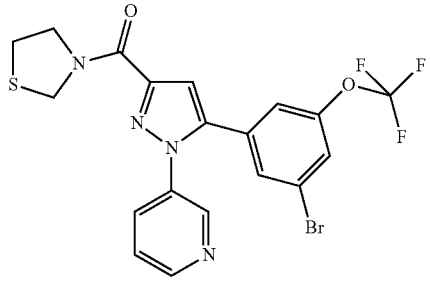 [SMILES: O=C(c1cc(-c2cc(Br)cc(OC(F)(F)F)c2)n(-c2cccnc2)n1)N1CCSC1]

130 mg (0.30 mmol) of the compound of Example 39A is reacted analogously to the synthesis of the compound of Example 1 with 0.03 ml (0.33 mmol) of thiazolidine. 116 mg (77% of theory) of the title compound is obtained.

$^1$H-NMR (400 MHz, DMSO-$d_6$): δ=3.00-3.21 (m, 2H), 3.88 (s, 1H), 4.22 (s, 1H), 4.70 (s, 1H), 5.03 (s, 1H), 7.19 (s, 1H), 7.30 (s, 1H), 7.54 (s, 1H), 7.66-7.80 (m, 2H), 7.87 (s, 1H), 8.64 (s, 2H).

LC-MS (Method 1): $R_t$=1.12 min; MS (ESIpos): m/z=499 [M+H]$^+$.

Example 31

{5-[3-Bromo-5-(trifluoromethoxy)phenyl]-1-(pyridin-3-yl)-1H-pyrazol-3-yl}(1-oxido-1,3-thiazolidin-3-yl)methanone (racemic)

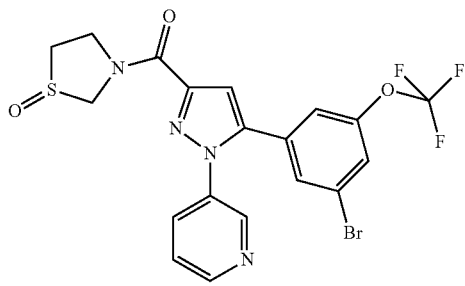 [SMILES: O=C(c1cc(-c2cc(Br)cc(OC(F)(F)F)c2)n(-c2cccnc2)n1)N1CCS(=O)C1]

97 mg (0.19 mmol) of the compound of Example 30 is reacted overnight analogously to the synthesis of the compound of Example 6 with 48 mg (0.19 mmol, 70%) of meta-chloroperbenzoic acid. After the crude product is filtered by a Millipore spray filter and the residue is subsequently purified by means of preparative HPLC (mobile solvent: acetonitrile/water gradient), 82 mg (83% of theory) of the title compound is obtained.

$^1$H-NMR (400 MHz, DMSO-$d_6$): δ=2.99-3.37 (m, 2H), 3.99-4.09/4.25-4.37/4.39-4.52/4.56-4.70/4.96/5.46 (m, m, m, m, dd, dd, 4H), 7.20 (s, 1H), 7.31-7.38 (m, 1H), 7.50-7.59 (m, 1H), 7.74 (d, 2H), 7.85-7.93 (m, 1H), 8.63-8.71 (m, 2H).

LC-MS (Method 3): $R_t$=0.92 min; MS (ESIpos): m/z=515 [M+H]$^+$.

By preparative HPLC in a chiral phase [Daicel Chiralpak AD-H, 5 μm, 250 mm×20 mm; eluant: isohexane/ethanol 50:50; flow: 15 ml/min; temperature: 30° C.; UV detection: 220 nm], the enantiomers are separated:

Enantiomer 31-1

$R_t$=6.02 min [Daicel Chiralpak AD-H, 5 μm, 250 mm×4.6 mm; eluant: isohexane/ethanol 40:60; flow: 1 ml/min; temperature: 40° C.; UV detection: 220 nm];
[α]$_D$20=+111.90, c=0.335, methanol;

Enantiomer 31-2

$R_t$=8.57 min [Daicel Chiralpak AD-H, 5 μm, 250 mm×4.6 mm; eluant: isohexane/ethanol 40:60; flow: 1 ml/min; temperature: 40° C.; UV detection: 220 nm];
[α]$_D$20=−111.10, c=0.360, methanol.

Example 32

{5-[3-Bromo-5-(trifluoromethoxy)phenyl]-1-(pyridin-3-yl)-1H-pyrazol-3-yl}(1,1-dioxido-1,3-thiazolidin-3-yl)methanone

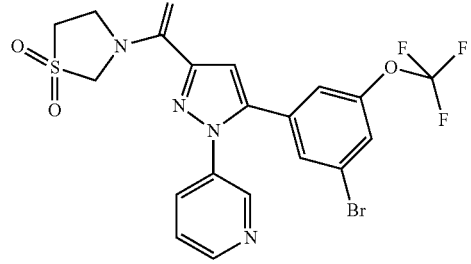

59 mg (0.12 mmol) of the compound of Example 30 is reacted overnight at room temperature with 61 mg (0.25 mmol, 70%) of meta-chloroperbenzoic acid. After the crude product is filtered by a Millipore spray filter and the residue is subsequently purified by means of preparative HPLC (mobile solvent: acetonitrile/water gradient), 23 mg (37% of theory) of the title compound as well as 16 mg of the compound of Example 33 are obtained.

$^1$H-NMR (400 MHz, DMSO-$d_6$): δ=3.43-3.63 (m, 2H), 4.10/4.55/4.75/5.17 (s, 4H each), 7.19 (s, 1H), 7.36 (s, 1H), 7.55 (s, 1H), 7.74 (d, 2H), 7.81-8.01 (m, 1H), 8.67 (s, 2H).

LC-MS (Method 3): $R_t$=1.06 min; MS (ESIpos): m/z=531 [M+H]$^+$.

Example 33

{5-[3-Bromo-5-(trifluoromethoxy)phenyl]-1-(1-oxidopyridin-3-yl)-1H-pyrazol-3-yl}(1,1-dioxido-1,3-thiazolidin-3-yl)methanone

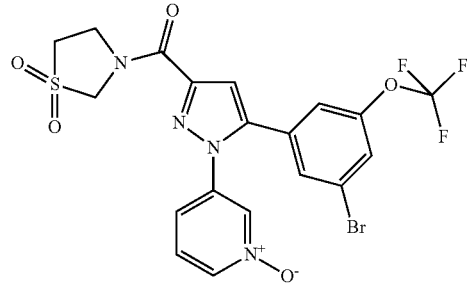 [SMILES: O=C(c1cc(-c2cc(Br)cc(OC(F)(F)F)c2)n(-c2ccc[n+]([O-])c2)n1)N1CCS(=O)(=O)C1]

59 mg (0.12 mmol) of the compound of Example 30 is reacted overnight at room temperature with 61 mg (0.25 mmol, 70%) of meta-chloroperbenzoic acid. After the crude product is filtered by a Millipore spray filter and residue is subsequently purified by means of preparative HPLC (mobile solvent: acetonitrile/water gradient), 16 mg (24% of theory) of the title compound as well as 23 mg of the compound of Example 32 are obtained.

$^1$H-NMR (400 MHz, DMSO-$d_6$): δ=3.51/3.57 (t, 2H each), 4.09/4.55 (t, 2H each), 4.74/5.19 (s, 2H each), 7.28 (d, 1H), 7.35 (s, 2H), 7.43-7.50 (m, 1H), 7.80 (s, 2H), 8.32 (d, 1H), 8.53/8.68 (s, 1H each).

LC-MS (Method 3): $R_t$=0.88 min; MS (ESIpos): m/z=547 [M+H]$^+$.

Example 34

1-({5-[3-Bromo-5-(trifluoromethoxy)phenyl]-1-(6-chloropyridin-3-yl)-1H-pyrazol-3-yl}carbonyl)imidazolidin-4-one

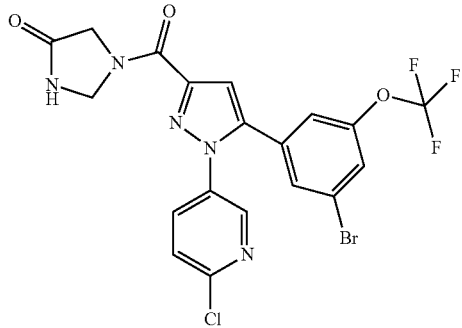 [SMILES: O=C1CN(C(=O)c2cc(-c3cc(Br)cc(OC(F)(F)F)c3)n(-c3ccc(Cl)nc3)n2)CN1]

75 mg (0.14 mmol, 84% purity) of the compound of Example 40A is reacted analogously to the synthesis of the compound of Example 3 with 18 mg (0.15 mmol) of 4-imidazolinone-hydrochloride. After the crude product is purified by means of preparative HPLC (mobile solvent: acetonitrile/water gradient), 48 mg (66% of theory) of the title compound is obtained.

$^1$H-NMR (400 MHz, DMSO-$d_6$): δ=3.99/4.43 (s, 2H each), 4.91/5.32 (s, 2H each), 7.23-7.28 (m, 1H), 7.35 (d, 1H), 7.68 (dd, 1H), 7.76-7.80 (m, 2H), 7.89-7.97 (m, 1H), 8.51 (d, 1H), 8.66-8.77 (m, 1H).

LC-MS (Method 1): $R_t$=1.07 min; MS (ESIpos): m/z=530 [M+H]$^+$.

Example 35

4-({5-[3-Bromo-5-(trifluoromethoxy)phenyl]-1-(6-chloropyridin-3-yl)-1H-pyrazol-3-yl}carbonyl)piperazin-2-one

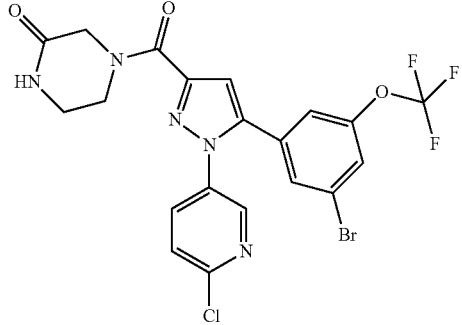 [SMILES: O=C1CN(C(=O)c2cc(-c3cc(Br)cc(OC(F)(F)F)c3)n(-c3ccc(Cl)nc3)n2)CCN1]

75 mg (0.14 mmol, 84% purity) of the compound of Example 40A is reacted analogously to the synthesis of the compound of Example 4 with 15 mg (0.15 mmol) of 2-oxopiperazine. 56 mg (75% of theory) of the title compound is obtained.

$^1$H-NMR (400 MHz, DMSO-$d_6$): δ=3.25-3.36 (m, 2H), 3.79-3.86/4.08-4.18/4.52 (m, m, s, 4H), 7.21-7.28 (m, 2H), 7.68 (t, 1H), 7.74-7.79 (m, 2H), 7.87-7.93 (m, 1H), 8.16 (s, 1H), 8.43-8.51 (m, 1H).

LC-MS (Method 1): $R_t$=1.05 min; MS (ESIpos): m/z=544 [M+H]$^+$.

Example 36

{5-[3-Bromo-5-(trifluoromethoxy)phenyl]-1-(6-chloropyridin-3-yl)-1H-pyrazol-3-yl}(1,3-thiazolidin-3-yl)methanone

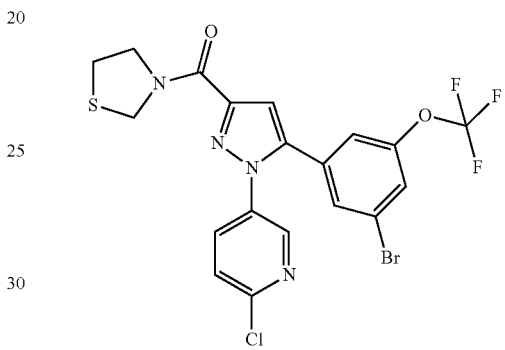

170 mg (0.28 mmol, 76% purity) of the compound of Example 40A is reacted analogously to the synthesis of the compound of Example 4 with 27 mg (0.30 mmol) of thiazolidine. 96 mg (62% of theory) of the title compound is obtained.

$^1$H-NMR (400 MHz, DMSO-$d_6$): δ=3.08/3.12 (t, 2H each), 3.87/4.21 (t, 2H each), 4.70/5.03 (s, 2H each), 7.24 (s, 1H), 7.29 (s, 1H), 7.67 (d, 1H), 7.77 (s, 2H), 7.89-7.96 (m, 1H), 8.48-8.53 (m, 1H).

LC-MS (Method 3): $R_t$=1.32 min; MS (ESIpos): m/z=533 [M+H]$^+$.

Example 37

{5-[3-Bromo-5-(trifluoromethoxy)phenyl]-1-(6-chloropyridin-3-yl)-1H-pyrazol-3-yl}(1-oxido-1,3-thiazolidin-3-yl)methanone (racemic)

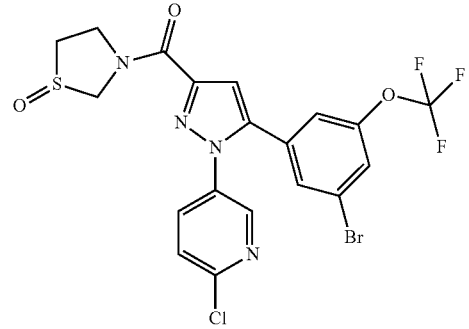 [SMILES: O=C(c1cc(-c2cc(Br)cc(OC(F)(F)F)c2)n(-c2ccc(Cl)nc2)n1)N1CCS(=O)C1]

38 mg (0.07 mmol) of the compound of Example 36 is reacted analogously to the synthesis of the compound of Example 6 with 18 mg (0.07 mmol, 70%) of meta-chloroperbenzoic acid for 72 hours at room temperature. After the crude product is purified by means of preparative HPLC (mobile solvent: acetonitrile/water gradient), 31 mg (79% of theory) of the title compound is obtained.

$^1$H-NMR (400 MHz, DMSO-d$_6$): δ=2.99-3.39 (m, 2H), 3.98-4.09/4.25-4.37/4.38-4.52/4.54-4.69/4.95/5.45 (m, m, n, m, dd, dd, 4H), 7.22-7.28 (m, 1H), 7.32/7.35 (s, 1H each), 7.68 (d, 11H), 7.78 (s, 2H), 7.91-7.98 (m, 1H), 8.55 (dd, 1H).

LC-MS (Method 2): R$_t$=2.31 min; MS (ESIpos): m/z=549 [M+H]$^+$.

Example 38

{5-[3-Bromo-5-(trifluoromethoxy)phenyl]-1-(6-chloropyridin-3-yl)-1H-pyrazol-3-yl}(1,1-dioxido-1,3-thiazolidin-3-yl)methanone

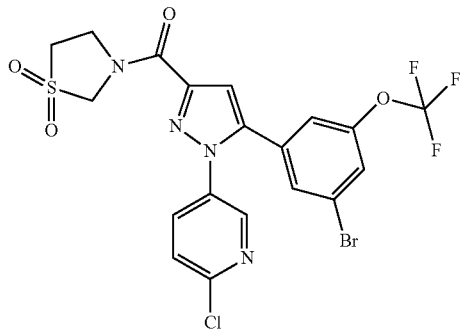 [SMILES: O=C(c1cc(-c2cc(Br)cc(OC(F)(F)F)c2)n(-c2ccc(Cl)nc2)n1)N1CCS(=O)(=O)C1]

38 mg (0.07 mmol) of the compound of Example 36 is dissolved in 2 ml of dichloromethane, mixed with 35 mg (0.14 mmol, 70% purity) of meta-chloroperbenzoic acid, and stirred for 72 hours at room temperature. After the reaction mixture is separated by means of preparative HPLC (mobile solvent: acetonitrile/water gradient), 34 mg (84% of theory) of the title compound is obtained.

$^1$H-NMR (400 MHz, DMSO-d$_6$): δ=3.51/3.57 (t, 2H each), 4.09/4.54 (t, 2H each), 4.75/5.17 (s, 2H each), 7.24 (s, 1H), 7.35 (s, 1H), 7.68 (d, 1H), 7.78 (s, 2H), 7.90-8.02 (m, 1H), 8.50-8.59 (m, 1H).

LC-MS (Method 2): R$_t$=2.52 min; MS (ESIpos): m/z=565 [M+H]$^+$.

Example 39

1-({5-[3-Bromo-5-(trifluoromethoxy)phenyl]-1-(6-fluoropyridin-3-yl)-1H-pyrazol-3-yl}carbonyl)imidazolidin-4-one

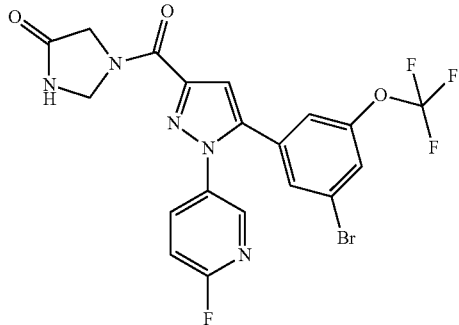 [SMILES: O=C1CN(C(=O)c2cc(-c3cc(Br)cc(OC(F)(F)F)c3)n(-c3ccc(F)nc3)n2)CN1]

75 mg (0.17 mmol) of the compound of Example 42A is reacted analogously to the synthesis of the compound of Example 1 with 23 mg (0.19 mmol) of 4-imidazolinone-hydrochloride. 64 mg (74% of theory) of the title compound is obtained.

$^1$H-NMR (400 MHz, DMSO-d$_6$): δ=3.99/4.43 (s, 2H each), 4.91/5.31 (s, 2H each), 7.24 (s, 1H), 7.30-7.43 (m, 2H), 7.76 (s, 2H), 8.03-8.16 (m, 1H), 8.36 (s, 1H), 8.66/8.74 (s, 1H each).

LC-MS (Method 1): R$_t$=0.98 min; MS (ESIpos): m/z=514 [M+H]$^+$.

Example 40

4-({5-[3-Bromo-5-(trifluoromethoxy)phenyl]-1-(6-fluoropyridin-3-yl)-1H-pyrazol-3-yl}carbonyl)piperazin-2-one

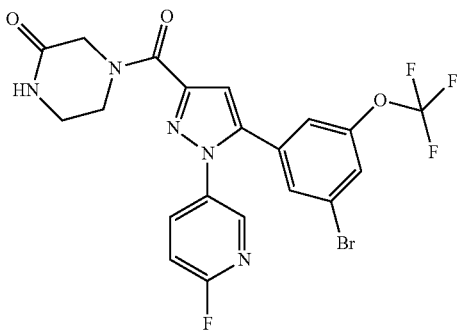 [SMILES: O=C1CN(C(=O)c2cc(-c3cc(Br)cc(OC(F)(F)F)c3)n(-c3ccc(F)nc3)n2)CCN1]

50 mg (0.11 mmol) of the compound of Example 42A is reacted analogously to the synthesis of the compound of Example 1 with 12 mg (0.12 mmol) of 2-oxopiperazine. 51 mg (85% of theory) of the title compound is obtained.

$^1$H-NMR (400 MHz, DMSO-d$_6$): δ=3.24-3.36 (m, 2H), 3.79-3.87/4.08-4.19/4.53 (m, m, s, 4H), 7.18-7.27 (m, 2H), 7.33-7.41 (m, 1H), 7.73-7.78 (m, 2H), 8.03-8.11 (m, 1H), 8.16 (s, 1H), 8.29-8.36 (m, 1H).

LC-MS (Method 1): R$_t$=0.96 min; MS (ESIpos): m/z=528 [M+H]$^+$.

Example 41

{5-[3-Bromo-5-(trifluoromethoxy)phenyl]-1-(6-fluoropyridin-3-yl)-1H-pyrazol-3-yl}(1,3-thiazolidin-3-yl)methanone

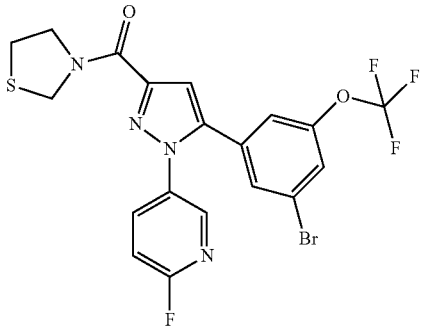 [SMILES: O=C(c1cc(-c2cc(Br)cc(OC(F)(F)F)c2)n(-c2ccc(F)nc2)n1)N1CCSC1]

113 mg (0.25 mmol) of the compound of Example 42A is reacted analogously to the synthesis of the compound of Example 1 with 25 mg (0.28 mmol) of thiazolidine. 91 mg (70% of theory) of the title compound is obtained.

$^1$H-NMR (400 MHz, DMSO-d$_6$): δ=3.08/3.12 (t, 2H each), 3.87/4.21 (t, 2H each), 4.70/5.03 (s, 2H each), 7.21 (s, 1H), 7.30 (s, 1H), 7.36 (dd, 1H), 7.75 (s, 2H), 8.04-8.13 (m, 1H), 8.35 (s, 1H).

LC-MS (Method 1): R$_t$=1.20 min; MS (ESIpos): m/z=517 [M+H]$^+$.

Example 42

1-({5-[3-Bromo-5-(trifluoromethoxy)phenyl]-1-(5-chloropyridin-3-yl)-1H-pyrazol-3-yl}carbonyl)imidazolidin-4-one

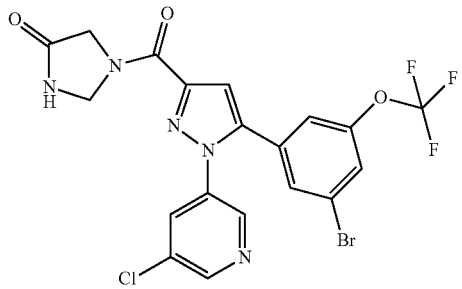 [SMILES: O=C1CN(C(=O)c2cc(-c3cc(Br)cc(OC(F)(F)F)c3)n(-c3cncc(Cl)c3)n2)CN1]

75 mg (0.16 mmol) of the compound of Example 43A is reacted analogously to the synthesis of the compound of Example 1 with 22 mg (0.18 mmol) of 4-imidazolinone-hydrochloride. 72 mg (83% of theory) of the title compound is obtained.

$^1$H-NMR (400 MHz, DMSO-d$_6$): δ=3.99/4.45 (s, 2H each), 4.91/5.33 (s, 2H each), 7.26 (s, 1H), 7.37 (d, 1H), 7.79 (s, 2H), 8.13-8.20 (m, 1H), 8.55-8.60 (m, 11H), 8.62-8.78 (m, 2H).

LC-MS (Method 1): R$_t$=1.04 min; MS (ESIpos): m/z=530 [M+H]$^+$.

Example 43

4-({5-[3-Bromo-5-(trifluoromethoxy)phenyl]-1-(5-chloropyridin-3-yl)-1H-pyrazol-3-yl}carbonyl)piperazin-2-one

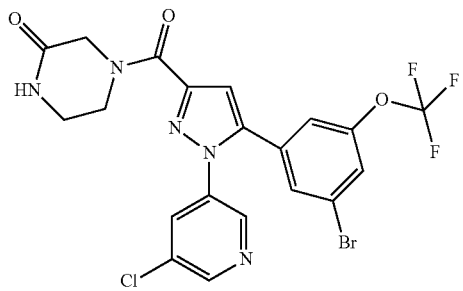 [SMILES: O=C1CN(C(=O)c2cc(-c3cc(Br)cc(OC(F)(F)F)c3)n(-c3cncc(Cl)c3)n2)CCN1]

75 mg (0.16 mmol) of the compound of Example 43A is reacted analogously to the synthesis of the compound of Example 1 with 18 mg (0.18 mmol) of 2-oxopiperazine. 76 mg (86% of theory) of the title compound is obtained.

$^1$H-NMR (400 MHz, DMSO-d$_6$): δ=3.23-3.39/3.79-3.83/ 4.07-4.19/4.52 (m, m, m, s, 6H), 7.20-7.29 (m, 2H), 7.78 (s, 2H), 8.08-8.21 (m, 2H), 8.52-8.59 (m, 1H), 8.75 (s, 1H).

LC-MS (Method 1): R$_t$=1.02 min; MS (ESIpos): m/z=544 [M+H]$^+$.

Example 44

1-({5-[3-Bromo-5-(trifluoromethoxy)phenyl]-1-(5-fluoropyridin-3-yl)-1H-pyrazol-3-yl}carbonyl)imidazolidin-4-one

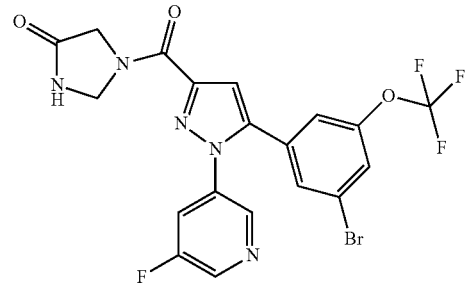 [SMILES: O=C1CN(C(=O)c2cc(-c3cc(Br)cc(OC(F)(F)F)c3)n(-c3cncc(F)c3)n2)CN1]

75 mg (0.17 mmol) of the compound of Example 44A is reacted analogously to the synthesis of the compound of Example 1 with 23 mg (0.19 mmol) of 4-imidazolinone-hydrochloride. 71 mg (82% of theory) of the title compound is obtained.

$^1$H-NMR (400 MHz, DMSO-d$_6$): δ=4.00/4.46 (s, 2H each), 4.92/5.34 (s, 2H each), 7.25 (s, 1H), 7.38 (dd, 1H), 7.79 (d, 2H), 7.98-8.07 (m, 1H), 8.50 (s, 1H), 8.66/8.71-8.77 (s, m, 2H).

LC-MS (Method 1): R$_t$=0.97 min; MS (ESIpos): m/z=514 [M+H]$^+$.

Example 45

4-({5-[3-Bromo-5-(trifluoromethoxy)phenyl]-1-(5-fluoropyridin-3-yl)-1H-pyrazol-3-yl}carbonyl)piperazin-2-one

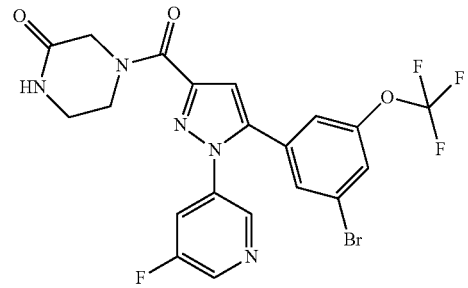 [SMILES: O=C1CN(C(=O)c2cc(-c3cc(Br)cc(OC(F)(F)F)c3)n(-c3cncc(F)c3)n2)CCN1]

75 mg (0.17 mmol) of the compound of Example 44A is reacted analogously to the synthesis of the compound of Example 1 with 19 mg (0.19 mmol) of 2-oxopiperazine. 80 mg (90% of theory) of the title compound is obtained.

$^1$H-NMR (400 MHz, DMSO-d$_6$): δ=3.24-3.37/3.79-3.87/4.09-4.19/4.52 (m, m, m, s, 6H), 7.20-7.29 (m, 2H), 7.77 (s, 2H), 7.91-8.02 (m, 1H), 8.16 (s, 1H), 8.49 (s, 1H), 8.73 (s, 1H).

Example 46

1-({5-[3-Bromo-5-(trifluoromethoxy)phenyl]-1-(6-methylpyridin-3-yl)-1H-pyrazol-3-yl}carbonyl)imidazolidin-4-one

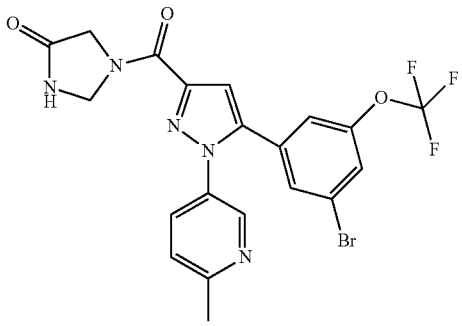 [SMILES: Cc1ccc(-n2nc(C(=O)N3CNC(=O)C3)cc2-c2cc(Br)cc(OC(F)(F)F)c2)cn1]

50 mg (0.11 mmol) of the compound of Example 41A is reacted analogously to the synthesis of the compound of Example 1 with 15 mg (0.13 mmol) of 4-imidazolinone-hydrochloride. 47 mg (81% of theory) of the title compound is obtained.

$^1$H-NMR (400 MHz, DMSO-d$_6$): δ=3.99/4.42 (s, 2H each), 4.91/5.31 (s, 2H each), 7.20 (s, 1H), 7.33 (d, 1H), 7.39 (dd, 1H), 7.69-7.79 (m, 3H), 8.48 (d, 1H), 8.65/8.73 (s, 1H each).

LC-MS (Method 1): R$_t$=0.97 min; MS (ESIpos): m/z=510 [M+H]$^+$.

Example 47

1-({5-[3-Bromo-5-(trifluoromethoxy)phenyl]-1-(pyridin-4-yl)-1H-pyrazol-3-yl}carbonyl)imidazolidin-4-one

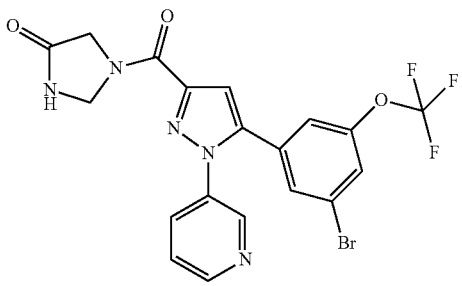 [SMILES: O=C1CN(C(=O)c2cc(-c3cc(Br)cc(OC(F)(F)F)c3)n(-c3cccnc3)n2)CN1]

22 mg (0.05 mmol) of the compound of Example 45A is reacted analogously to the synthesis of the compound of Example 1 with 7 mg (0.06 mmol) of 4-imidazolinone-hydrochloride. 24 mg (94% of theory) of the title compound is obtained.

$^1$H-NMR (400 MHz, DMSO-d$_6$): δ=3.99/4.46 (s, 2H each), 4.91/5.35 (s, 2H each), 7.27 (s, 1H), 7.34 (d, 1H), 7.38-7.45 (m, 2H), 7.79 (d, 2H), 8.64-8.77 (m, 3H).

LC-MS (Method 1): R$_t$=0.87 min; MS (ESIpos): m/z=496 [M+H]$^+$.

Example 48

1-({5-[3-Bromo-5-(trifluoromethoxy)phenyl]-1-(2-chloropyridin-4-yl)-1H-pyrazol-3-yl}carbonyl)imidazolidin-4-one

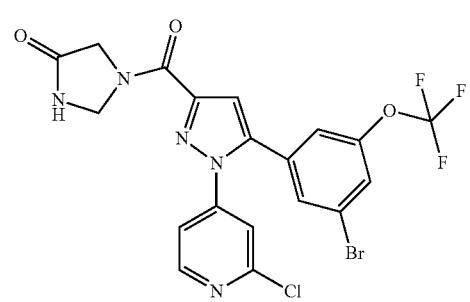 [SMILES: O=C1CN(C(=O)c2cc(-c3cc(Br)cc(OC(F)(F)F)c3)n(-c3ccnc(Cl)c3)n2)CN1]

175 mg (0.38 mmol) of the compound of Example 46A is reacted analogously to the synthesis of the compound of Example 3 with 50 mg (0.41 mmol) of 4-imidazolinone-hydrochloride. After the crude product is purified by means of preparative HPLC (mobile solvent: acetonitrile/water gradient), 136 mg (68% of theory) of the title compound is obtained.

$^1$H-NMR (400 MHz, DMSO-d$_6$): δ=4.00/4.47 (s, 2H each), 4.91/5.35 (s, 2H each), 7.32-7.42 (m, 3H), 7.60 (dd, 1H), 7.82-7.85 (m, 2H), 8.48 (dd, 1H), 8.68/8.75 (s, 1H each).

LC-MS (Method 1): R$_t$=1.05 min; MS (ESIpos): m/z=530 [M+H]$^+$.

Example 49

4-({5-[3-Bromo-5-(trifluoromethoxy)phenyl]-1-(2-chloropyridin-4-yl)-1H-pyrazol-3-yl}carbonyl)piperazin-2-one

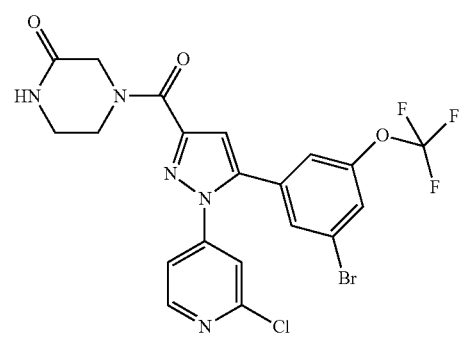 [SMILES: O=C1CN(C(=O)c2cc(-c3cc(Br)cc(OC(F)(F)F)c3)n(-c3ccnc(Cl)c3)n2)CCN1]

30 mg (0.09 mmol) of the compound of Example 46A is reacted analogously to the synthesis of the compound of Example 4 with 9 mg (0.09 mmol) of 2-oxopiperazine. 42 mg (89% of theory) of the title compound is obtained.

$^1$H-NMR (400 MHz, DMSO-d$_6$): δ=3.25-3.38 (m, 2H), 3.78-3.87/4.04-4.19/4.50 (m, m, s, 4H), 7.23 (s, 1H), 7.29-7.40 (m, 2H), 7.53 (d, 1H), 7.83 (s, 2H), 8.17 (s, 1H), 8.44-8.51 (m, 1H).

Example 50

1-({5-[3-Bromo-5-(trifluoromethoxy)phenyl]-1-[2-(trifluoromethyl)pyridin-4-yl]-1H-pyrazol-3-yl}carbonyl)imidazolidin-4-one

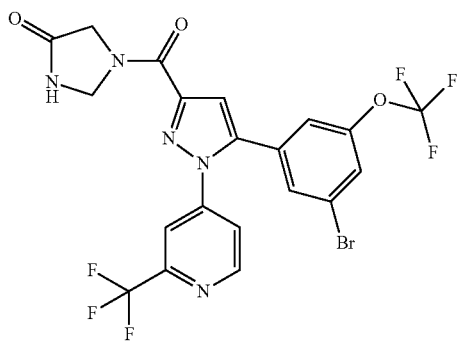 [SMILES: O=C1CN(C(=O)c2cc(-c3cc(Br)cc(OC(F)(F)F)c3)n(-c3ccnc(C(F)(F)F)c3)n2)CN1]

75 mg (0.15 mmol) of the compound of Example 47A is reacted analogously to the synthesis of the compound of Example 1 with 20 mg (0.17 mmol) of 4-imidazolinone-hydrochloride. 72 mg (84% of theory) of the title compound is obtained.

$^1$H-NMR (400 MHz, DMSO-$d_6$): δ=4.00/4.47 (s, 2H each), 4.92/5.36 (s, 2H each), 7.32-7.39 (m, 2H), 7.74-7.83 (m, 2H), 7.85 (d, 2H), 8.69/8.76 (s, 1H each), 8.83-8.89 (m, 1H).

LC-MS (Method 1): R$_t$=1.05 min; MS (ESIpos): m/z=564 [M+H]$^+$.

Example 51

{5-[3-Bromo-5-(trifluoromethoxy)phenyl]-1-[2-(trifluoromethyl)pyridin-4-yl]-1H-pyrazol-3-yl}(1-oxido-1,3-thiazolidin-3-yl)methanone

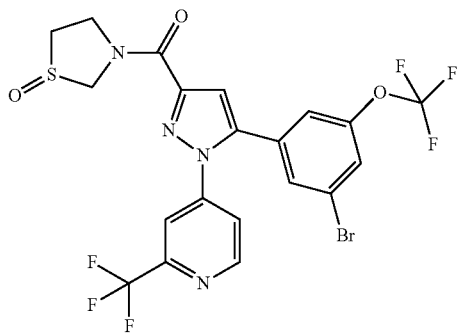 [SMILES: O=C(c1cc(-c2cc(Br)cc(OC(F)(F)F)c2)n(-c2ccnc(C(F)(F)F)c2)n1)N1CCS(=O)C1]

43 mg (0.08 mmol) of the compound of Example 117 is reacted overnight analogously to the synthesis of the compound of Example 6 with 19 mg (0.08 mmol, 70%) of meta-chloroperbenzoic acid. After the crude product is filtered by a Millipore spray filter and the residue is subsequently purified by means of preparative HPLC (mobile solvent: acetonitrile/water gradient), 38 mg (86% of theory) of the title compound is obtained.

$^1$H-NMR (400 MHz, DMSO-$d_6$): δ=3.02-3.32 (m, 2H), 4.01-4.11/4.25-4.37/4.40-4.53/4.56-4.65/4.69 (m, m, m, m, d, 3H), 4.96/5.45 (dd, 1H each), 7.31-7.38 (m, 2H), 7.76-7.89 (m, 4H), 8.86 (d, 1H).

LC-MS (Method 1): R$_t$=1.09 min; MS (ESIpos): m/z=583 [M+H]$^+$.

Example 52

{5-[3-Bromo-5-(trifluoromethoxy)phenyl]-1-[2-(trifluoromethyl)pyridin-4-yl]-1H-pyrazol-3-yl}(1,1-dioxido-1,3-thiazolidin-3-yl)methanone

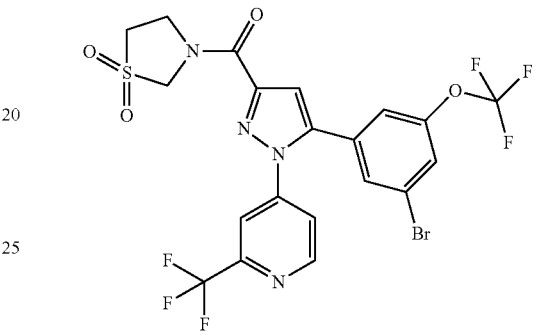

43 mg (0.08 mmol) of the compound of Example 117 is dissolved in 2.5 ml of dichloromethane, mixed with 39 mg (0.16 mmol, 70% purity) of meta-chloroperbenzoic acid, and stirred overnight at room temperature. The reaction mixture is concentrated by evaporation in a rotary evaporator. The residue is diluted with acetonitrile, filtered over a Millipore spray filter, and separated by means of preparative HPLC (mobile solvent: acetonitrile/water gradient). 37 mg (81% of theory) of the title compound is obtained.

$^1$H-NMR (400 MHz, DMSO-$d_6$): δ=3.52/3.60 (t, 2H each), 4.10/4.54 (t, 2H each), 4.76/5.19 (s, 2H each), 7.29-7.41 (m, 2H), 7.75-7.90 (m, 4H), 8.86 (d, 1H).

LC-MS (Method 1): R$_t$=1.19 min; MS (ESIpos): m/z=599 [M+H]$^+$.

Example 53

1-({5-[3-Bromo-5-(trifluoromethoxy)phenyl]-1-(2-methylpyridin-4-yl)-1H-pyrazol-3-yl}carbonyl)imidazolidin-4-one

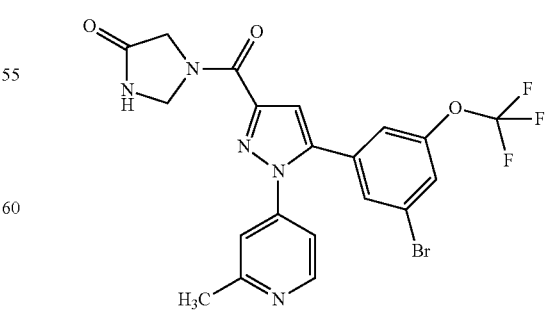

75 mg (0.17 mmol) of the compound of Example 48A is reacted analogously to the synthesis of the compound of Example 1 with 23 mg (0.19 mmol) of 4-imidazolinone-hydrochloride. 72 mg (83% of theory) of the title compound is obtained.

$^1$H-NMR (400 MHz, DMSO-d$_6$): δ=2.46-2.49 (m, 3H), 3.99/4.45 (s, 2H each), 4.91/5.34 (s, 2H each), 7.13-7.19 (m, 1H), 7.23 (s, 1H), 7.30-7.36 (m, 2H), 7.77-7.82 (m, 2H), 8.51 (d, 1H), 8.67/8.75 (s, 1H each).

LC-MS (Method 3): R$_t$=0.90 min; MS (ESIpos): m/z=510 [M+H]$^+$.

Example 54

4-({5-[3-Bromo-5-(trifluoromethoxy)phenyl]-1-(2-methylpyridin-4-yl)-1H-pyrazol-3-yl}carbonyl)piperazin-2-one

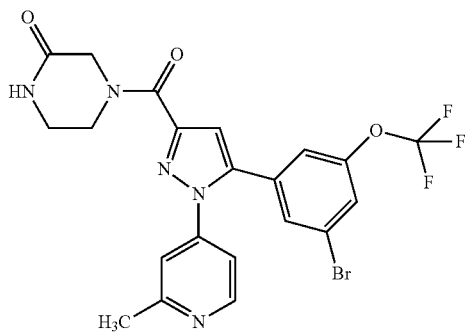 [SMILES: Cc1cc(-n2nc(C(=O)N3CCNC(=O)C3)cc2-c2cc(Br)cc(OC(F)(F)F)c2)ccn1]

50 mg (0.11 mmol) of the compound of Example 48A is reacted analogously to the synthesis of the compound of Example 1 with 12 mg (0.12 mmol) of 2-oxopiperazine. 51 mg (86% of theory) of the title compound is obtained.

$^1$H-NMR (400 MHz, DMSO-d$_6$): δ=2.46 (s, 3H), 3.25-3.36 (m, 2H), 3.79-3.87/4.05-4.19/4.51 (m, m, s, 4H), 7.09-7.16 (m, 1H), 7.19-7.26 (m, 2H), 7.26-7.32 (m, 1H), 7.75-7.82 (m, 2H), 8.17 (s, 1H), 8.46-8.53 (m, 1H).

LC-MS (Method 3): R$_t$=0.87 min; MS (ESIpos): m/z=524 [M+H]$^+$.

Example 55

1-({5-[3-Bromo-5-(trifluoromethoxy)phenyl]-1-(2-methoxypyridin-4-yl)-1H-pyrazol-3-yl}carbonyl)imidazolidin-4-one

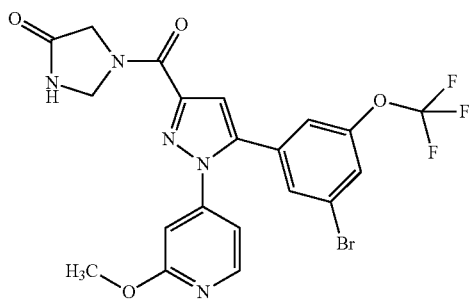 [SMILES: COc1cc(-n2nc(C(=O)N3CNC(=O)C3)cc2-c2cc(Br)cc(OC(F)(F)F)c2)ccn1]

18 mg (0.04 mmol) of the compound of Example 49A is reacted analogously to the synthesis of the compound of Example 1 with 5 mg (0.04 mmol) of 4-imidazolinone-hydrochloride. 4 mg (14% of theory, 82% purity) of the title compound is obtained.

LC-MS (Method 1): R$_t$=1.01 min; MS (ESIpos): m/z=526 [M+H]$^+$.

Example 56

1-({5-[3-Bromo-5-(difluoromethoxy)phenyl]-1-(pyridin-3-yl)-1H-pyrazol-3-yl}carbonyl)imidazolidin-4-one

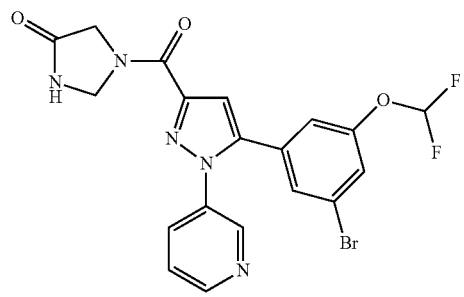

Analogously to Example 1, 47 mg (0.12 mmol) of the compound of Example 55A is reacted with 15 mg (0.13 mmol) of 4-imidazolinone-hydrochloride. 40 mg (72% of theory) of the title compound is obtained.

$^1$H-NMR (400 MHz, DMSO-d$_6$): δ=3.99/4.44 (s, 2H each), 4.91/5.33 (s, 2H each), 7.08/7.26/7.44 (s, 1H each), 7.11-7.14 (m, 1H), 7.31 (d, 1H), 7.39-7.42 (m, 1H), 7.51 (t, 1H), 7.52-7.59 (m, 11H), 7.84-7.91 (m, 1H), 8.67-8.76 (m, 3H).

LC-MS (Method 1): R$_t$=0.88 min; MS (ESIpos): m/z=478 [M+H]$^+$.

Example 57

1-({5-[3-Fluoro-5-(trifluoromethoxy)phenyl]-1-(pyridin-3-yl)-1H-pyrazol-3-yl}carbonyl)imidazolidin-4-one

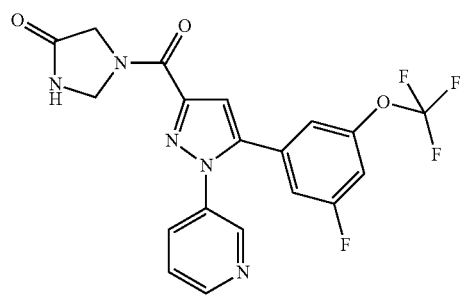 [SMILES: O=C1CN(C(=O)c2cc(-c3cc(F)cc(OC(F)(F)F)c3)n(-c3cccnc3)n2)CN1]

100 mg (0.27 mmol) of the compound of Example 34A is reacted analogously to the synthesis of the compound of Example 1 with 37 mg (0.30 mmol) of 4-imidazolinone-hydrochloride. 98 mg (83% of theory) of the title compound is obtained.

$^1$H-NMR (400 MHz, DMSO-d$_6$): δ=3.99/4.44 (s, 2H each), 4.91/5.33 (s, 2H each), 7.05 (s, 1H), 7.34 (d, 1H), 7.44 (d, 1H), 7.49 (d, 1H), 7.51-7.59 (m, 1H), 7.83-7.92 (m, 1H), 8.61-8.77 (m, 3H).

LC-MS (Method 1): $R_t$=0.88 min; MS (ESIpos): m/z=436 [M+H]$^+$.

Example 58

4-({5-[3-Fluoro-5-(trifluoromethoxy)phenyl]-1-(pyridin-3-yl)-1H-pyrazol-3-yl})carbonyl)piperazin-2-one

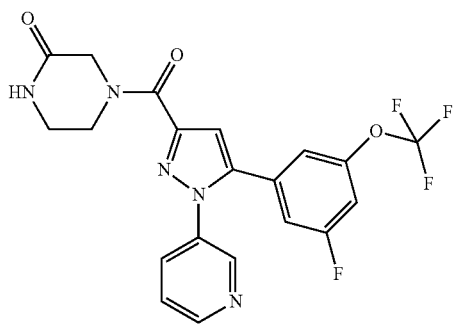 [SMILES: O=C1CN(C(=O)c2cc(-c3cc(F)cc(OC(F)(F)F)c3)n(-c3cccnc3)n2)CCN1]

75 mg (0.20 mmol) of the compound of Example 34A is reacted analogously to the synthesis of the compound of Example 1 with 22 mg (0.17 mmol) of 2-oxopiperazine. 72 mg (79% of theory) of the title compound is obtained.

$^1$H-NMR (400 MHz, DMSO-d$_6$): δ=3.22-3.41/3.78-3.88/4.08-4.21/4.55 (m, m, m, s, 6H), 6.99-7.09 (m, 1H), 7.23 (d, 1H), 7.49 (d, 1H), 7.50-7.60 (m, 1H), 7.85 (d, 1H), 8.16 (s, 1H), 8.56-8.70 (m, 2H).

LC-MS (Method 1): $R_t$=0.86 min; MS (ESIpos): m/z=450 [M+H]$^+$.

Example 59

{5-[3-Fluoro-5-(trifluoromethoxy)phenyl]-1-(pyridin-3-yl)-1H-pyrazol-3-yl}(1,3-thiazolidin-3-yl)methanone

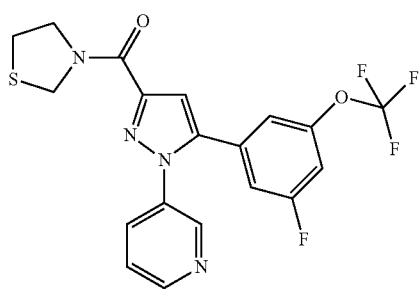 [SMILES: O=C(c1cc(-c2cc(F)cc(OC(F)(F)F)c2)n(-c2cccnc2)n1)N1CCSC1]

200 mg (0.55 mmol) of the compound of Example 34A is reacted analogously to the synthesis of the compound of Example 1 with 0.05 ml (0.60 mmol) of thiazolidine. 193 mg (80% of theory) of the title compound is obtained.

$^1$H-NMR (400 MHz, DMSO-d$_6$): δ=3.10 (dt, 2H), 3.88 (s, 1H), 4.22 (s, 1H), 4.70 (s, 1H), 5.04 (s, 1H), 7.03 (s, 1H), 7.28 (s, 1H), 7.42 (d, 1H), 7.49 (d, 1H), 7.54 (dd, 1H), 7.83-7.91 (m, 1H), 8.60-8.69 (m, 2H).

LC-MS (Method 1): $R_t$=1.07 min; MS (ESIpos): m/z=439 [M+H]$^+$.

Example 60

{5-[3-Fluoro-5-(trifluoromethoxy)phenyl]-1-(pyridin-3-yl)-1H-pyrazol-3-yl}(1-oxido-1,3-thiazolidin-3-yl)methanone (racemic)

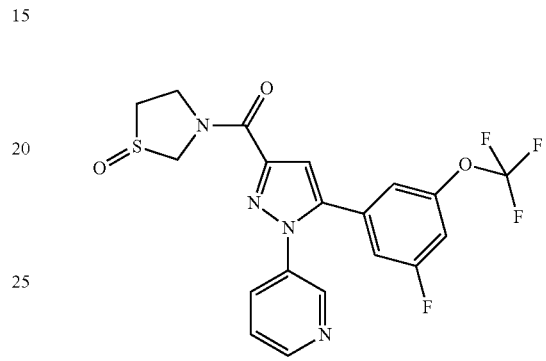

102 mg (0.23 mmol) of the compound of Example 59 is dissolved in 5 ml of dichloromethane, mixed with 57 mg (0.23 mmol, 70% purity) of meta-chloroperbenzoic acid, and stirred for 16 hours at room temperature. The reaction mixture is concentrated by evaporation in a rotary evaporator, mixed with some acetonitrile, filtered over a Millipore spray filter, and then separated by means of preparative HPLC (mobile solvent: acetonitrile/water gradient). 87 mg (82% of theory) of the title compound is obtained.

$^1$H-NMR (400 MHz, DMSO-d$_6$): δ=2.98-3.43 (m, 2H), 3.98-4.10/4.25-4.37/4.39-4.53/4.56-4.71/4.96/5.47 (m, m, m, m, dd, dd, 4H), 7.01-7.08 (m, 1H), 7.29-7.36 (m, 1H), 7.44 (d, 1H), 7.49 (d, 1H), 7.55 (dd, 1H), 7.85-7.93 (m, 1H), 8.67 (d, 2H).

LC-MS (Method 1): $R_t$=0.82 min; MS (ESIpos): m/z=455 [M+H]$^+$.

By preparative HPLC in a chiral phase [Daicel Chiralpak AD-H, 5 μm, 250 mm×20 mm; eluant: isohexane/ethanol 30:70; flow: 15 ml/min; temperature: 45° C.; UV detection: 220 nm], the enantiomers are separated:

Enantiomer 60-1

$R_t$=7.90 min [Daicel Chiralpak AD-H, 5 μm, 250 mm×4.6 mm; eluant: isohexane/ethanol 30:70; flow: 1 ml/min; temperature: 30° C.; UV detection: 220 nm];

$[α]_D^{20}$=+125.60, c=0.445, methanol;

Enantiomer 60-2

$R_t$=13.50 min [Daicel Chiralpak AD-H, 5 μm, 250 mm×4.6 mm; eluant: isohexane/ethanol 30:70; flow: 1 ml/min; temperature: 30° C.; UV detection: 220 nm];

$[α]_D$20=−125.0°, c=0.440, methanol.

Example 61

{5-[3-Fluoro-5-(trifluoromethoxy)phenyl]-1-(pyridin-3-yl)-1H-pyrazol-3-yl}(morpholin-4-yl)methanone

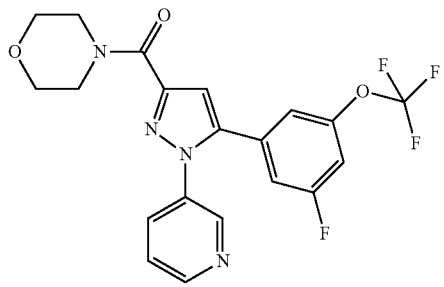 [SMILES: O=C(c1cc(-c2cc(F)cc(OC(F)(F)F)c2)n(-c2cccnc2)n1)N1CCOCC1]

75 mg (0.20 mmol) of the compound of Example 34A is reacted analogously to the synthesis of the compound of Example 1 with 0.02 ml (0.23 mmol) of morpholine. 80 mg (90% of theory) of the title compound is obtained.

$^1$H-NMR (400 MHz, DMSO-$d_6$): δ=3.58-3.71 (m, 6H), 3.91-4.03 (m, 2H), 7.03 (s, 1H), 7.19 (s, 1H), 7.41 (d, 1H), 7.49 (d, 1H), 7.53 (dd, 1H), 7.80-7.87 (m, 1H), 8.60 (d, 1H), 8.65 (dd, 1H).

LC-MS (Method 1): $R_t$=0.97 min; MS (ESIpos): m/z=437 [M+H]$^+$.

Example 62

1-({1-(2-Chloropyridin-4-yl)-5-[3-fluoro-5-(trifluoromethoxy)phenyl]-1H-pyrazol-3-yl}carbonyl)imidazolidin-4-one

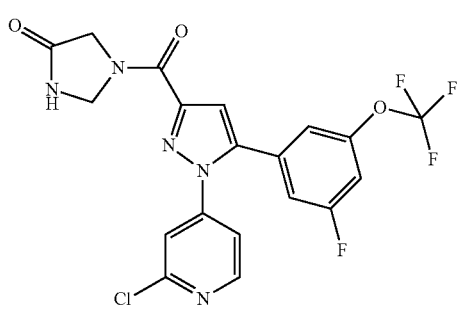 [SMILES: O=C1CN(C(=O)c2cc(-c3cc(F)cc(OC(F)(F)F)c3)n(-c3ccnc(Cl)c3)n2)CN1]

60 mg (0.12 mmol) of the compound of Example 35A is reacted analogously to the synthesis of the compound of Example 3 with 15 mg (0.13 mmol) of 4-imidazolinone-hydrochloride. 36 mg (65% of theory) of the title compound is obtained.

$^1$H-NMR (400 MHz, DMSO-$d_6$): δ=4.00/4.48 (s, 2H each), 4.92/5.36 (s, 2H each), 7.16-7.22 (m, 1H), 7.33 (d, 1H), 7.38 (ddd, 1H), 7.51-7.62 (m, 3H), 8.45-8.50 (m, 1H), 8.68/8.76 (s, 1H each).

LC-MS (Method 1): $R_t$=0.94 min; MS (ESIpos): m/z=470 [M+H]$^+$.

Example 63

4-({-(2-Chloropyridin-4-yl)-5-[3-fluoro-5-(trifluoromethoxy)phenyl]-1H-pyrazol-3-yl}carbonyl)piperazin-2-one

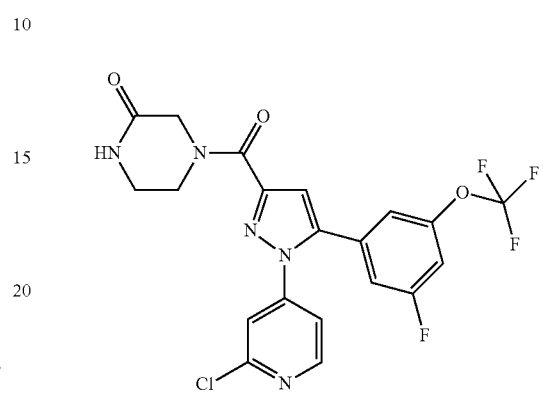

40 mg (0.08 mmol) of the compound of Example 35A is reacted analogously to the synthesis of the compound of Example 4 with 8 mg (0.08 mmol) of 2-oxopiperazine. 27 mg (71% of theory) of the title compound is obtained.

$^1$H-NMR (400 MHz, DMSO-$d_6$): δ=3.24-3.37/3.80-3.87/4.07-4.18/4.50 (m, m, m, s, 6H), 7.19 (d, 1H), 7.22 (d, 1H), 7.32-7.38 (m, 1H), 7.49-7.60 (m, 3H), 8.18 (s, 1H), 8.45-8.50 (m, 1H).

LC-MS (Method 1): $R_t$=0.92 min; MS (ESIpos): m/z=484 [M+H]$^+$.

Example 64

{1-(2-Chloropyridin-4-yl)-5-[3-fluoro-5-(trifluoromethoxy)phenyl]-1H-pyrazol-3-yl}(1-oxido-1,3-thiazolidin-3-yl)methanone

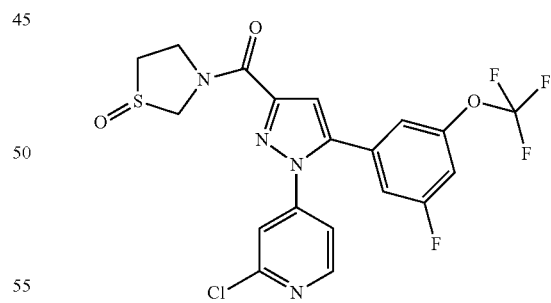

46 mg (0.10 mmol) of the compound of Example 104 is reacted analogously to the synthesis of the compound of Example 6 with 48 mg (0.20 mmol, 70%) of meta-chloroperbenzoic acid for 4 hours at room temperature. After the crude product is purified by means of preparative HPLC (mobile solvent: acetonitrile/water gradient), 8 mg (17% of theory) of the title compound as well as 38 mg of the compound of Example 65 are obtained.

$^1$H-NMR (400 MHz, DMSO-$d_6$): δ=3.00-3.29 (m, 2H), 4.00-4.11/4.25-4.37/4.41-4.53/4.57-4.74/4.96/5.47 (m, m, m, m, d, d, 4H), 7.15-7.22 (m, 1H), 7.32 (d, 1H), 7.39 (d, 1H), 7.51-7.69 (m, 3H), 8.44-8.51 (m, 1H).

LC-MS (Method 1): $R_t$=0.97 min; MS (ESIpos): m/z=489 [M+H]$^+$.

Example 65

{1-(2-Chloropyridin-4-yl)-5-[3-fluoro-5-(trifluoromethoxy)phenyl]-1H-pyrazol-3-yl}(1,1-dioxido-1,3-thiazolidin-3-yl)methanone

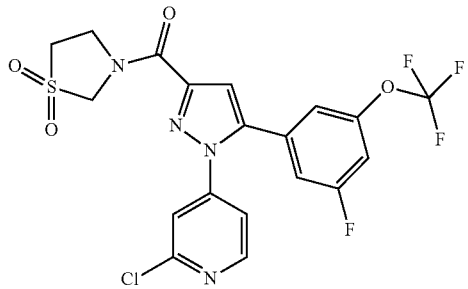 [SMILES: O=C(c1cc(-c2cc(F)cc(OC(F)(F)F)c2)n(-c2ccnc(Cl)c2)n1)N1CCS(=O)(=O)C1]

46 mg (0.10 mmol) of the compound of Example 104 is reacted analogously to the synthesis of the compound of Example 6 with 48 mg (0.20 mmol, 70%) of meta-chloroperbenzoic acid for 4 hours at room temperature. After the crude product is purified by means of preparative HPLC (mobile solvent: acetonitrile/water gradient), 38 mg (77% of theory) of the title compound as well as 8 mg of the compound of Example 64 are obtained.

$^1$H-NMR (400 MHz, DMSO-d$_6$): δ=3.51/3.59 (t, 2H each), 4.05/4.55 (t, 2H each), 4.75/5.20 (m, 2H each), 7.14-7.20 (m, 1H), 7.34 (s, 1H), 7.39 (dd, 1H), 7.51-7.63 (m, 3H), 7.71 (s, 1H), 8.47 (d, 1H).

LC-MS (Method 1): $R_t$=1.09 min; MS (ESIpos): m/z=505 [M+H]$^+$.

Example 66

1-({5-[3-(Difluoromethoxy)-5-fluorophenyl]-1-(pyridin-3-yl)-1H-pyrazol-3-yl}carbonyl)imidazolidin-4-one

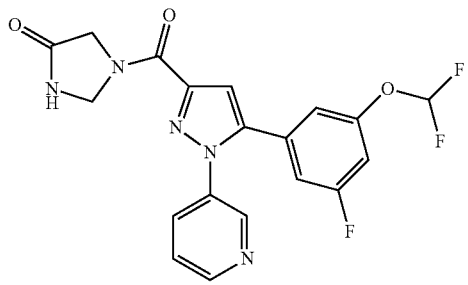 [SMILES: O=C1CN(C(=O)c2cc(-c3cc(F)cc(OC(F)F)c3)n(-c3cccnc3)n2)CN1]

75 mg (0.22 mmol) of the compound of Example 52A is reacted analogously to the synthesis of the compound of Example 3 with 28 mg (0.23 mmol) of 4-imidazolinone-hydrochloride for 18 hours at room temperature. 68 mg (72% of theory) of the title compound is obtained.

$^1$H-NMR (400 MHz, DMSO-d$_6$): δ=3.99/4.45 (s, 2H each), 4.91/5.33 (s, 2H each), 6.98 (s, 1H), 7.06-7.14 (m, 1H), 7.19-7.32/7.44 (m, s, 3H), 7.51-7.59 (m, 1H), 7.83-7.92 (m, 1H), 8.60-8.77 (m, 3H).

LC-MS (Method 3): $R_t$=0.79 min; MS (ESIpos): m/z=418 [M+H]$^+$.

Example 67

4-({5-[3-(Difluoromethoxy)-5-fluorophenyl]-1-(pyridin-3-yl)-1H-pyrazol-3-yl})carbonyl)piperazin-2-one

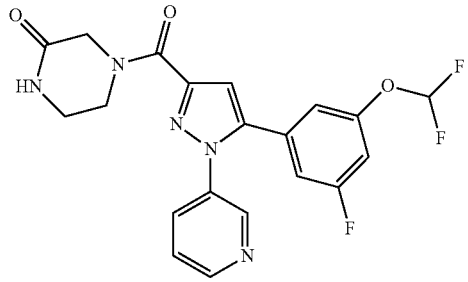 [SMILES: O=C1CN(C(=O)c2cc(-c3cc(F)cc(OC(F)F)c3)n(-c3cccnc3)n2)CCN1]

30 mg (0.09 mmol) of the compound of Example 52A is reacted analogously to the synthesis of the compound of Example 4 with 9 mg (0.09 mmol) of 2-oxopiperazine. 30 mg (80% of theory) of the title compound is obtained.

$^1$H-NMR (400 MHz, DMSO-d$_6$): δ=3.24-3.39/3.79-3.87/4.10-4.21/4.56 (m, m, m, s, 6H), 6.94-7.00 (m, 1H), 7.05-7.13/7.16-7.28/7.44 (m, m, s, 4H), 7.51-7.59 (m, 1H), 7.85 (d, 1H), 8.16 (s, 1H), 8.56-8.69 (m, 2H).

LC-MS (Method 1): $R_t$=0.80 min; MS (ESIpos): m/z=432 [M+H]$^+$.

Example 68

1-({1-(2-Chloropyridin-4-yl)-5-[3-(difluoromethoxy)-5-fluorophenyl]-1H-pyrazol-3-yl}carbonyl)imidazolidin-4-one

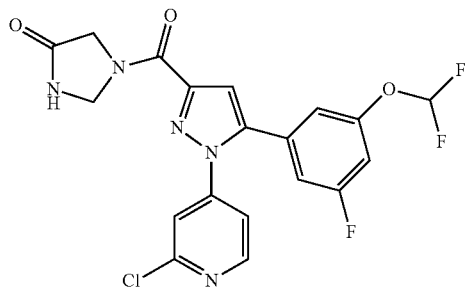 [SMILES: O=C1CN(C(=O)c2cc(-c3cc(F)cc(OC(F)F)c3)n(-c3ccnc(Cl)c3)n2)CN1]

75 mg (0.20 mmol) of the compound of Example 53A is reacted analogously to the synthesis of the compound of Example 3 with 26 mg (0.21 mmol) of 4-imidazolinone-hydrochloride. 66 mg (75% of theory) of the title compound is obtained.

$^1$H-NMR (400 MHz, DMSO-d$_6$): δ=4.00/4.49 (s, 2H each), 4.91/5.37 (s, 2H each), 7.06-7.13/7.21-7.38/7.49 (m, m, s, 6H), 7.61-7.66 (m, 1H), 8.44-8.50 (m, 1H), 8.68/8.75 (s, 1H each).

LC-MS (Method 3): $R_t$=0.90 min; MS (ESIpos): m/z=452 [M-++H]+.

Example 69

4-({1-(2-Chloropyridin-4-yl)-5-[3-(difluoromethoxy)-5-fluorophenyl]-1H-pyrazol-3-yl}carbonyl)piperazin-2-one

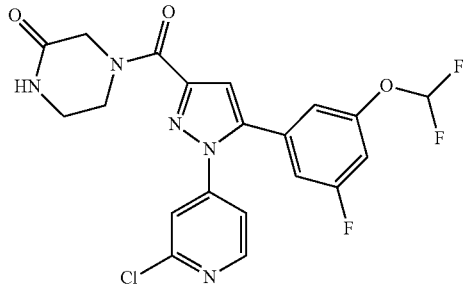 [SMILES: O=C1CN(C(=O)c2cc(-c3cc(F)cc(OC(F)F)c3)n(-c3ccnc(Cl)c3)n2)CCN1]

40 mg (0.10 mmol) of the compound of Example 53A is reacted analogously to the synthesis of the compound of Example 4 with 11 mg (0.11 mmol) of 2-oxopiperazine. 39 mg (80% of theory) of the title compound is obtained.

$^1$H-NMR (400 MHz, DMSO-$d_6$): δ=3.25-3.38/3.80-3.86/4.07-4.18/4.50 (m, m, m, s, 6H), 7.05-7.13/7.15-7.35/7.48 (m, m, s, 6H), 7.54/7.57 (s, 1H each), 8.17 (s, 1H), 8.44-8.49 (m, 1H).

LC-MS (Method 7): $R_t$=0.86 min; MS (ESIpos): m/z=450 [M+H]+.

Example 70

1-({5-[3-Fluoro-5-(2,2,2-trifluoroethoxy)phenyl]-1-(pyridin-3-yl)-1H-pyrazol-3-yl}carbonyl)imidazolidin-4-one

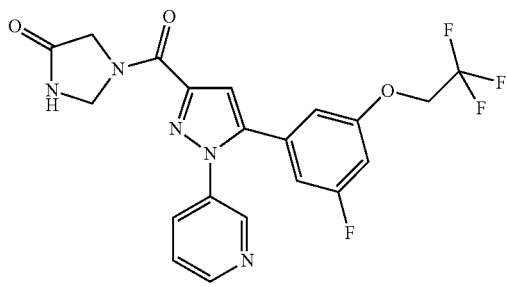 [SMILES: O=C1CN(C(=O)c2cc(-c3cc(F)cc(OCC(F)(F)F)c3)n(-c3cccnc3)n2)CN1]

75 mg (0.20 mmol) of the compound of Example 59A is reacted analogously to the synthesis of the compound of Example 1 with 27 mg (0.22 mmol) of 4-imidazolinone-hydrochloride. 74 mg (84% of theory) of the title compound is obtained.

$^1$H-NMR (400 MHz, DMSO-$d_6$): δ=3.99/4.45 (s, 2H each), 4.80 (q, 2H), 4.91/5.34 (s, 2H each), 6.78 (d, 1H), 6.96 (s, 1H), 7.06-7.13 (m, 1H), 7.24-7.29 (m, 1H), 7.52-7.59 (m, 1H), 7.82-7.91 (m, 1H), 8.60-8.77 (m, 3H).

LC-MS (Method 3): $R_t$=0.87 min; MS (ESIpos): m/z=450 [M+H]+.

Example 71

4-({5-[3-Fluoro-5-(2,2,2-trifluoroethoxy)phenyl]-1-(pyridin-3-yl)-1H-pyrazol-3-yl}carbonyl)piperazin-2-one

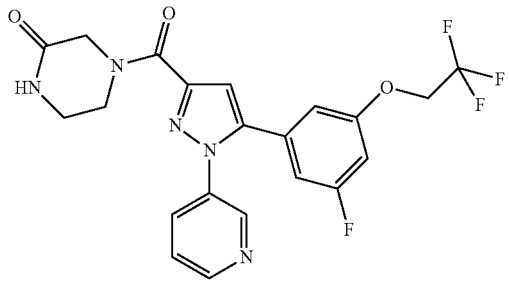 [SMILES: O=C1CN(C(=O)c2cc(-c3cc(F)cc(OCC(F)(F)F)c3)n(-c3cccnc3)n2)CCN1]

75 mg (0.20 mmol) of the compound of Example 59A is reacted analogously to the synthesis of the compound of Example 1 with 22 mg (0.22 mmol) of 2-oxopiperazine. 81 mg (89% of theory) of the title compound is obtained.

$^1$H-NMR (400 MHz, DMSO-$d_6$): δ=3.24-3.37/3.79-3.87/4.11-4.20/4.56 (m, m, m, s, 6H), 6.75-6.82 (m, 1H), 6.94 (s, 1H), 7.09 (d, 1H), 7.15 (s, 1H), 7.50-7.59 (m, 1H), 7.83 (d, 1H), 8.16 (s, 1H), 8.55-8.68 (m, 2H).

LC-MS (Method 3): $R_t$=0.84 min; MS (ESIpos): m/z=464 [M+H]+.

Example 72

{5-[3-Fluoro-5-(2,2,2-trifluoroethoxy)phenyl]-1-(pyridin-3-yl)-1H-pyrazol-3-yl}(1,3-thiazolidin-3-yl)methanone

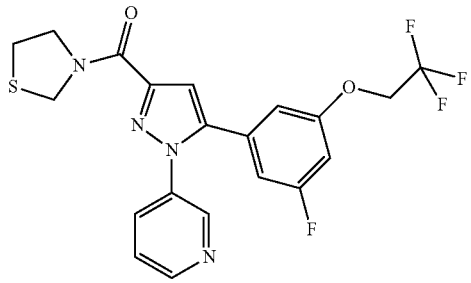 [SMILES: O=C(c1cc(-c2cc(F)cc(OCC(F)(F)F)c2)n(-c2cccnc2)n1)N1CCSC1]

120 mg (0.32 mmol) of the compound of Example 59A is reacted analogously to the synthesis of the compound of Example 1 with 0.03 ml (0.35 mmol) of thiazolidine. 110 mg (77% of theory) of the title compound is obtained.

$^1$H-NMR (400 MHz, DMSO-$d_6$): δ=3.10 (dt, 2H), 3.87/4.23 (t, 2H each), 4.70/5.05 (s, 2H each), 4.97 (q, 2H), 6.77 (d, 1H), 6.95 (s, 1H), 7.05-7.12 (m, 1H), 7.20 (s, 1H), 7.54 (dd, 1H), 7.85 (t, 1H), 8.59-8.67 (m, 2H).

Example 73

{5-[3-Fluoro-5-(2,2,2-trifluoroethoxy)phenyl]-1-(pyridin-3-yl)-1H-pyrazol-3-yl}(1-oxido-1,3-thiazolidin-3-yl)methanone (racemic)

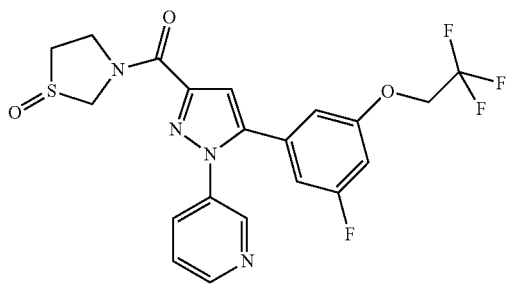 [SMILES: O=C(c1cc(-c2cc(F)cc(OCC(F)(F)F)c2)n(-c2cccnc2)n1)N1CCS(=O)C1]

44 mg (0.10 mmol) of the compound of Example 72 is reacted analogously to the synthesis of the compound of Example 6 with 24 mg (0.10 mmol, 70%) of meta-chloroperbenzoic acid overnight at room temperature. The crude product is filtered over a Millipore spray filter and separated by means of preparative HPLC (mobile solvent: acetonitrile/water gradient). 35 mg (77% of theory) of the title compound is obtained.

$^1$H-NMR (400 MHz, DMSO-d$_6$): δ=2.97-3.40 (m, 2H), 3.98-4.09/4.26-4.38/4.40-4.52/4.57-4.70 (m, 3H each), 4.80 (q, 2H), 4.96/5.48 (dd, 1H each), 6.78 (d, 1H), 6.96 (s, 1H), 7.06-7.13 (m, 1H), 7.23/7.26 (s, 1H each), 7.55 (dd, 1H), 7.84-7.92 (m, 1H), 8.61-8.69 (m, 2H).

LC-MS (Method 3): R$_t$=0.85 min; MS (ESIpos): m/z=469 [M+H]$^+$.

Example 74

(1,1-Dioxido-1,3-thiazolidin-3-yl){5-[3-fluoro-5-(2,2,2-trifluoroethoxy)phenyl]-1-(pyridin-3-yl)-1H-pyrazol-3-yl}methanone

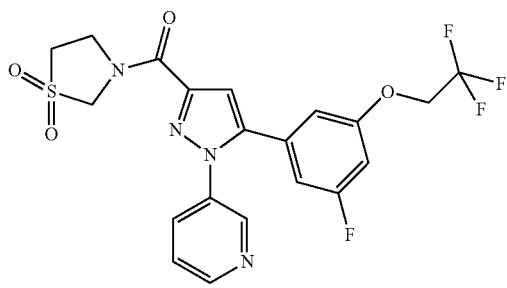 [SMILES: O=C(c1cc(-c2cc(F)cc(OCC(F)(F)F)c2)n(-c2cccnc2)n1)N1CCS(=O)(=O)C1]

44 mg (0.10 mmol) of the compound of Example 72 is dissolved in 2.5 ml of dichloromethane, mixed with 50 mg (0.21 mmol, 70% purity) of meta-chloroperbenzoic acid, and stirred for 16 hours at room temperature. The reaction mixture is concentrated by evaporation in a rotary evaporator, mixed with some acetonitrile, filtered over a Millipore spray filter, and then separated by means of preparative HPLC (mobile solvent: acetonitrile/water gradient). 17 mg (36% of theory) of the title compound as well as 8 mg of the compound of Example 75 are obtained.

$^1$H-NMR (400 MHz, DMSO-d$_6$): δ=3.50/3.56 (t, 2H each), 4.09/4.57 (t, 2H each), 4.75/5.19 (s, 2H each), 4.80 (q, 2H), 6.74-6.81 (m, 1H), 6.96 (s, 1H), 7.06-7.13 (m, 1H), 7.26 (s, 1H), 7.55 (dd, 1H), 7.86/7.92 (d, 1H each), 8.61-8.69 (m, 2H).

LC-MS (Method 3): R$_t$=0.97 min; MS (ESIpos): m/z=485 [M+H]$^+$.

Example 75

(1,1-Dioxido-1,3-thiazolidin-3-yl){5-[3-fluoro-5-(2,2,2-trifluoroethoxy)phenyl]-1-(1-oxidopyridin-3-yl)-1H-pyrazol-3-yl}methanone

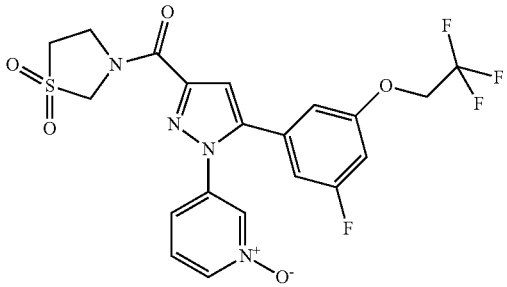 [SMILES: O=C(c1cc(-c2cc(F)cc(OCC(F)(F)F)c2)n(-c2ccc[n+]([O-])c2)n1)N1CCS(=O)(=O)C1]

44 mg (0.10 mmol) of the compound of Example 72 is dissolved in 2.5 ml of dichloromethane, mixed with 50 mg (0.21 mmol, 70% purity) of meta-chloroperbenzoic acid, and stirred for 16 hours at room temperature. The reaction mixture is concentrated by evaporation in a rotary evaporator, mixed with some acetonitrile, filtered over a Millipore spray filter, and then separated by means of preparative HPLC (mobile solvent: acetonitrile/water gradient). 8 mg (16% of theory) of the title compound as well as 17 mg of the compound of Example 74 are obtained.

$^1$H-NMR (400 MHz, DMSO-d$_6$): δ=3.50/3.57 (t, 2H each), 4.08/4.57 (t, 2H each), 4.74/5.21 (s, 2H each), 4.83 (q, 2H), 6.88-6.96 (m, 1H), 7.03 (s, 1H), 7.10-7.17 (m, 1H), 7.25/7.27 (s, 2H each), 7.42/7.51 (m, 1H), 8.30 (d, 1H), 8.49/8.65 (s, 1H each).

LC-MS (Method 3): R$_t$=0.82 min; MS (ESIpos): m/z=501 [M+H]$^+$.

Example 76

1-({5-[3-Chloro-5-(trifluoromethoxy)phenyl]-1-(pyridin-3-yl)-1H-pyrazol-3-yl}carbonyl)imidazolidin-4-one

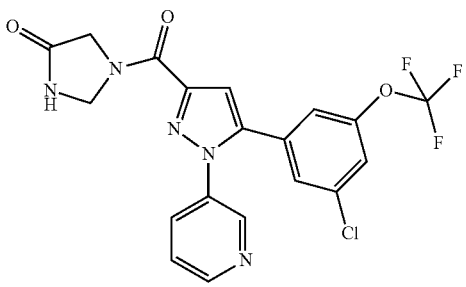 [SMILES: O=C1CN(C(=O)c2cc(-c3cc(Cl)cc(OC(F)(F)F)c3)n(-c3cccnc3)n2)CN1]

75 mg (0.20 mmol) of the compound of Example 36A is reacted analogously to the synthesis of the compound of Example 3 with 26 mg (0.21 mmol) of 4-imidazolinone-hydrochloride. 71 mg (80% of theory) of the title compound is obtained.

$^1$H-NMR (400 MHz, DMSO-d): δ=3.99/4.44 (s, 2H each), 4.91/5.33 (s, 2H each), 7.17 (s, 1H), 7.36 (d, 1H), 7.51-7.58 (m, 1H), 7.63 (d, 2H), 7.84-7.92 (m, 1H), 8.62-8.76 (m, 3H).

LC-MS (Method 1): $R_t$=0.89 min; MS (ESIpos): m/z=452 [M+H]$^+$.

Example 77

{5-[3-Chloro-5-(trifluoromethoxy)phenyl]-1-(pyridin-3-yl)-1H-pyrazol-3-yl}(1,3-thiazolidin-3-yl)methanone

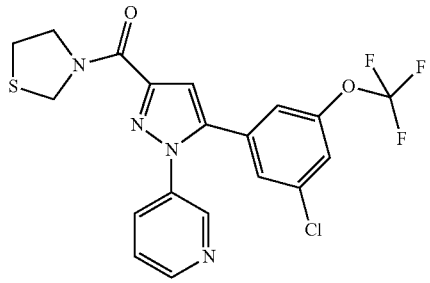 [SMILES: O=C(c1cc(-c2cc(Cl)cc(OC(F)(F)F)c2)n(-c2cccnc2)n1)N1CCSC1]

120 mg (0.31 mmol) of the compound of Example 36A is reacted analogously to the synthesis of the compound of Example 3 with 30 mg (0.34 mmol) of thiazolidine. 86 mg (60% of theory) of the title compound is obtained.

$^1$H-NMR (400 MHz, DMSO-d$_6$): δ=3.08 (t, 1H), 3.12 (t, 1H), 3.87/4.22 (t, 2H each), 4.70/5.04 (s, 2H each), 7.16 (s, 1H), 7.30 (s, 1H), 7.54 (dd, 1H), 7.59-7.67 (m, 2H), 7.83-7.91 (m, 1H), 8.61-8.68 (m, 2H).

LC-MS (Method 1): $R_t$=1.10 min; MS (ESIpos): m/z=455 [M+H]$^+$.

Example 78

{5-[3-Chloro-5-(trifluoromethoxy)phenyl]-1-(pyridin-3-yl)-1H-pyrazol-3-yl}(1-oxido-1,3-thiazolidin-3-yl)methanone (racemic)

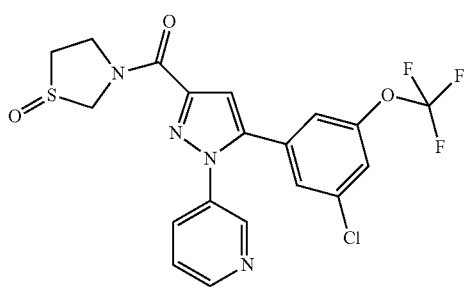 [SMILES: O=C(c1cc(-c2cc(Cl)cc(OC(F)(F)F)c2)n(-c2cccnc2)n1)N1CCS(=O)C1]

38 mg (0.08 mmol) of the compound of Example 77 is reacted analogously to the synthesis of the compound of Example 6 with 21 mg (0.08 mmol, 70%) of meta-chloroperbenzoic acid for 4 hours at room temperature. 39 mg (99% of theory) of the title compound is obtained.

$^1$H-NMR (400 MHz, DMSO-d$_6$): δ=2.99-3.38 (m, 2H), 3.99-4.09/4.26-4.37/4.40-4.52/4.56-4.70 (m, 3H each), 4.96/5.46 (dd, 1H each), 7.16 (s, 1H), 7.34 (d, 1H), 7.54 (dd, 1H), 7.63 (d, 2H), 7.85-7.93 (m, 1H), 8.63-8.70 (m, 2H).

LC-MS (Method 1): $R_t$=0.92 min; MS (ESIpos): m/z=471 [M+H]$^+$.

Example 79

{5-[3-Chloro-5-(trifluoromethoxy)phenyl]-1-(pyridin-3-yl)-1H-pyrazol-3-yl}(1,1-dioxido-1,3-thiazolidin-3-yl)methanone

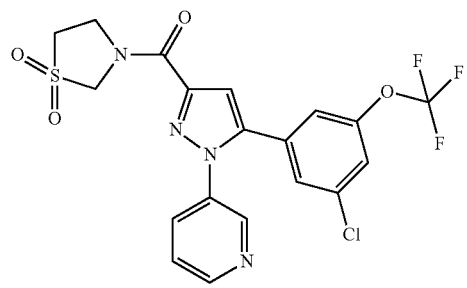 [SMILES: O=C(c1cc(-c2cc(Cl)cc(OC(F)(F)F)c2)n(-c2cccnc2)n1)N1CCS(=O)(=O)C1]

38 mg (0.08 mmol) of the compound of Example 77 is dissolved in 1.5 ml of dichloromethane, mixed with 41 mg (0.17 mmol, 70% purity) of meta-chloroperbenzoic acid, and stirred for 4 hours at room temperature. After the crude product is purified by means of preparative HPLC (mobile solvent: acetonitrile/water gradient), 16 mg (39% of theory) of the title compound as well as 15 mg of the compound of Example 80 are obtained.

$^1$H-NMR (400 MHz, DMSO-d): δ=3.44-3.62 (m, 2H), 4.04-4.16/4.50-4.61 (m, 2H each), 4.75/5.18 (s, 2H each), 7.15 (s, 1H), 7.36 (s, 1H), 7.50-7.59 (m, 1H), 7.64 (d, 2H), 7.83-7.98 (m, 1H), 8.61-8.72 (m, 2H).

LC-MS (Method 1): $R_t$=1.04 min; MS (ESIpos): m/z=487 [M+H]$^+$.

Example 80

{5-[3-Chloro-5-(trifluoromethoxy)phenyl]-1-(1-oxidopyridin-3-yl)-1H-pyrazol-3-yl}(1,1-dioxido-1,3-thiazolidin-3-yl)methanone

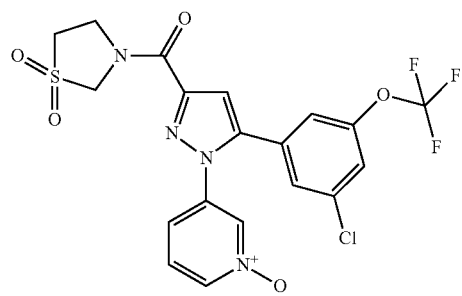 [SMILES: O=C(c1cc(-c2cc(Cl)cc(OC(F)(F)F)c2)n(-c2ccc[n+](O)c2)n1)N1CCS(=O)(=O)C1]

38 mg (0.08 mmol) of the compound of Example 77 is dissolved in 1.5 ml of dichloromethane, mixed with 41 mg (0.17 mmol, 70% purity) of meta-chloroperbenzoic acid, and stirred for 4 hours at room temperature. After the crude product is purified by means of preparative HPLC (mobile solvent: acetonitrile/water gradient), 15 mg (36% of theory) of the title compound as well as 16 mg of the compound of Example 79 are obtained.

$^1$H-NMR (400 MHz, DMSO-$d_6$): δ=3.51/3.57 (t, 2H each), 4.09/4.55 (t, 2H each), 4.75/5.19 (s, 2H each), 7.25-7.37 (m, 3H), 7.43-7.50 (m, 1H), 7.69 (s, 2H), 8.32 (d, 1H), 8.53/8.69 (s, 1H each).

LC-MS (Method 1): $R_t$=0.89 min; MS (ESIpos): m/z=503 [M+H]$^+$.

Example 81

1-({5-[3-Chloro-5-(difluoromethoxy)phenyl]-1-(pyridin-3-yl)-1H-pyrazol-3-yl}carbonyl)imidazolidin-4-one

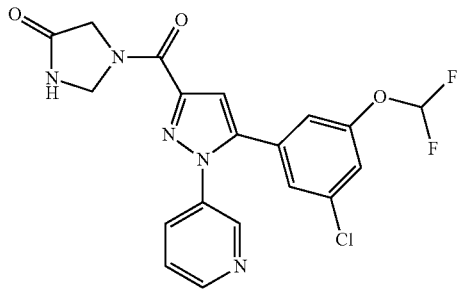

75 mg (0.21 mmol) of the compound of Example 54A is reacted analogously to the synthesis of the compound of Example 3 with 27 mg (0.22 mmol) of 4-imidazolinone-hydrochloride. 73 mg (82% of theory) of the title compound is obtained.

$^1$H-NMR (400 MHz, DMSO-$d_6$): δ=3.99/4.44 (s, 2H each), 4.91/5.33 (s, 2H each), 7.07-7.11 (m, 1H), 7.25-7.33/7.38-7.41/7.45 (m, m, s, 3H), 7.52-7.59 (m, 1H), 7.84-7.91 (m, 1H), 8.63-8.76 (m, 3H).

LC-MS (Method 1): $R_t$=0.87 min; MS (ESIpos): m/z=434 [M+H]$^+$.

Example 82

{5-[3-Chloro-5-(difluoromethoxy)phenyl]-1-(pyridin-3-yl)-1H-pyrazol-3-yl}(1,3-thiazolidin-3-yl)methanone

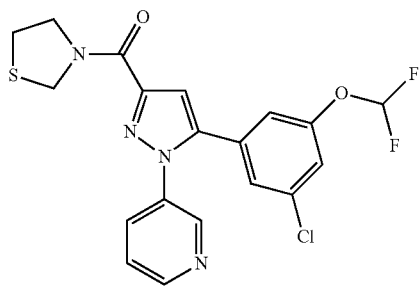 [SMILES: O=C(c1cc(-c2cc(Cl)cc(OC(F)F)c2)n(-c2cccnc2)n1)N1CCSC1]

95 mg (0.26 mmol) of the compound of Example 54A is reacted analogously to the synthesis of the compound of Example 3 with 25 mg (0.28 mmol) of thiazolidine for 30 minutes at room temperature. 65 mg (57% of theory) of the title compound is obtained.

$^1$H-NMR (400 MHz, DMSO-$d_6$): δ=3.08/3.12 (t, 2H each), 3.87/4.22 (t, 2H each), 4.70/5.04 (s, 2H each), 7.08 (s, 1H), 7.27 (d, 2H), 7.39/7.44 (s, 1H each), 7.54 (dd, 1H), 7.83-7.91 (m, 1H), 8.61-8.68 (m, 2H).

LC-MS (Method 1): $R_t$=1.06 min; MS (ESIpos): m/z=437 [M+H]$^+$.

Example 83

{5-[3-Chloro-5-(difluoromethoxy)phenyl]-1-(pyridin-3-yl)-1H-pyrazol-3-yl}(1,1-dioxido-1,3-thiazolidin-3-yl)methanone

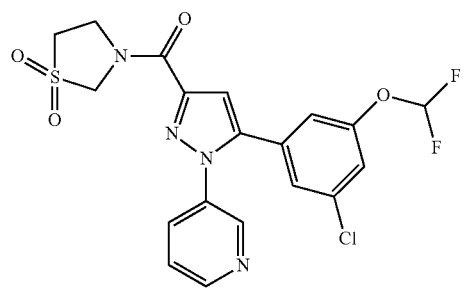 [SMILES: O=C(c1cc(-c2cc(Cl)cc(OC(F)F)c2)n(-c2cccnc2)n1)N1CCS(=O)(=O)C1]

56 mg (0.13 mmol) of the compound of Example 82 is dissolved in 3 ml of dichloromethane, mixed with 63 mg (0.26 mmol, 70% purity) of meta-chloroperbenzoic acid, and stirred for 4 hours at room temperature. After another 11 mg (0.06 mmol, 70% purity) of meta-chloroperbenzoic acid is added and stirred overnight, the reaction mixture is separated by means of preparative HPLC (mobile solvent: acetonitrile/water gradient). 21 mg (35% of theory) of the title compound is obtained.

$^1$H-NMR (400 MHz, DMSO-$d_6$): δ=3.51/3.56 (t, 2H each), 4.09/4.56 (t, 2H each), 4.75/5.18 (s, 2H each), 7.08 (s, 1H), 7.24-7.34 (m, 2H), 7.40/7.44 (s, 1H each), 7.55 (dd, 1H), 7.84-7.97 (m, 1H), 8.63-8.71 (m, 2H).

LC-MS (Method 1): $R_t$=0.92 min; MS (ESIpos): m/z=469 [M+H]$^+$.

Example 84

1-({5-[3-Methoxy-5-(trifluoromethoxy)phenyl]-1-(pyridin-3-yl)-1H-pyrazol-3-yl}carbonyl)imidazolidin-4-one

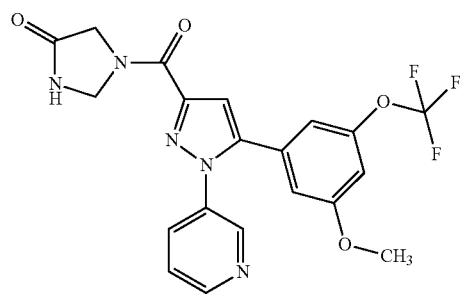 [SMILES: COc1cc(OC(F)(F)F)cc(-c2cc(C(=O)N3CNC(=O)C3)nn2-c2cccnc2)c1]

100 mg (0.26 mmol) of the compound of Example 56A is reacted analogously to the synthesis of the compound of Example 3 with 35 mg (0.28 mmol) of 4-imidazolinone-hydrochloride for 3 hours at room temperature. After the reaction mixture is filtered by a Millipore spray filter and subsequently purified by means of preparative HPLC (mobile solvent: acetonitrile/water gradient), 52 mg (44% of theory) of the title compound is obtained.

$^1$H-NMR (400 MHz, DMSO-d$_6$): δ=3.77 (s, 3H), 3.99/4.45 (s, 2H each), 4.91/5.33 (s, 2H each), 6.68-6.72 (m, 1H), 7.00 (s, 1H), 7.02-7.07 (m, 1H), 7.29 (d, 1H), 7.51-7.58 (m, 1H), 7.83-7.90 (m, 1H), 8.60-8.76 (m, 3H).

LC-MS (Method 3): R$_t$=0.88 min; MS (ESIpos): m/z=448 [M+H]$^+$.

Example 85

4-({5-[3-Methoxy-5-(trifluoromethoxy)phenyl]-1-(pyridin-3-yl)-1H-pyrazol-3-yl}carbonyl)piperazin-2-one

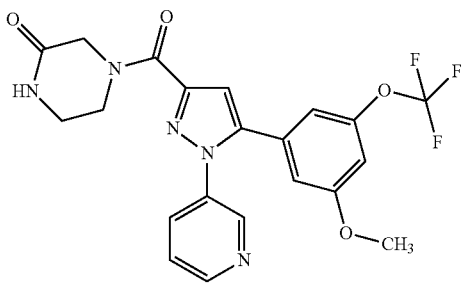 [SMILES: COc1cc(OC(F)(F)F)cc(-c2cc(C(=O)N3CCNC(=O)C3)nn2-c2cccnc2)c1]

50 mg (0.13 mmol) of the compound of Example 56A is reacted analogously to the synthesis of the compound of Example 4 with 14 mg (0.14 mmol) of 2-oxopiperazine. 54 mg (89% of theory) of the title compound is obtained.

$^1$H-NMR (400 MHz, DMSO-d$_6$): δ=3.25-3.37 (m, 2H), 3.76 (s, 3H), 3.79-3.87/4.11-4.20/4.56 (m, m, s, 4H), 6.71 (d, 1H), 6.99 (s, 1H), 7.03 (s, 1H), 7.18 (s, 1H), 7.50-7.58 (m, 1H), 7.84 (d, 1H), 8.16 (s, 1H), 8.55-8.67 (m, 2H).

LC-MS (Method 1): R$_t$=0.83 min; MS (ESIpos): m/z=462 [M+H]$^+$.

Example 86

1-({1-(2-Chloropyridin-4-yl)-5-[3-methoxy-5-(trifluoromethoxy)phenyl]-1H-pyrazol-3-yl}carbonyl)imidazolidin-4-one

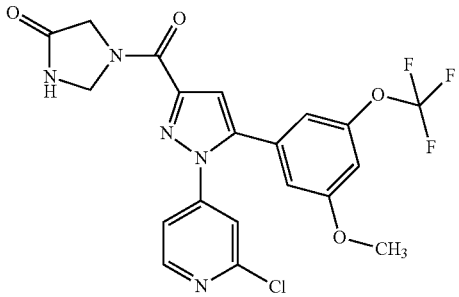 [SMILES: COc1cc(OC(F)(F)F)cc(-c2cc(C(=O)N3CNC(=O)C3)nn2-c2ccnc(Cl)c2)c1]

100 mg (0.24 mmol) of the compound of Example 57A is reacted analogously to the synthesis of the compound of Example 3 with 32 mg (0.26 mmol) of 4-imidazolinone-hydrochloride. 103 mg (88% of theory) of the title compound is obtained.

$^1$H-NMR (400 MHz, DMSO-d$_6$): δ=3.82 (s, 3H), 4.00/4.48 (s, 2H each), 4.91/5.36 (s, 2H each), 6.79-6.84 (m, 1H), 7.06-7.10 (m, 1H), 7.14-7.17 (m, 1H), 7.28/7.29 (s, 1H each), 7.37 (ddd, 1H), 7.57 (t, 1H), 8.47 (dd, 1H), 8.68/8.76 (s, 1H each).

LC-MS (Method 1): R$_t$=0.96 min; MS (ESIpos): m/z=482 [M+H]$^+$.

Example 87

4-({1-(2-Chloropyridin-4-yl)-5-[3-methoxy-5-(trifluoromethoxy)phenyl]-1H-pyrazol-3-yl}carbonyl)piperazin-2-one

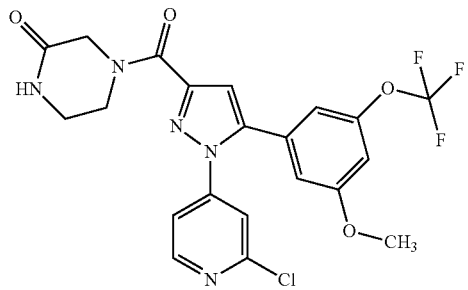 [SMILES: COc1cc(OC(F)(F)F)cc(-c2cc(C(=O)N3CCNC(=O)C3)nn2-c2ccnc(Cl)c2)c1]

31 mg (0.08 mmol) of the compound of Example 57A is reacted analogously to the synthesis of the compound of Example 4 with 8 mg (0.08 mmol) of 2-oxopiperazine. 37 mg (99% of theory) of the title compound is obtained.

$^1$H-NMR (400 MHz, DMSO-d$_6$): δ=3.24-3.53/3.76-3.88/4.08-4.19/4.51 (in, m, m, s, 9H), 6.83 (d, 11H), 7.07 (s, 1H), 7.14 (s, 1H), 7.17 (s, 1H), 7.31-7.37 (m, 1H), 7.50 (d, 1H), 8.18 (s, 1H), 8.43-8.50 (m, 1H).

LC-MS (Method 1): R$_t$=0.94 min; MS (ESIpos): m/z=496 [M+H]$^+$.

Example 88

3-{3-[(4-Oxoimidazolidin-1-yl)carbonyl]-1-(pyridin-3-yl)-1H-pyrazol-5-yl}-5-(trifluoromethoxy)benzonitrile

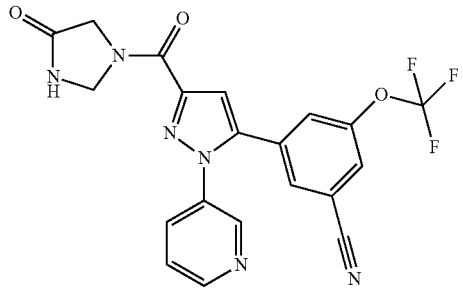 [SMILES: N#Cc1cc(OC(F)(F)F)cc(-c2cc(C(=O)N3CNC(=O)C3)nn2-c2cccnc2)c1]

98 mg (0.26 mmol) of the compound of Example 58A is reacted analogously to the synthesis of the compound of Example 1 with 35 mg (0.29 mmol) of 4-imidazolinone-hydrochloride. 80 mg (69% of theory) of the title compound is obtained.

$^1$H-NMR (400 MHz, DMSO-d$_6$): δ=4.00/4.44 (s, 2H each), 4.92/5.35 (s, 2H each), 7.40/7.41 (s, 1H each), 7.50-7.57 (m, 2H), 7.83-7.91 (m, 1H), 8.04-8.12 (m, 2H), 8.60-8.70/8.74 (m, s, 3H).

LC-MS (Method 1): R$_t$=0.85 min; MS (ESIpos): m/z=443 [M+H]$^+$.

Example 89

3-{3-[(3-Oxopiperazin-1-yl)carbonyl]-1-(pyridin-3-yl)-1H-pyrazol-5-yl}-5-(trifluoromethoxy)benzonitrile

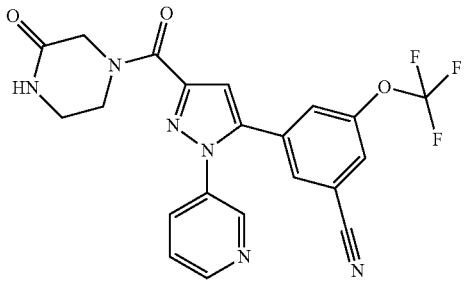 [SMILES: N#Cc1cc(OC(F)(F)F)cc(-c2cc(C(=O)N3CCNC(=O)C3)nn2-c2cccnc2)c1]

30 mg (0.08 mmol) of the compound of Example 58A is reacted analogously to the synthesis of the compound of Example 1 with 9 mg (0.09 mmol) of 2-oxopiperazine. 30 mg (83% of theory) of the title compound is obtained.

$^1$H-NMR (400 MHz, DMSO-d$_6$): δ=3.24-3.36 (m, 2H), 3.80-3.87/4.10-4.20/4.55 (m, m, s, 4H), 7.29 (s, 1H), 7.48-7.58 (m, 2H), 7.85 (d, 1H), 8.05/8.09/8.17 (s, 3H each).

LC-MS (Method 1): R$_t$=0.83 min; MS (ESIpos): m/z=457 [M+H]$^+$.

Example 90

1-{[5-(3-Bromo-5-fluorophenyl)-1-(pyridin-3-yl)-1H-pyrazol-3-yl]carbonyl}imidazolidin-4-one

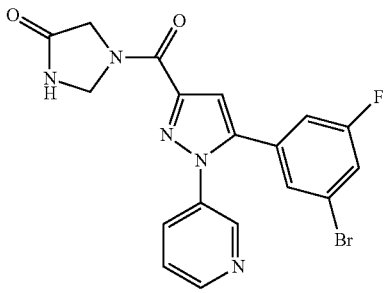 [SMILES: O=C1CN(C(=O)c2cc(-c3cc(F)cc(Br)c3)n(-c3cccnc3)n2)CN1]

75 mg (0.21 mmol) of the compound of Example 32A is reacted analogously to the synthesis of the compound of Example 3 with 27 mg (0.22 mmol) of 4-imidazolinone-hydrochloride. 68 mg (76% of theory) of the title compound is obtained.

$^1$H-NMR (400 MHz, DMSO-d$_6$): δ=3.99/4.44 (s, 2H each), 4.91/5.33 (s, 2H each), 7.25 (d, 1H), 7.29/7.30 (s, 1H each), 7.35-7.40 (m, 1H), 7.52-7.60 (m, 1H), 7.62-7.68 (m, 1H), 7.83-7.91 (m, 1H), 8.62-8.69/8.74 (m, s, 3H).

LC-MS (Method 1): R$_t$=0.85 min; MS (ESIpos): m/z=430 [M+H]$^+$.

Example 91

4-{[5-(3-Bromo-5-fluorophenyl)-1-(pyridin-3-yl)-1H-pyrazol-3-yl]carbonyl}piperazin-2-one

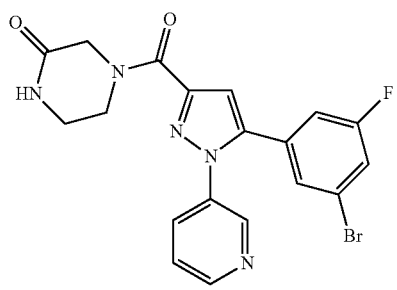 [SMILES: O=C1CN(C(=O)c2cc(-c3cc(F)cc(Br)c3)n(-c3cccnc3)n2)CCN1]

50 mg (0.14 mmol) of the compound of Example 32A is reacted analogously to the synthesis of the compound of Example 4 with 15 mg (0.15 mmol) of 2-oxopiperazine. 59 mg (96% of theory) of the title compound is obtained.

$^1$H-NMR (400 MHz, DMSO-d$_6$): δ=3.24-3.38/3.78-3.87/4.09-4.19/4.55 (m, m, m, s, 6H), 7.19 (s, 1H), 7.23 (d, 1H), 7.37 (s, 1H), 7.51-7.59 (m, 1H), 7.64 (d, 1H), 7.85 (d, 1H), 8.16 (s, 1H), 8.59-8.68 (m, 2H).

LC-MS (Method 1): R$_t$=0.82 min; MS (ESIpos): m/z=444 [M+H]$^+$.

Example 92

1-{[5-(3-Bromo-5-fluorophenyl)-1-(2-chloropyridin-4-yl)-1H-pyrazol-3-yl]carbonyl}imidazolidin-4-one

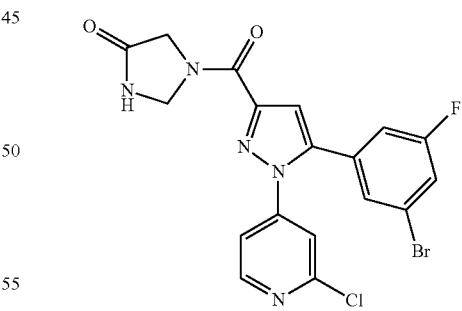

75 mg (0.17 mmol) of the compound of Example 33A is reacted analogously to the synthesis of the compound of Example 3 with 22 mg (0.18 mmol) of 4-imidazolinone-hydrochloride. 55 mg (71% of theory) of the title compound is obtained.

$^1$H-NMR (400 MHz, DMSO-d$_6$): δ=3.99/4.48 (s, 2H each), 4.91/5.36 (s, 2H each), 7.28/7.29 (s, 1H each), 7.30-7.39 (m, 2H), 7.49-7.53 (m, 1H), 7.64 (dd, 1H), 7.72 (dt, 1H), 8.48 (dd, 1H), 8.67/8.75 (s, 1H each).

LC-MS (Method 2): R$_t$=2.08 min; MS (ESIpos): m/z=464 [M+H]$^+$.

Example 93

4-{[5-(3-Bromo-5-fluorophenyl)-1-(2-chloropyridin-4-yl)-1H-pyrazol-3-yl]carbonyl}piperazin-2-one

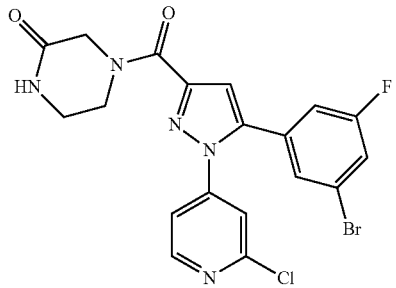 [SMILES: O=C1CN(C(=O)c2cc(-c3cc(F)cc(Br)c3)n(-c3ccnc(Cl)c3)n2)CCN1]

50 mg (0.13 mmol) of the compound of Example 33A is reacted analogously to the synthesis of the compound of Example 4 with 14 mg (0.14 mmol) of 2-oxopiperazine. 49 mg (81% of theory) of the title compound is obtained.

$^1$H-NMR (400 MHz, DMSO-d$_6$): δ=3.25-3.37 (m, 2H), 3.83/4.09 (t, 2H each), 4.15/4.50 (s, 2H each), 7.17 (s, 1H), 7.28-7.39 (m, 2H), 7.50 (s, 1H), 7.56 (d, 1H), 7.68-7.75 (m, 1H), 8.17 (s, 1H), 8.44-8.50 (m, 1H).

LC-MS (Method 2): R$_t$=2.04 min; MS (ESIpos): m/z=478 [M+H]$^+$.

Example 94

1-{[5-(3-Bromo-5-methoxyphenyl)-1-(pyridin-3-yl)-1H-pyrazol-3-yl]carbonyl}imidazolidin-4-one

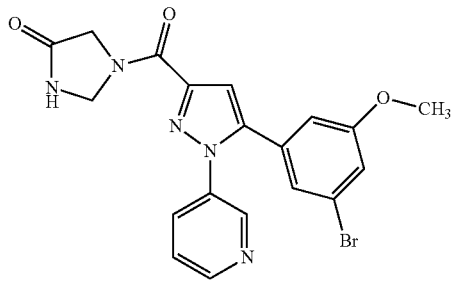 [SMILES: COc1cc(Br)cc(-c2cc(C(=O)N3CNC(=O)C3)nn2-c2cccnc2)c1]

80 mg (0.21 mmol) of the compound of Example 50A is reacted analogously to the synthesis of the compound of Example 1 with 29 mg (0.24 mmol) of 4-imidazolinone-hydrochloride. 76 mg (79% of theory) of the title compound is obtained.

$^1$H-NMR (400 MHz, DMSO-d$_6$): δ=3.70 (s, 3H), 3.99/4.44 (s, 2H each), 4.91/5.33 (s, 2H each), 6.84-6.87 (m, 1H), 7.04-7.08 (m, 1H), 7.19-7.22 (m, 1H), 7.24/7.25 (s, 1H each), 7.53-7.59 (m, 1H), 7.83-7.90 (m, 1H), 8.61-8.67/8.73 (m, s, 3H).

LC-MS (Method 1): R$_t$=0.86 min; MS (ESIpos): m/z=442 [M+H]$^+$.

Example 95

4-{([5-(3-Bromo-5-methoxyphenyl)-1-(pyridin-3-yl)-1H-pyrazol-3-yl]carbonyl}piperazin-2-one

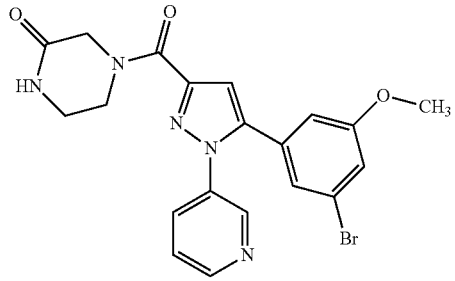 [SMILES: COc1cc(Br)cc(-c2cc(C(=O)N3CCNC(=O)C3)nn2-c2cccnc2)c1]

50 mg (0.13 mmol) of the compound of Example 50A is reacted analogously to the synthesis of the compound of Example 1 with 15 mg (0.15 mmol) of 2-oxopiperazine. 54 mg (88% of theory) of the title compound is obtained.

$^1$H-NMR (400 MHz, DMSO-d$_6$): δ=3.24-3.36 (m, 2H), 3.69 (s, 3H), 3.79-3.86/4.10-4.19/4.56 (m, m, s, 4H), 6.82-6.88 (m, 1H), 7.06 (s, 1H), 7.13 (s, 1H), 7.20 (s, 1H), 7.51-7.59 (m, 1H), 7.84 (d, 1H), 8.15 (s, 1H), 8.56-8.67 (m, 2H).

LC-MS (Method 1): R$_t$=0.84 min; MS (ESIpos): m/z=456 [M+H]$^+$.

Example 96

1-{[5-(3-Bromo-5-methoxyphenyl)-1-(2-chloropyridin-4-yl)-1H-pyrazol-3-yl]carbonyl}imidazolidin-4-one

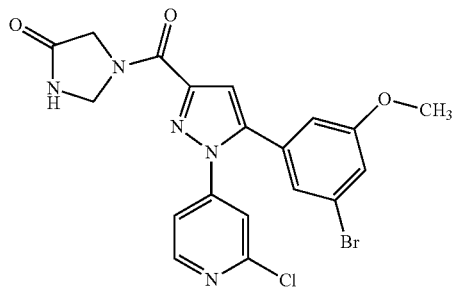 [SMILES: COc1cc(Br)cc(-c2cc(C(=O)N3CNC(=O)C3)nn2-c2ccnc(Cl)c2)c1]

80 mg (0.20 mmol) of the compound of Example 51A is reacted analogously to the synthesis of the compound of Example 1 with 26 mg (0.22 mmol) of 4-imidazolinone-hydrochloride. 70 mg (75% of theory) of the title compound is obtained.

$^1$H-NMR (400 MHz, DMSO-d$_6$): δ=3.75 (s, 3H), 3.99/4.48 (s, 2H each), 4.91/5.36 (s, 2H each), 6.96-7.00 (m, 1H), 7.14-7.18 (m, 1H), 7.22/7.23 (s, 1H each), 7.25 (t, 1H), 7.33 (ddd, 1H), 7.62 (dd, 1H), 8.47 (dd, 1H), 8.67/8.75 (s, 1H each).

Example 97

4-{[5-(3-Bromo-5-methoxyphenyl)-1-(2-chloropyridin-4-yl)-1H-pyrazol-3-yl]carbonyl}piperazin-2-one

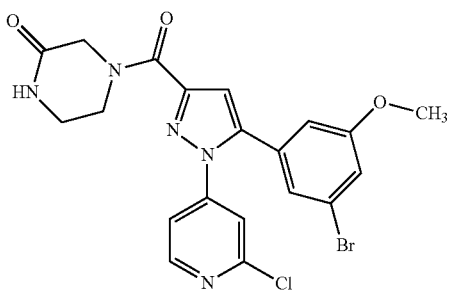 [SMILES: COc1cc(Br)cc(-c2cc(C(=O)N3CCNC(=O)C3)nn2-c2ccnc(Cl)c2)c1]

50 mg (0.12 mmol) of the compound of Example 51A is reacted analogously to the synthesis of the compound of Example 1 with 13 mg (0.14 mmol) of 2-oxopiperazine. 50 mg (84% of theory) of the title compound is obtained.

$^1$H-NMR (400 MHz, DMSO-d$_6$): δ=3.25-3.36 (m, 2H), 3.75 (s, 3H), 3.83/4.10 (t, 2H each), 4.15/4.50 (s, 2H each), 6.94-7.00 (m, 1H), 7.11 (s, 1H), 7.14-7.19 (m, 1H), 7.26-7.33 (m, 2H), 7.51-7.58 (m, 1H), 8.17 (s, 1H), 8.44-8.49 (m, 1H).

LC-MS (Method 1): R$_t$=0.94 min; MS (ESIpos): m/z=490 [M+H]$^+$.

Example 98

1-{[1-(3-Chloro-4-fluorophenyl)-5-(5-fluoropyridin-3-yl)-1H-pyrazol-3-yl]carbonyl}imidazolidin-4-one

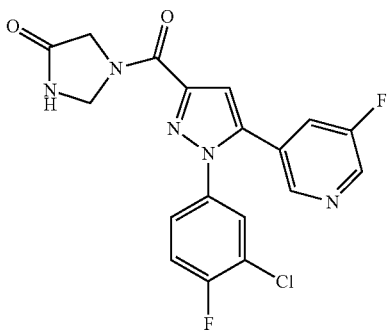 [SMILES: O=C1CN(C(=O)c2cc(-c3cncc(F)c3)n(-c3ccc(F)c(Cl)c3)n2)CN1]

0.16 ml (0.89 mmol) of N,N-diisopropylethylamine is added to a solution of 100 mg (0.30 mmol) of the compound of Example 60A, 40 mg (0.33 mmol) of 4-imidazolinone-hydrochloride, and 217 mg (0.42 mmol) of PYBOP in 2 ml of THF, and the mixture that is obtained is stirred for 16 hours at room temperature. The reaction mixture is concentrated by evaporation in a vacuum. The residue is diluted with acetonitrile, filtered over a Millipore spray filter, and separated by means of preparative HPLC (mobile solvent: acetonitrile/water gradient). Solvent is removed from the product-containing fractions in a rotary evaporator, and the residue is recrystallized from acetonitrile. 96 mg (80% of theory) of the title compound is obtained.

$^1$H-NMR (400 MHz, DMSO-d$_6$): δ=3.99/4.45 (s, 2H each), 4.91/5.33 (s, 2H each), 7.34 (d, 1H), 7.37-7.44 (m, 1H), 7.54 (dt, 1H), 7.75-7.81 (m, 1H), 7.83-7.88 (m, 1H), 8.34-8.38 (m, 1H), 8.63 (d, 1H), 8.64/8.74 (s, 1H each).

LC-MS (Method 1): R$_t$=0.79 min; MS (ESIpos): m/z=404 [M+H]$^+$.

Example 99

4-{[1-(3-Chloro-4-fluorophenyl)-5-(5-fluoropyridin-3-yl)-1H-pyrazol-3-yl]carbonyl}piperazin-2-one

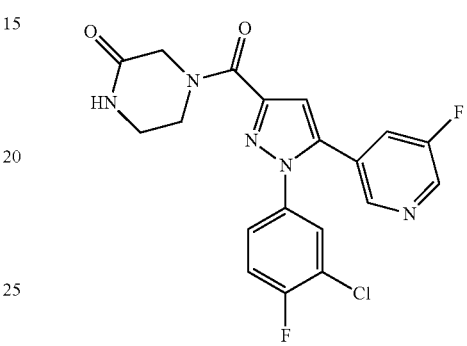

100 mg (0.30 mmol) of the compound of Example 60A is reacted analogously to the synthesis of the compound of Example 98 with 33 mg (0.33 mmol) of 2-oxopiperazine. 92 mg (74% of theory) of the title compound is obtained.

$^1$H-NMR (400 MHz, DMSO-d$_6$): δ=3.25-3.35/3.79-3.87/4.09-4.20/4.55 (m, m, m, s, 6H), 7.23 (s, 1H), 7.37-7.43 (m, 1H), 7.50-7.58 (m, 1H), 7.72-7.85 (m, 2H), 8.16 (s, 1H), 8.33-8.38 (m, 1H), 8.62 (d, 1H).

LC-MS (Method 1): R$_t$=0.77 min; MS (ESIpos): m/z=418 [M+H]$^+$.

Example 100

1-{[1-(3-Chloro-4-fluorophenyl)-5-(5-chloropyridin-3-yl)-1H-pyrazol-3-yl]carbonyl}imidazolidin-4-one

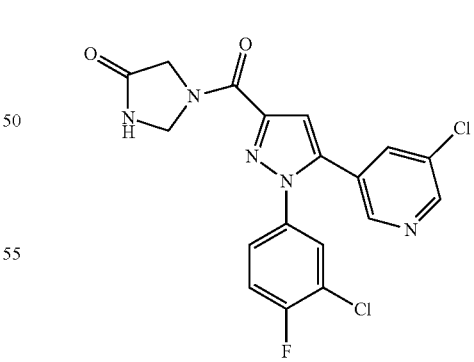

100 mg (0.28 mmol) of the compound of Example 61A is reacted analogously to the synthesis of the compound of Example 98 with 38 mg (0.31 mmol) of 4-imidazolinone-hydrochloride. 62 mg (52% of theory) of the title compound is obtained.

$^1$H-NMR (400 MHz, DMSO-d$_6$): δ=3.99/4.44 (s, 2H each), 4.91/5.33 (s, 2H each), 7.35 (d, 1H), 7.38-7.45 (m, 1H), 7.55 (dt, 1H), 7.84-7.89 (m, 1H), 7.95-7.99 (m, 1H), 8.40-8.43 (m, 1H), 8.64/8.73 (s, 1H each), 8.66 (d, 1H).

LC-MS (Method 1): $R_t$=0.85 min; MS (ESIpos): m/z=420 [M+H]$^+$.

Example 101

4-{[1-(3-Chloro-4-fluorophenyl)-5-(5-chloropyridin-3-yl)-1H-pyrazol-3-yl]carbonyl}piperazin-2-one

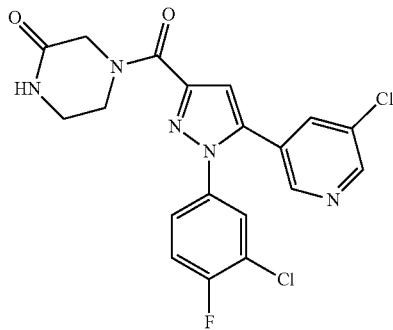 [SMILES: O=C1CN(C(=O)c2cc(-c3cncc(Cl)c3)n(-c3ccc(F)c(Cl)c3)n2)CCN1]

100 mg (0.28 mmol) of the compound of Example 61A is reacted analogously to the synthesis of the compound of Example 98 with 31 mg (0.31 mmol) of 2-oxopiperazine. 71 mg (58% of theory) of the title compound is obtained.

$^1$H-NMR (400 MHz, DMSO-d$_6$): δ=3.25-3.37/3.79-3.87/4.09-4.20/4.54 (m, m, m, s, 6H), 7.24 (s, 1H), 7.38-7.44 (m, 1H), 7.50-7.59 (m, 1H), 7.78-7.86 (m, 1H), 7.95 (t, 1H), 8.16 (s, 1H), 8.38-8.44 (m, 1H), 8.65 (d, 1H).

LC-MS (Method 1): $R_t$=0.83 min; MS (ESIpos): m/z=434 [M+H]$^+$.

Example 102

1-{[1-(3-Chloro-4-fluorophenyl)-5-(5-methoxypyridin-3-yl)-1H-pyrazol-3-yl]carbonyl}imidazolidin-4-one

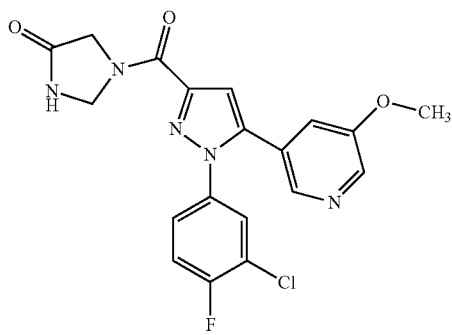 [SMILES: COc1cncc(-c2cc(C(=O)N3CNC(=O)C3)nn2-c2ccc(F)c(Cl)c2)c1]

0.12 ml (0.70 mmol) of N,N-diisopropylethylamine is added to a solution of 220 mg (0.23 mmol, 37% purity) of the compound of Example 64A, 57 mg (0.47 mmol) of 4-imidazolinone-hydrochloride, and 142 mg (0.38 mmol) of HATU in 6 ml of THF, and the mixture that is obtained is stirred for 20 hours at room temperature. After the further addition of 57 mg (0.47 mmol) of 4-imidazolinone-hydrochloride as well as 89 mg (0.23 mmol) of HATU, stirring is continued for 16 hours at 60° C. The crude product is separated by means of preparative HPLC (mobile solvent: acetonitrile/water gradient). 39 mg (35% of theory, 88% purity) of the title compound is obtained.

$^1$H-NMR (400 MHz, DMSO-d$_6$): δ=3.79 (s, 3H), 3.99/4.45 (s, 2H each), 4.91/5.34 (s, 2H each), 7.30 (d, 1H), 7.36-7.43 (m, 2H), 7.54 (dt, 1H), 7.84 (dd, 1H), 8.05 (dd, 1H), 8.31-8.35 (m, 1H), 8.65/8.74 (s, 1H each).

LC-MS (Method 1): $R_t$=0.78 min; MS (ESIpos): m/z=416 [M+H]$^+$.

Example 103

4-{[1-(3-Chloro-4-fluorophenyl)-5-(5-methoxypyridin-3-yl)-1H-pyrazol-3-yl]carbonyl}piperazin-2-one

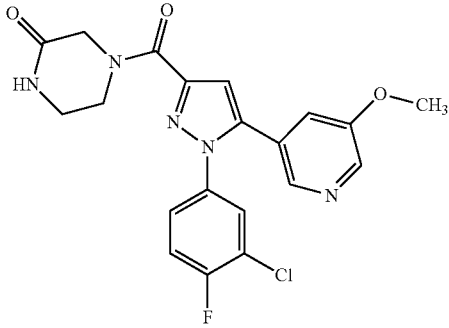 [SMILES: COc1cncc(-c2cc(C(=O)N3CCNC(=O)C3)nn2-c2ccc(F)c(Cl)c2)c1]

0.06 ml (0.32 mmol) of N,N-diisopropylethylamine is added to a solution of 150 mg (0.16 mmol, 37% purity) of the compound of Example 64A, 32 mg (0.32 mmol) of 2-oxopiperazine, and 97 mg (0.26 mmol) of HATU in 5 ml of THF, and the mixture that is obtained is stirred for 20 hours at room temperature. After the further addition of 32 mg (0.32 mmol) of 2-oxopiperazine, stirring is continued for 5 hours at 60° C. The crude product is separated by means of preparative HPLC (mobile solvent: acetonitrile/water gradient). The title compound is obtained in a quantitative yield.

$^1$H-NMR (400 MHz, DMSO-d$_6$): δ=3.24-3.33 (m, 2H), 3.78 (s, 3H), 3.80-3.86/4.11-4.20/4.56 (m, m, s, 4H), 7.19 (s, 1H), 7.35-7.42 (m, 2H), 7.54 (dt, 1H), 7.76-7.84 (m, 1H), 8.07 (d, 1H), 8.16 (s, 1H), 8.32 (d, 1H).

LC-MS (Method 1): $R_t$=0.76 min; MS (ESIpos): m/z=430 [M+H]$^+$.

Example 104

{1-(2-Chloropyridin-4-yl)-5-[3-fluoro-5-(trifluoromethoxy)phenyl]-1H-pyrazol-3-yl}(1,3-thiazolidin-3-yl)methanone

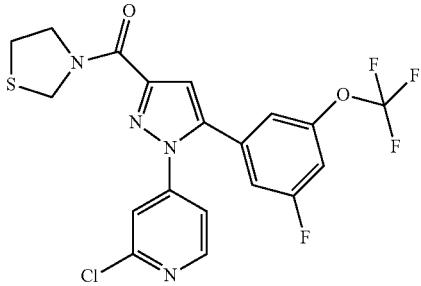 [SMILES: O=C(c1cc(-c2cc(F)cc(OC(F)(F)F)c2)n(-c2ccnc(Cl)c2)n1)N1CCSC1]

200 mg (0.55 mmol) of the compound of Example 35A is reacted analogously to the synthesis of the compound of Example 1 with 0.05 ml (0.60 mmol) of thiazolidine. 193 mg (80% of theory) of the title compound is obtained.

$^1$H-NMR (400 MHz, DMSO-d$_6$): δ=3.10 (dt, 2H), 3.88 (s, 1H), 4.22 (s, 1H), 4.70 (s, 1H), 5.04 (s, 1H), 7.03 (s, 1H), 7.28 (s, 1H), 7.42 (d, 1H), 7.49 (d, 1H), 7.54 (dd, 1H), 7.83-7.91 (m, 1H), 8.60-8.69 (m, 2H).

LC-MS (Method 7): R$_t$=1.07 min; MS (ESIpos): m/z=439 [M+H]$^+$.

Example 105

1-({1-(3-Chloro-4-fluorophenyl)-5-[5-(difluoromethoxy)pyridin-3-yl]-1H-pyrazol-3-yl}carbonyl)imidazolidin-4-one

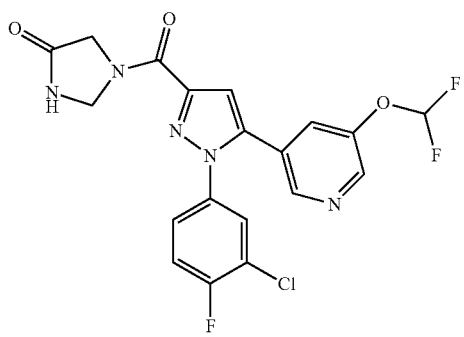 [SMILES: O=C1CN(C(=O)c2cc(-c3cncc(OC(F)F)c3)n(-c3ccc(F)c(Cl)c3)n2)CN1]

109 mg (0.28 mmol) of the compound of Example 65A is reacted analogously to the synthesis of the compound of Example 1 with 38 mg (0.31 mmol) of 4-imidazolinone-hydrochloride. 108 mg (84% of theory) of the title compound is obtained.

$^1$H-NMR (400 MHz, DMSO-d$_6$): δ=3.99/4.45 (s, 2H each), 4.91/5.33 (s, 2H each), 7.12/7.30/7.48 (s, 11-1 each), 7.35/7.36 (m, 1H), 7.38-7.46 (m, 1H), 7.55 (dt, 1H), 7.58-7.62 (m, 1H), 7.85 (dd, 1H), 8.39-8.44 (m, 1H), 8.52 (d, 1H), 8.64/8.74 (s, 11-1 each).

LC-MS (Method 1): R$_t$=0.84 min; MS (ESIpos): m/z=452 [M+H]$^+$.

Example 106

1-({1-(3-Chloro-4-fluorophenyl)-5-[5-(trifluoromethyl)pyridin-3-yl]-1H-pyrazol-3-yl}carbonyl)imidazolidin-4-one

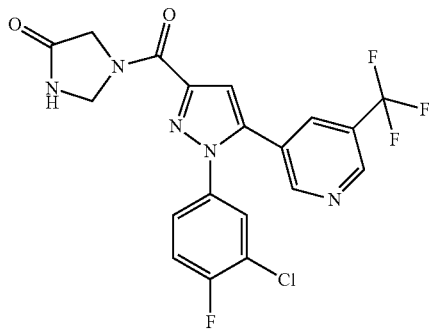 [SMILES: O=C1CN(C(=O)c2cc(-c3cncc(C(F)(F)F)c3)n(-c3ccc(F)c(Cl)c3)n2)CN1]

75 mg (0.19 mmol) of the compound of Example 66A is reacted analogously to the synthesis of the compound of Example 1 with 26 mg (0.21 mmol) of 4-imidazolinone-hydrochloride. 76 mg (86% of theory) of the title compound is obtained.

$^1$H-NMR (400 MHz, DMSO-d$_6$): δ=4.00/4.45 (s, 2H each), 4.92/5.34 (s, 2H each), 7.40-7.48 (m, 2H), 7.55 (dt, 1H), 7.85-7.90 (m, 1H), 8.11-8.15 (m, 1H), 8.64/8.74 (s, 1H each), 8.80 (s, 1H), 9.00 (s, 1H).

LC-MS (Method 1): R$_t$=0.89 min; MS (ESIpos): m/z=454 [M+H]$^+$.

Example 107

4-({(1-(3-Chloro-4-fluorophenyl)-5-[5-(trifluoromethyl)pyridin-3-yl]-1H-pyrazol-3-yl}carbonyl)piperazin-2-one

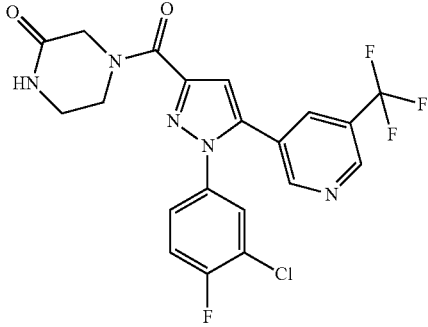 [SMILES: O=C1CN(C(=O)c2cc(-c3cncc(C(F)(F)F)c3)n(-c3ccc(F)c(Cl)c3)n2)CCN1]

75 mg (0.19 mmol) of the compound of Example 66A is reacted analogously to the synthesis of the compound of Example 1 with 21 mg (0.21 mmol) of 2-oxopiperazine. 75 mg (82% of theory) of the title compound is obtained.

$^1$H-NMR (400 MHz, DMSO-d$_6$): δ=3.25-3.3% [sic]/3.79-3.88/4.10-4.20/4.55 (m, m, m, s, 6H), 7.33 (s, 1H), 7.40-7.46 (m, 1H), 7.50-7.59 (m, 1H), 7.78-7.87 (m, 1H), 8.11/8.16 (s, 2H each), 8.78-8.84 (m, 1H), 9.00 (s, 1H).

LC-MS (Method 1): R$_t$=0.88 min; MS (ESIpos): m/z=468 [M+H]$^+$.

Example 108

1-({1-(3-Chlorophenyl)-5-[5-(trifluoromethyl)pyridin-3-yl]-1H-pyrazol-3-yl}carbonyl)imidazolidin-4-one

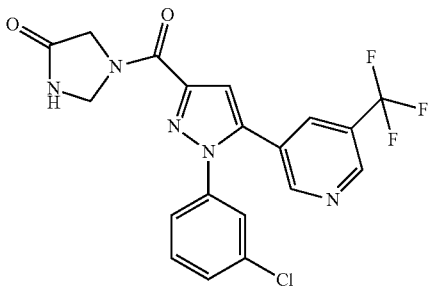

75 mg (0.20 mmol) of the compound of Example 67A is reacted analogously to the synthesis of the compound of Example 1 with 27 mg (0.22 mmol) of 4-imidazolinone-hydrochloride. 74 mg (83% of theory) of the title compound is obtained.

¹H-NMR (400 MHz, DMSO-d₆): δ=4.00/4.46 (s, 2H each), 4.92/5.35 (s, 2H each), 7.32-7.39 (m, 1H), 7.43-7.53 (m, 2H), 7.51/7.59 (s, 1H each), 7.66 (s, 1H), 8.08-8.16 (m, 1H), 8.64/8.74 (s, 1H each), 8.81 (s, 1H), 9.00 (s, 1H).

LC-MS (Method 1): R$_t$=0.88 min; MS (ESIpos): m/z=436 [M+H]⁺.

Example 109

4-({1-(3-Chlorophenyl)-5-[5-(trifluoromethyl)pyridin-3-yl]-1H-pyrazol-3-yl}carbonyl)piperazin-2-one

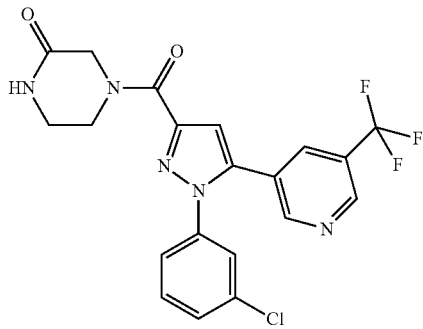 [SMILES: O=C1CN(C(=O)c2cc(-c3cncc(C(F)(F)F)c3)n(-c3cccc(Cl)c3)n2)CCN1]

75 mg (0.20 mmol) of the compound of Example 67A is reacted analogously to the synthesis of the compound of Example 1 with 22 mg (0.22 mmol) of 2-oxopiperazine. 76 mg (82% of theory) of the title compound is obtained.

¹H-NMR (400 MI-Hz, DMSO-d₆): δ=3.25-3.36/3.80-3.88/4.10-4.21/4.56 (m, m, m, s, 6H), 7.31-7.36 (m, 2H), 7.45-7.53 (m, 1H), 7.54-7.64 (m, 2H), 8.08 (s, 1H), 8.16 (s, 1H), 8.81 (s, 1H), 8.99 (s, 1H).

LC-MS (Method 1): R$_t$=0.86 min; MS (ESIpos): m/z=450 [M+H]⁺.

Example 110

1-{[5-(5-Chloro-6-fluoropyridin-3-yl)-1-(3-chlorophenyl)-1H-pyrazol-3-yl]carbonyl}imidazolidin-4-one

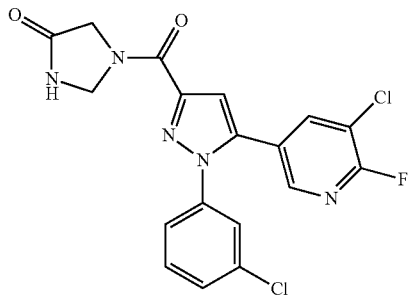 [SMILES: O=C1CN(C(=O)c2cc(-c3cnc(F)c(Cl)c3)n(-c3cccc(Cl)c3)n2)CN1]

21 mg (0.06 mmol) of the compound of Example 63A is reacted analogously to the synthesis of the compound of Example 1 with 8 mg (0.07 mmol) of 4-imidazolinone-hydrochloride. 15 mg (59% of theory) of the title compound is obtained.

¹H-NMR (400 MHz, DMSO-d₆): δ=3.99/4.45 (s, 2H each), 4.91/5.34 (s, 2H each), 7.28-7.38 (m, 2H), 7.45-7.61 (m, 2H), 7.68 (s, 1H), 8.11 (s, 1H), 8.22 (d, 1H).

LC-MS (Method 1): R$_t$=0.91 min; MS (ESIpos): m/z=420 [M+H]⁺.

Example 111

1-{[1-(3-Chloro-4-fluorophenyl)-5-(5-chloro-6-fluoropyridin-3-yl)-1H-pyrazol-3-yl]carbonyl}imidazolidin-4-one

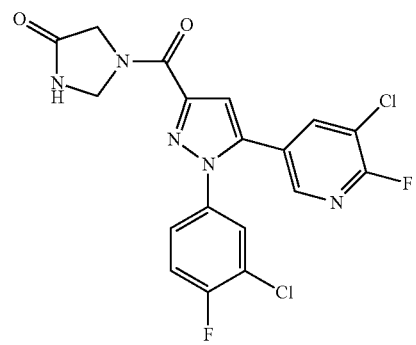 [SMILES: O=C1CN(C(=O)c2cc(-c3cnc(F)c(Cl)c3)n(-c3ccc(F)c(Cl)c3)n2)CN1]

16 mg (0.04 mmol) of the compound of Example 62A is reacted analogously to the synthesis of the compound of Example 1 with 6 mg (0.05 mmol) of 4-imidazolinone-hydrochloride. 11 mg (55% of theory) of the title compound is obtained.

¹H-NMR (400 MHz, DMSO-d₆): δ=3.99/4.44 (s, 2H each), 4.91/5.33 (s, 2H each), 7.33 (d, 1H), 7.37-7.45 (m, 1H), 7.53 (dt, 1H), 7.85-7.91 (m, 1H), 8.12 (s, 1H), 8.24 (dt, 1H), 8.64/8.74 (s, 1H each).

LC-MS (Method 1): R$_t$=0.93 min; MS (ESIpos): m/z=438 [M+H]⁺.

Example 112

1-{[1-(3-Chloro-4-fluorophenyl)-5-(2-chloropyridin-4-yl)-1H-pyrazol-3-yl]carbonyl}imidazolidin-4-one

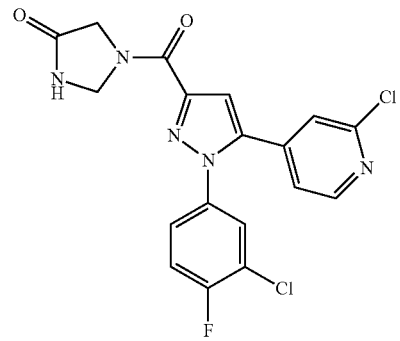 [SMILES: O=C1CN(C(=O)c2cc(-c3ccnc(Cl)c3)n(-c3ccc(F)c(Cl)c3)n2)CN1]

100 mg (0.28 mmol) of the compound of Example 68A is reacted analogously to the synthesis of the compound of Example 3 with 37 mg (0.30 mmol) of 4-imidazolinone-hydrochloride overnight at room temperature. 106 mg (89% of theory) of the title compound is obtained.

¹H-NMR (400 MHz, DMSO-d₆): δ=3.99/4.44 (s, 2H each), 4.91/5.32 (s, 2H each), 7.12-7.22 (m, 1H), 7.40-7.47 (m, 2H), 7.54-7.61 (m, 2H), 7.88-7.93 (m, 1H), 8.40 (d, 1H), 8.64/8.74 (s, 1H each).

LC-MS (Method 3): R$_t$=0.87 min; MS (ESIpos): m/z=420 [M+H]⁺.

Example 113

4-{[1-(3-Chloro-4-fluorophenyl)-5-(2-chloropyridin-4-yl)-1H-pyrazol-3-yl]carbonyl}piperazin-2-one

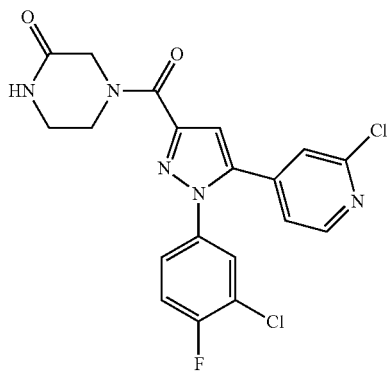 [SMILES: O=C1CN(C(=O)c2cc(-c3ccnc(Cl)c3)n(-c3ccc(F)c(Cl)c3)n2)CCN1]

100 mg (0.28 mmol) of the compound of Example 68A is reacted analogously to the synthesis of the compound of Example 4 with 30 mg (0.30 mmol) of 2-oxopiperazine. 111 mg (90% of theory) of the title compound is obtained.

¹H-NMR (400 MHz, DMSO-d₆): δ=3.25-3.36/3.78-3.87/4.07-4.18/4.53 (m, m, m, s, 6H), 7.19 (t, 1H), 7.33 (s, 1H), 7.40-7.46 (m, 1H), 7.53-7.61 (m, 2H), 7.82-7.90 (m, 1H), 8.16 (s, 1H), 8.40 (d, 1H).

LC-MS (Method 3): R$_t$=0.85 min; MS (ESIpos): m/z=434 [M+H]⁺.

Example 114

1-{[1-(3-Chlorophenyl)-5-(2-chloropyridin-4-yl)-1H-pyrazol-3-yl]carbonyl}imidazolidin-4-one

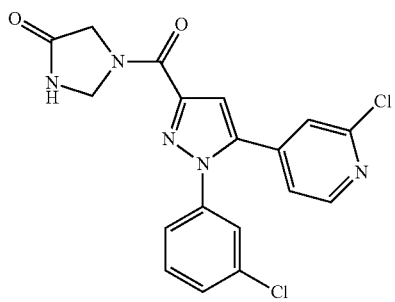 [SMILES: O=C1CN(C(=O)c2cc(-c3ccnc(Cl)c3)n(-c3cccc(Cl)c3)n2)CN1]

100 mg (0.30 mmol) of the compound of Example 69A is reacted analogously to the synthesis of the compound of Example 3 with 39 mg (0.32 mmol) of 4-imidazolinone-hydrochloride overnight at room temperature. 98 mg (81% of theory) of the title compound is obtained.

¹H-NMR (400 MHz, DMSO-d₆): δ=3.99/4.44 (s, 2H each), 4.91/5.33 (s, 2H each), 7.21 (d, 1H), 7.31-7.38 (m, 1H), 7.44 (d, 1H), 7.49-7.56 (m, 2H), 7.58-7.63 (m, 1H), 7.67-7.71 (m, 1H), 8.40 (d, 1H), 8.64/8.74 (s, 1H each).

LC-MS (Method 3): R$_t$=0.85 min; MS (ESIpos): m/z=402 [M+H]⁺.

Example 115

4-{[1-(3-Chlorophenyl)-5-(2-chloropyridin-4-yl)-1H-pyrazol-3-yl]carbonyl}piperazin-2-one

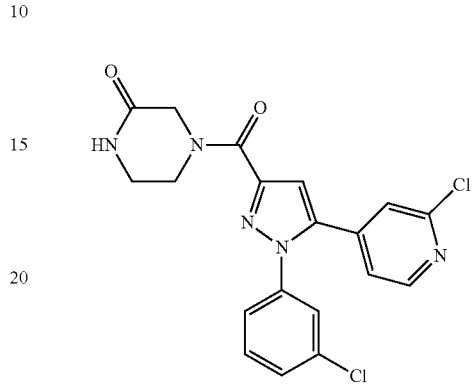

100 mg (0.30 mmol) of the compound of Example 69A is reacted analogously to the synthesis of the compound of Example 4 with 32 mg (0.32 mmol) of 2-oxopiperazine. 111 mg (890% of theory) of the title compound is obtained.

¹H-NMR (400 MHz, DMSO-d₆): δ=3.24-3.37/3.78-3.87/4.07-4.18/4.54 (m, m, m, s, 6H), 7.21 (t, 1H), 7.30-7.36 (m, 2H), 7.48-7.56 (m, 2H), 7.57-7.67 (m, 2H), 8.16 (s, 1H), 8.40 (d, 1H).

LC-MS (Method 3): R$_t$=0.83 min; MS (ESIpos): m/z=416 [M+H]⁺.

Example 116

4-({5-[3-Bromo-5-(trifluoromethoxy)phenyl]-1-[2-(trifluoromethyl)pyridin-4-yl]-1H-pyrazol-3-yl}carbonyl)piperazin-2-one

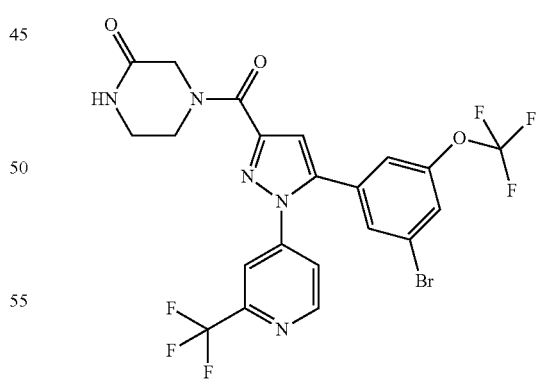

75 mg (0.15 mmol) of the compound of Example 47A is reacted analogously to the synthesis of the compound of Example 1 with 17 mg (0.17 mmol) of 2-oxopiperazine. 74 mg (84% of theory) of the title compound is obtained.

¹H-NMR (400 MHz, DMSO-d₆): δ=3.26-3.36/3.84/4.08/4.16/4.49 (m, t, t, s, s, 6H), 7.25 (s, 1H), 7.35 (d, 1H), 7.68-7.76 (m, 2H), 7.82-7.87 (m, 2H), 8.18 (s, 1H), 8.82-8.87 (m, 1H).

LC-MS (Method 7): $R_t$=1.03 min; MS (ESIpos): m/z=578 [M+H]$^+$.

Example 117

{5-[3-Bromo-5-(trifluoromethoxy)phenyl]-1-[2-(trifluoromethyl)pyridin-4-yl]-1H-pyrazol-3-yl}(1,3-thiazolidin-3-yl)methanone

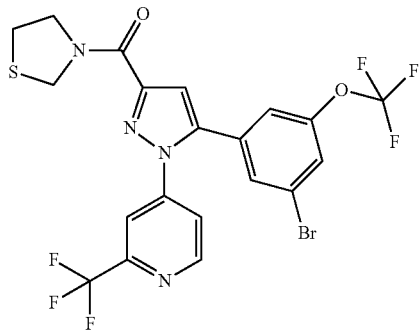 [SMILES: O=C(c1cc(-c2cc(Br)cc(OC(F)(F)F)c2)n(-c2ccnc(C(F)(F)F)c2)n1)N1CCSC1]

130 mg (0.26 mmol) of the compound of Example 47A is reacted analogously to the synthesis of the compound of Example 1 with 26 mg (0.29 mmol) of thiazolidine. 105 mg (71% of theory) of the title compound is obtained.

$^1$H-NMR (400 MHz, DMSO-d$_6$): δ=3.10/3.15 (t, 2H each), 3.88/4.21 (s, 2H each), 4.71/5.04 (s, 2H each), 7.33 (d, 2H), 7.72-7.81 (m, 2H), 7.85 (d, 2H), 8.85 (d, 1H).

LC-MS (Method 7): $R_t$=1.28 min; MS (ESIpos): m/z=567 [M+H]$^+$.

B) EVALUATION OF PHYSIOLOGICAL EFFECTIVENESS

Abbreviations

DMSO Dimethyl sulfoxide
FCS Fetal calf serum (Biochrom AG, Berlin, Germany)
PBS Phosphate-buffered saline
MOI Multiplicity of infection
MTP Microtiter plate
ELISA Enzyme-linked immunosorbent assay The suitability of the compounds according to the invention for treatment of diseases caused by retroviruses can be shown in the following assay systems:
In-Vitro Assays
Biochemical Reverse Transcriptase Assay The "Reverse Transcriptase Assay, colorimetric" (Roche Diagnostics GmbH, Mannheim, Germany) is used according to manufacturers' instructions. The test substances are dissolved in DMSO and used in diluted form in the test in the five steps (DMSO final concentration: 1%). The resulting values of the photometric analysis (405/492 nm) are smaller than 0.1 in the negative control (batch without reverse transcriptase) and are in the range of 1.5 in the positive control (batch without test substance). The IC$_{50}$ values of the test substances are determined as the concentration of the test substance dilution, in which the measured optical density is 50% of the positive control.

It is found that the compounds according to the invention inhibit the reverse transcriptase activity. In this case, the IC$_{50}$ values are in the range of 0.05-0.85 μM. For example, the following values were measured: IC$_{50}$ (Example 28)=0.213 μM, IC$_{50}$ (Example 49)=0.758 μM, IC$_{50}$ (Example 58)=0.056 μM, and IC$_{50}$ (Example 83)=0.065 μM.

Luminescence Reduction Assay

For this assay, HIV-1$_{NL4-3}$ reporter viruses are used, which carry the luciferase164 gene (lu164) instead of the nef gene. The viruses are generated by transfection of 293T cells with the corresponding proviral pNL4-3 plasmid (Lipofectamine Reagent, Invitrogen, Karlsruhe, Germany). Starting from the proviral plasmid-DNA, viruses with defined resistance mutations in the reverse transcriptase gene are produced with the "QuikChange II XL Site-Directed Mutagenesis Kit" (Stratagene, Cedar Creek, Tex., USA). Among other things, the following mutations are generated: A98G, A98G-K103N-V108I, A98S, F227C, F227L, G190A, G190S, K101E, K101Q-K103N, K103N, K103N-F227L, K103N-G190A, K103N-G190S, K103N-M230L, K103N-N348I, K103N-P225H, K103N-V108I, K103N-V108I-P225H, K103N-V179F-Y181C, K103N-Y181C, K103N-Y181C-G190A, L100I, L100I-K103N, L100I-K103N-V179I-Y181C, L100I-K103N-Y181C, L234I, N348I, P225H, P236L, V106A, V106A-E138K, V106A-F227C, V106A-F227L, V106I, V106I-Y188L, V106M, V108I, V179F-Y181C, V179I, V179I-Y181C, Y181C, Y181C-G190A, Y181C-M230L, Y181I, Y188L. MT4 cells infected with these reporter viruses (NIH AIDS Research and Reference Reagent Program) secrete luciferase into the medium, which makes possible the luminometric quantification of the virus replication.

For the batch of a 96-well MTP, 3 million MT4 cells are pelletized, suspended in 1 ml of RPMI 1640 medium without phenol red (Invitrogen, Karlsruhe, Germany)/10% FCS/2 mmol of L-glutamine/1% Pen/Strep (Invitrogen, Karlsruhe, Germany), and incubated together with a suitable amount of the corresponding HIV-1$_{NL4-3}$ reporter virus for 2 hours at 37° C. (pellet infection). Non-adsorbed viruses are then washed out with PBS, the infected cells are pelletized again, and suspended in 8 ml of RPM 11640 medium without phenol red/2% or 10% FCS/2 mmol of L-glutamine/1% Pen/Strep. Therefrom, 80 μl per well is pipetted into a white 96-well MTP in 20 μl of test substance in a suitable dilution. In order to avoid boundary effects, the edge wells of the MTP are not used for substance dilutions. The second vertical row of the MTP contains only infected cells (virus control), and the eleventh vertical row contains only non-infected cells (cell control) in each case in RPMI 1640 medium without phenol red/2% or 10% FCS/2 mmol of L-glutamine/1% Pen/Strep. The other wells of the MTP contain the compounds according to the invention in different concentrations starting from the third vertical row, from which dilution of the test substances is carried out 3$^7$ times in three steps up to the tenth vertical row. The test substances are dissolved in DMSO, whereby the DMSO final concentration in the test batch is ultimately 1%. The test batches are incubated for 5 days at 37° C./5% CO$_2$, and are luminometrically evaluated after the addition of 15 μl of Lu164-buffer (65 mmol of NaCl, 300 mmol of MES, pH 5.8, 5 mmol of glutathione and 1:200 coelenterazine (5 mg/ml in 30 μM of glutathione/DMSO) (P.J.K. GmbH, Kleinblittersdorf, Germany)). In the virus control, the resulting values are in the range of 1 million RLUs (relative light units), and in the cell control, the resulting values are 300 to 400 RLUs. The EC$_{50}$ values of the test substances are determined as the concentration of the treated infected cells, in which the virus replication measured in RLUs is 50% of the untreated infected cells.

It is found that the compounds according to the invention inhibit HIV replication. Experimental data are summarized in Table A.

PBL-und AlamarBlue Viability Assay

Primary human blood lymphocytes (PBLs) are isolated from blood via Ficoll-Paque Leucosep tubes (Greiner Bio-One, Frickenhausen, Germany) and stimulated in RPMI 1640 medium (Invitrogen, Karlsruhe, Germany)/10% FCS/2 mmol of L-glutamine/1% Pen/Strep with phytohaemagglutinin (90 µg/ml) and interleukin-2 (40 U/ml) for 3 days.

For the batch of a 96-well MTP, 3 million PBLs are pelletized, suspended in 1 ml of RPMI 1640 medium/10% FCS/2 mmol of L-glutamine/1% Pen/Strep, and incubated together with a suitable amount of HIV-1$_{LAI}$ (NIH AIDS Research & Reference Reagent Program, Germantown, USA) for 2 hours at 37° C. (pellet infection). Non-adsorbed viruses are then washed out with PBS, the infected cells are pelletized again, and suspended in 18 ml of RPMI 1640 medium/10% FCS/2 mmol of L-glutamine/1% Pen/Strep/interleukin-2 (40 U/ml). Therefrom, 180 µl per well is pipetted into a white 96-well MTP in 20 µl of test substance in a suitable dilution. As an alternative, after preparation of the substance dilutions, the HIV is added by pipetting in the MTP together with the cells and is no longer washed out (supernatant infection). In order to avoid boundary effects, the edge wells of the MTP are not used for substance dilutions. The second vertical row of the MTP contains only infected cells (virus control), and the eleventh vertical row contains only non-infected cells (cell control) in each case in RPMI 1640 medium/10% FCS/2 mmol of L-glutamine/1% Pen/Strep/interleukin-2 (40 U/ml). The other wells of the MTP contain the compounds according to the invention in different concentrations starting from the third vertical row, from which dilution of the test substances is carried out $3^7$ times in three steps up to the tenth vertical row. The test substances are dissolved in DMSO, whereby the DMSO final concentration in the test batch is ultimately 1%. The test batches are incubated at 37° C./5% $CO_2$. After 5 and 7 days, in each case 50 µl of cell-free supernatant is drawn off from each well in order to determine the amount of p24 contained by means of p24 ELISA (HIV-1 $p_{24}{}^{CA}$ Antigen Capture Assay Kit, NCI-Frederick Cancer Research and Development Center, Frederick, USA). From the resulting values of the photometric analysis (450/620 nm), the $EC_{50}$ values of the test substances are determined as the concentration of the treated infected cells, in which the amount of p24 is 50% of the untreated infected cells.

As an alternative, MT4 cells are used for testing test substances instead of PBLs. HIV-1$_{LAI}$-infected MT4 cells (MOI 0.01, supernatant infection) are incubated according to the above-described pattern in RPMI 1640 medium with 2% or 10% FCS/2 mmol of L-glutamine/1% Pen/Strep in the presence of test substances for 5 days at 37° C./5% $CO_2$ (20 µl of substance dilution and 80 µl of cells/virus per well). Then, 10 µl of AlamarBlue (Invitrogen, Karlsruhe, Germany) is added to each well, and MTPs are incubated for 3 hours at 37° C., before the fluorimetric analysis is done (544/590 nm). The resulting values are approximately 30,000 in the case of untreated, non-infected cells, and approximately 6,000 in the case of untreated infected cells. In the low concentration range, the $EC_{50}$ values of the test substances are determined as the concentration of the treated infected cells, in which the fluorescence is 50% of the untreated non-infected cells (in each case relative to the values of the untreated infected cells). In addition, in the high concentration range, the $CC_{50}$ values of the test substances are determined as the concentration of the treated infected cells, in which the fluorescence is 50% of the untreated, non-infected cells (in each case relative to the values of the untreated infected cells).

It is found that the compounds according to the invention inhibit HIV replication. Experimental data are summarized in Table A.

Assay for Determining the Cytotoxic Action of the Test Substances

To determine the cytotoxic action of the test substances in non-infected cells, the substances are pipetted in corresponding concentrations into translucent 96-well MTPs and incubated with non-infected cells (e.g., H9, PBLs, THP-1, MT4, CEM, Jurkat) (analogously to the above-described assays). After 5 days, ¹⁄₁₀ volume of AlamarBlue is added to the test batches per well, and the MTPs are incubated for 3 hours at 37° C. Then, the fluorimetric analysis (544/590 nm) is carried out. In the case of non-treated cells, the resulting values lie between 20,000 and 40,000, depending on the type of cell. The $CC_{50}$ values of the test substances are determined as the concentration of the treated cells, in which the fluorescence is 50% of the untreated cells.

TABLE A

| Example | $EC_{50}$ (µM) MT4 Cells HIV-1$_{NL4-3}$ Wild Type 2% FCS | $EC_{50}$ (µM) MT4 Cells HIV-1$_{NL4-3}$ K103N-Y181C 2% FCS | $EC_{50}$ (µM) MT4 Cells HIV-1$_{LAI}$ Wild Type 10% FCS |
|---|---|---|---|
| 1 | 0.345 | >3.300 | >3.300 |
| 2 | 0.272 | >3.300 | >3.300 |
| 3 | 0.006 | 0.067 | 0.028 |
| 4 | 0.036 | 0.132 | 0.108 |
| 5 | 0.023 | 1.319 | 0.533 |
| 6 | 0.054 | 1.356 | 0.201 |
| 6-1 | 0.255 | >3.300 | 1.488 |
| 6-2 | 0.007 | 0.986 | 0.112 |
| 7 | 0.010 | 0.018 | 0.064 |
| 8 | 0.060 | 0.290 | 0.205 |
| 9 | 0.035 | 0.320 | 0.149 |
| 10 | 0.149 | >3.300 | 1.709 |
| 11 | 0.007 | 0.061 | 0.057 |
| 12 | 0.189 | 0.377 | 1.795 |
| 13 | 0.323 | 0.880 | 1.340 |
| 14 | 0.005 | 0.067 | 0.096 |
| 15 | 0.018 | 0.452 | 0.151 |
| 16 | 0.055 | 0.339 | 0.490 |
| 17 | 0.248 | >3.300 | 3.666 |
| 18 | 0.284 | >3.300 | >3.300 |
| 19 | 0.152 | >3.300 | 2.505 |
| 20 | 0.162 | 1.385 | 1.458 |
| 21 | 0.092 | 0.436 | 0.397 |
| 22 | 0.375 | >3.300 | 3.182 |
| 23 | 0.439 | >3.300 | >3.300 |
| 24 | 0.066 | >3.300 | 0.668 |
| 25 | 0.004 | 0.040 | 0.011 |
| 26 | 0.120 | 0.071 | >3.300 |
| 27 | 0.098 | 0.114 | >3.300 |
| 28 | 0.005 | 0.005 | 0.044 |
| 29 | 0.012 | 0.032 | 0.097 |
| 30 | 0.033 | 0.181 | 0.794 |
| 31 | 0.017 | 0.045 | 0.180 |
| 31-1 | 0.084 | 0.981 | 0.820 |
| 31-2 | 0.010 | 0.041 | 0.336 |
| 32 | 0.007 | 0.014 | 0.083 |
| 33 | 0.069 | 0.299 | 1.016 |
| 34 | 0.010 | 0.003 | 0.098 |
| 35 | 0.042 | 0.010 | 0.232 |
| 36 | 0.149 | 0.080 | 2.368 |
| 37 | 0.004 | 0.005 | 2.322 |
| 38 | 0.023 | 0.007 | 1.220 |
| 39 | 0.009 | 0.007 | 0.062 |
| 40 | 0.013 | 0.044 | 0.213 |
| 41 | 0.042 | 0.087 | 0.991 |
| 42 | 0.018 | 0.028 | 0.247 |
| 43 | 0.103 | 0.529 | 0.751 |
| 44 | 0.018 | 0.020 | 0.274 |
| 45 | 0.095 | 0.232 | 0.550 |
| 46 | 0.007 | 0.007 | 0.097 |

TABLE A-continued

| Example | EC$_{50}$ (μM) MT4 Cells HIV-1$_{NL4-3}$ Wild Type 2% FCS | EC$_{50}$ (μM) MT4 Cells HIV-1$_{NL4-3}$ K103N-Y181C 2% FCS | EC$_{50}$ (μM) MT4 Cells HIV-1$_{LAI}$ Wild Type 10% FCS |
|---|---|---|---|
| 47 | 0.112 | 0.031 | 1.159 |
| 48 | 0.010 | 0.007 | 0.111 |
| 49 | 0.008 | 0.038 | 0.230 |
| 50 | 0.102 | 0.167 | 1.860 |
| 51 | 0.249 | 1.051 | 1.930 |
| 52 | 0.376 | 0.740 | >3.300 |
| 53 | 0.023 | 0.008 | 0.302 |
| 54 | 0.323 | 0.387 | 1.683 |
| 55 | 0.003 | 0.010 | 0.104 |
| 56 | 0.002 | 0.005 | 0.011 |
| 57 | 0.016 | 0.050 | 0.183 |
| 58 | 0.204 | 1.091 | 0.955 |
| 59 | 0.256 | 1.108 | 2.781 |
| 60 | 0.077 | 0.621 | 0.997 |
| 60-1 | 0.431 | >3.300 | >3.300 |
| 60-2 | 0.084 | 0.446 | 0.797 |
| 61 | 0.092 | 0.767 | 0.600 |
| 62 | 0.044 | 0.066 | 0.352 |
| 63 | 0.354 | 0.892 | 2.076 |
| 64 | 0.103 | 0.771 | 1.555 |
| 65 | 0.026 | 0.291 | 0.491 |
| 66 | 0.013 | 0.058 | 0.083 |
| 67 | 0.051 | 0.721 | 0.641 |
| 68 | 0.062 | 0.193 | 0.326 |
| 69 | 0.320 | 1.138 | 1.981 |
| 70 | <0.002 | 0.315 | 0.034 |
| 71 | 0.013 | >3.300 | 0.246 |
| 72 | 0.038 | >3.300 | 0.585 |
| 73 | 0.018 | 0.951 | 0.243 |
| 74 | 0.004 | 0.302 | 0.066 |
| 75 | 0.272 | >3.300 | >3.300 |
| 76 | 0.014 | 0.019 | 0.207 |
| 77 | 0.067 | 0.364 | 0.861 |
| 78 | 0.078 | 0.277 | 0.367 |
| 79 | 0.038 | 0.125 | 0.244 |
| 80 | 0.164 | 0.075 | 2.788 |
| 81 | 0.003 | 0.008 | 0.015 |
| 82 | 0.016 | 0.307 | 0.348 |
| 83 | 0.008 | 0.168 | 0.089 |
| 84 | 0.010 | 0.008 | 0.048 |
| 85 | 0.050 | 0.123 | 0.302 |
| 86 | 0.014 | 0.011 | 0.065 |
| 87 | 0.110 | 0.068 | 0.618 |
| 88 | 0.015 | 0.026 | 0.186 |
| 89 | 0.258 | 0.523 | 0.129 |
| 90 | 0.003 | 0.033 | 0.011 |
| 91 | 0.006 | 0.392 | 0.055 |
| 92 | 0.005 | 0.033 | 0.026 |
| 93 | 0.016 | 0.256 | 0.137 |
| 94 | <0.002 | 0.012 | 0.006 |
| 95 | 0.005 | 0.054 | 0.033 |
| 96 | 0.004 | 0.020 | 0.016 |
| 97 | 0.013 | 0.116 | 0.068 |
| 98 | 0.018 | 0.032 | 0.056 |
| 99 | 0.113 | 1.308 | 0.258 |
| 100 | 0.005 | 0.009 | 0.010 |
| 101 | 0.016 | 0.088 | 0.034 |
| 102 | 0.026 | 0.022 | 0.111 |
| 103 | 0.205 | 0.375 | 0.785 |
| 104 | 0.580 | 3.300 | >3.300 |
| 105 | 0.018 | 0.007 | 0.116 |
| 106 | 0.082 | 0.120 | 0.084 |
| 107 | 0.299 | 1.278 | 0.263 |
| 108 | 0.052 | 0.093 | 0.036 |
| 109 | 0.232 | 0.768 | 0.246 |
| 110 | 0.024 | 0.039 | 0.025 |
| 111 | 0.030 | 0.173 | 0.024 |
| 112 | 0.016 | 0.030 | 0.079 |
| 113 | 0.025 | 0.298 | 0.233 |
| 114 | 0.007 | 0.171 | 0.063 |
| 115 | 0.027 | 1.086 | 0.352 |
| 116 | 0.648 | 0.896 | >3.300 |
| 117 | 1.281 | 3.300 | >3.300 |

In-Vivo Assay

Animal Model:

NOD Scid mice, in general 5- to 6-weeks old, are purchased from commercial suppliers (e.g., Taconic or Jackson Laboratory). The animals are kept in isolators under sterile conditions (including bedding and food).

A defined number of cells (e.g., $5 \times 10^6$ T cells (e.g., C8166)) are infected with HIV with a suitable MOI (e.g., 0.01 TCID$_{50}$). The infected cells are introduced into collagen sponges. The sponges that are pretreated in this way are implanted in the mice under the skin of the back. The mice are treated one or more times daily by oral, intraperitoneal, subcutaneous or intravenous means, whereby the first treatment can be before the implantation. In general, the treatment groups comprise 10 mice. At least one group is treated with a placebo, at least one group with a substance that is known to be effective (=positive control), and in general several groups with the substance according to the invention. The daily dose of the substance according to the invention is between 0.01 mg and 100 mg per kg of body weight. The formulation of the substances is carried out in 2% DMSO/98% tylose (0.5% solution in PBS) or another suitable mixture, which supports the solubility of the substances. In general, the treatment period is 4.5 days. After the last administration of substance, the animals are killed, and the sponges are removed. The virus-infected cells are recovered from the sponge by collagenase digestion.

Total-RNA, which is checked for the content of virus-RNA in quantitative PCR, is recovered from the cells. The amount of virus-RNA is normalized based on the amount of a housekeeping gene (e.g., GAPDH). The amount of HIV-RNA is determined after substance treatment in comparison to the placebo-treated control group. If HIV, which carries a luciferase, was used, a luciferase measurement can be performed in addition or alternatively. In this case, the amount of HIV is determined based on the level of the luciferase signal, since in this case, it is used as a measurement of the virus replication. The statistical analysis is carried out by means of suitable computer programs, e.g., Graph Pad Prism.

B) EVALUATION OF THE PHARMACOKINETIC PROPERTIES

In-Vivo Studies

To determine the in-vivo pharmacokinetics, the test substances are administered intravenously and orally to mice, rats, rabbits or dogs. In the case of intravenous administration, a dose of 0.5-1 mg/kg is used, and in the case of oral administration, a dose of 1-10 mg/kg is used. The test substances are formulated in 1% DMSO/99% plasma for intravenous administration and in 2% DMSO/98% tylose (0.5% solution in PBS), Labrafil M1944 CS or PEG 400 with ethanol and water in varying proportions in the case of oral administration.

The quantitative determination of the substances is done from the animal plasma obtained and from calibrated test pieces that are set in plasma. The plasma proteins are removed by precipitation with acetonitrile (ACN). Subsequently, the samples are separated by means of HPLC with use of different columns and analyzed by mass spectroscopy. The analysis of the plasma concentration time plot is carried out with the application of an internal standard and with use of a validated kinetics analysis program.

Plasma Stability

The plasma of the different species (CD-1 mouse, Wistar rat and human) that is used is freshly obtained or commercially available by drawing blood in Li-heparin-coated monovettes and subsequent centrifuging. To determine the plasma stability of the test substances, 1 μM of solution each is incubated at 37° C. At various times, over an interval of up to 90 minutes, samples are removed in the incubation vessel. The samples that are obtained are precipitated with ACN in order to stop the reaction and to separate the plasma proteins. The samples are analyzed in an equivalent manner to the in-vivo studies.

Microsomal and Hepatocyte Incubations

Incubations are performed at 37° C. with liver microsomes of various species (CD-1 mouse, Wistar rat, and human). The incubation mixtures in each case contain 1 μM of test substance as well as 0.5 mg/ml of microsomal protein. In addition, 0.05 M of phosphate buffer (pH=7.4), 1 mmol of EDTA, 5 mmol of glucose-6-phosphate, and 1.5 U/ml of glucose-6-phosphate dehydroxygenase from *Leuconostoc Mesenteroides* are added. The microsomal incubation is started by adding NADPH (final concentration: 1 mmol).

To determine the metabolic stability of the test substances in CD-1 mouse hepatocytes, $3 \times 10^5$ cells/ml are used. To determine the metabolic stability of test substances in hepatocytes of Wistar rats and humans, $1 \times 10^6$ cells/ml are used. Equivalent to the microsomal assay, in each case 1 M of test substance is added to the hepatocytes.

In time intervals between 0 and 90 minutes, 100 μl is removed from the respective incubation batch and mixed with ACN in order to stop the enzymatic reactions. After centrifuging, the samples are analyzed by means of LC-MS/MS; $CL'_{intrinsic}$ [ml/(min·kg)] and half-life [min] are reported.

C) EMBODIMENTS OF PHARMACEUTICAL COMPOSITIONS

The compounds according to the invention can be converted into pharmaceutical preparations as follows:

Solution That Can be Administered Orally

Composition and Production

Example 1

2% DMSO/98% Tylose (0.5% Solution in PBS)

The compound according to the invention is completely dissolved in the calculated volume of DMSO, and the solution is then suspended in tylose. The suspension is mixed by, e.g., stirring, an ultrasound bath, or an Ultra-Turrax until a homogeneous suspension or solution is produced.

Example 2

100% Labrafil M 1944 CS

The compound according to the invention is suspended in the calculated volume of Labrafil M 1944 CS. The suspension is mixed by, e.g., stirring, an ultrasound bath, or an Ultra-Turrax until a homogeneous suspension or solution is produced.

i.v. Solution

Composition and Production

Example 3

1% DMSO/99% Plasma

The compound according to the invention is completely dissolved in the calculated volume of DMSO, and the solution is then suspended in plasma. The suspension is mixed until a solution is produced.

The invention claimed is:
1. A compound of Formula (I):

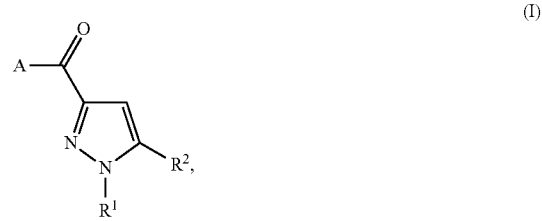

in which
$R^1$ stands for phenyl or pyridyl,
whereby phenyl is substituted with 1 to 3, substituents, whereby the substituents are selected independently of one another from: halogen, hydroxy, amino, cyano, nitro, $(C_1-C_4)$-alkyl, $(C_3-C_6)$-cycloalkyl, $(C_1-C_4)$-alkylamino and $(C_1-C_4)$-alkoxy,
in which
the alkyl, cycloalkyl, alkylamino and alkoxy groups are optionally substituted in one to three places, in the same way or differently, with radicals selected from: halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl, and 4- to 7-membered heterocyclyl,
and
whereby pyridyl is optionally substituted with 1 or 2 substituents, whereby the substituents, independently of one another, are selected from halogen, hydroxy, amino, cyano, nitro, $(C_1-C_4)$-alkyl, $(C_3-C_6)$-cycloalkyl, and $(C_1-C_4)$-alkoxy, and whereby the nitrogen atom of the pyridyl can optionally form an N-oxide,
in which
the alkyl, cycloalkyl and alkoxy groups are optionally substituted in one to three places, in the same way or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl, and 4- to 7-membered heterocyclyl,
$R^2$ stands for phenyl or pyridyl,
whereby phenyl is substituted with 1 to 3 substituents, whereby the substituents, independently of one another, are selected from: halogen, hydroxy, amino, cyano, nitro, $(C_1-C_4)$-alkyl, $(C_3-C_6)$-cycloalkyl, $(C_1-C_4)$-alkylamino, and $(C_1-C_4)$-alkoxy,
in which
the alkyl, cycloalkyl, alkylamino and alkoxy groups are optionally substituted in one to three places, in the same way or differently, with radicals selected from the series halogen, cyano, hydroxy, (C$_1$-C$_4$)-alkoxy, amino, mono-(C$_1$-C$_4$)-alkylamino, di-(C$_1$-C$_4$)-alkylamino, (C$_3$-C$_7$)-cycloalkyl, and 4- to 7-membered heterocyclyl, and whereby pyridyl is optionally substituted with 1 or 2 substituents, whereby the substituents, independently of one another, are selected from: halogen, hydroxy, amino, cyano, nitro, (C$_1$-C$_4$)-alkyl, (C$_3$-C$_6$)-cycloalkyl, and (C$_1$-C$_4$)-alkoxy, and whereby the nitrogen atom of pyridyl can form an N-oxide in which the alkyl, cycloalkyl, and alkoxy groups are optionally substituted in one to three places, in the same way or differently, with radicals selected from: halogen, cyano, hydroxy, (C$_1$-C$_4$)-alkoxy, amino, mono-(C$_1$-C$_4$)-alkylamino, di-(C$_1$-C$_4$)-alkylamino, (C$_3$-C$_7$)-cycloalkyl, and 4- to 7-membered heterocyclyl, and A stands for imidazolidine-1-yl, morpholin-4-yl, thiomorpholin-4-yl, 1,3-thiazolidin-3-yl, piperidin-1-yl, piperazin-1-yl or 1,4-oxazepan-4-yl, each bonded via nitrogen, each of which is substituted with 1 to 3 substituents, whereby the substituents, independently of one another, are selected from: halogen, hydroxy, hydroxymethyl, formyl, amino, oxo, trifluoromethyl, trifluoromethoxy, (C$_1$-C$_4$)-alkyl, (C$_1$-C$_4$)-alkoxy, and (C$_1$-C$_4$)-alkoxycarbonyl, provided that there is at least one oxo substituent, whereby R$^2$ stands for pyridyl, when R$^1$ stands for phenyl, whereby R$^2$ stands for phenyl, when R$^1$ stands for pyridyl, and whereby when R$^1$ stands for 3-pyridyl, the latter cannot be substituted with unsubstituted alkoxy, or a salt, solvate or solvate of a salt thereof.

2. A compound according to claim 1, wherein:

R$^1$ stands for phenyl or pyridyl, whereby phenyl is substituted with 1 or 2 substituents, whereby the substituents, independently of one another, are selected from: halogen, amino, methyl, and trifluoromethyl, and whereby pyridyl is optionally substituted with 1 or 2 substituents, whereby the substituents, independently of one another, are selected from: halogen, amino, methyl, and trifluoromethyl, and whereby the nitrogen atom of the pyridyl optionally can form an N-oxide, R$^2$ stands for phenyl or pyridyl, whereby phenyl is substituted with 1 or 2 substituents, whereby the substituents, independently of one another, are selected from: halogen, cyano, (C$_1$-C$_4$)-alkyl, (C$_3$-C$_6$)-cycloalkyl, and (C$_1$-C$_4$)-alkoxy, in which the alkyl, cycloalkyl, and alkoxy groups are optionally substituted with 1 to 3 fluorine atoms, and whereby pyridyl is optionally substituted with 1 or 2 substituents, whereby the substituents, independently of one another, are selected from: halogen, cyano, (C$_1$-C$_4$)-alkyl, (C$_3$-C$_6$)-cycloalkyl, and (C$_1$-C$_4$)-alkoxy, and whereby the nitrogen atom of pyridyl optionally can form an N-oxide, in which the alkyl, cycloalkyl, and alkoxy groups are optionally substituted with 1 to 3 fluorine atoms, or a salt, solvate or solvate of a salt thereof.

3. A compound according to claim 1, wherein:

R$^1$ stands for pyridyl, whereby pyridyl is optionally substituted with 1 or 2 substituents, whereby the substituents, independently of one another, are selected from: halogen, amino, methyl, and trifluoromethyl, and whereby the nitrogen atom of pyridyl optionally can form an N-oxide, R$^2$ stands for phenyl, whereby phenyl is substituted with 1 to 2 substituents, whereby the substituents, independently of one another, are selected from: halogen, cyano, (C$_1$-C$_4$)-alkyl, (C$_3$-C$_6$)-cycloalkyl, and (C$_1$-C$_4$)-alkoxy, in which the alkyl, cycloalkyl, and alkoxy groups are optionally substituted with 1 to 3 fluorine atoms, and A stands for imidazolidine-1-yl, morpholin-4-yl, 1,3-thiazolidin-3-yl or piperazin-1-yl, each of which is substituted with 1 to 3 substituents, whereby the substituents, independently of one another, are selected from: hydroxy, amino, oxo, (C$_1$-C$_4$)-alkyl, and (C$_1$-C$_4$)-alkoxy, provided that there is at least one oxo substituent, or a salt, solvate or solvate of a salt thereof.

4. A compound according to claim 1, wherein:

R$^1$ stands for 3-pyridyl or 4-pyridyl, whereby pyridyl is optionally substituted with a halogen substituent, R$^2$ stands for phenyl, whereby phenyl is substituted with 1 or 2 substituents, whereby the substituents, independently of one another, are selected from: halogen, trifluoroalkoxy, and difluoroalkoxy, A stands for imidazolidine-1-yl, morpholin-4-yl, 1,3-thiazolidin-3-yl or piperazin-1-yl, each of which is substituted with 1 to 3 substituents, whereby the substituents, independently of one another, are selected from the group that consists of oxo and (C$_1$-C$_4$)-alkyl, provided that there is at least one oxo substituent, or a salt, solvate or solvate of a salt thereof.

5. A compound according to claim 1, wherein it corresponds to Formula (Ia):

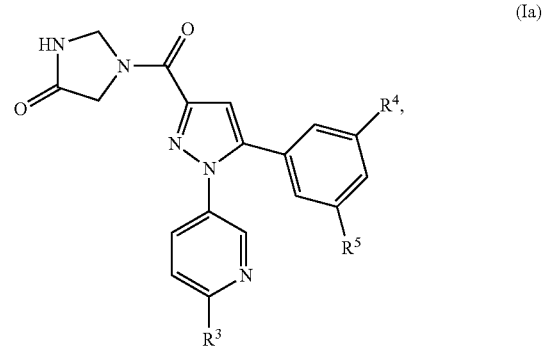

(Ia)

in which

R$^3$ stands for hydrogen, halogen, amino, trifluoromethyl or (C$_1$-C$_4$)-alkyl, R$^4$ stands for hydrogen, halogen, (C$_1$-C$_4$)-alkyl or (C$_1$-C$_4$)-alkoxy, in which alkyl and alkoxy can be substituted with 1 to 3 fluorine atoms, and $R^5$ stands for hydrogen, halogen, cyano, $(C_1-C_4)$-alkyl, $(C_3-C_6)$-cycloalkyl or $(C_1-C_4)$-alkoxy, whereby $R^4$ and $R^5$ cannot be hydrogen at the same time, or a salt, solvate or solvate of a salt thereof.

6. A compound according to claim 5, wherein:

$R^3$ stands for hydrogen or methyl, $R^4$ stands for fluorine, difluoromethoxy or trifluoromethoxy, and $R^5$ stands for fluorine, chlorine, bromine, or methoxy, or a salt, solvate or solvate of a salt thereof.

7. A compound according to claim 1, wherein it corresponds to Formula (Ib):

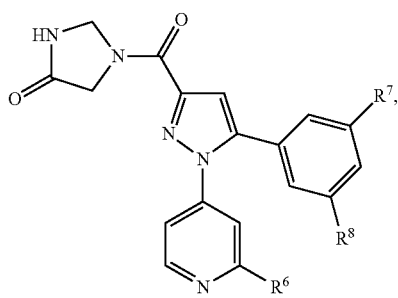

(Ib)

in which $R^6$ stands for hydrogen, halogen, trifluoromethyl, $(C_1-C_4)$-alkyl or $(C_1-C_4)$-alkoxy, $R^7$ stands for hydrogen, halogen, $(C_1-C_4)$-alkyl or $(C_1-C_4)$-alkoxy, in which alkyl and alkoxy are optionally substituted with 1 to 3 fluorine atoms, and $R^8$ stands for hydrogen, halogen, cyano, $(C_1-C_4)$-alkyl, $(C_3-C_6)$-cycloalkyl or $(C_1-C_4)$-alkoxy, whereby $R^7$ and $R^8$ cannot be hydrogen at the same time, or a salt, solvate or solvate of a salt thereof.

8. A compound according to claim 7, wherein:

$R^6$ stands for chlorine, trifluoromethyl, methyl, or methoxy, $R^7$ stands for fluorine, methoxy, difluoromethoxy, or trifluoromethoxy, and $R^8$ stands for fluorine, chlorine, bromine, or methoxy, or a salt, solvate or solvate of a salt thereof.

9. A compound according to claim 1, wherein it corresponds to Formula (Ic):

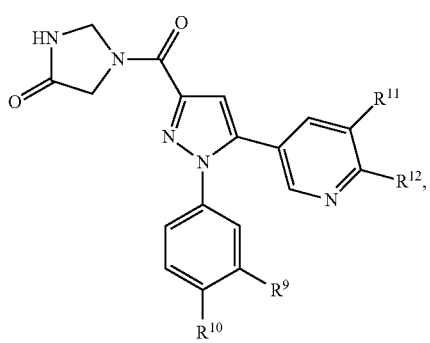

(Ic)

in which $R^9$ stands for hydrogen, halogen, cyano, $(C_1-C_4)$-alkyl or $(C_1-C_4)$-alkoxy, in which alkyl and alkoxy are optionally substituted with 1 to 3 fluorine atoms, $R^{10}$ stands for hydrogen, halogen, trifluoromethyl, $(C_1-C_4)$-alkyl or $(C_1-C_4)$-alkoxy, $R^{11}$ stands for hydrogen, halogen, cyano, $(C_1-C_4)$-alkyl or $(C_1-C_4)$-alkoxy, in which alkyl and alkoxy are optionally substituted with 1 to 3 fluorine atoms, and $R^{12}$ stands for hydrogen or halogen, whereby $R^9$ and $R^{10}$ cannot be hydrogen at the same time, or a salt, solvate or solvate of a salt thereof.

10. A compound according to claim 1, wherein it corresponds to Formula (Id):

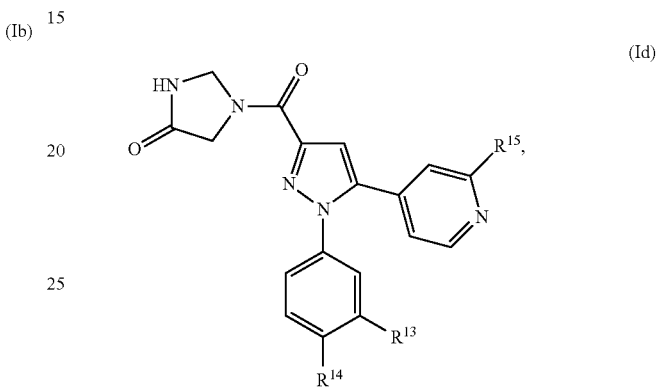

(Id)

in which $R^{13}$ stands for hydrogen, halogen, cyano, $(C_1-C_4)$-alkyl or $(C_1-C_4)$-alkoxy, in which alkyl and alkoxy are optionally substituted with 1 to 3 fluorine atoms, $R^{14}$ stands for hydrogen, halogen, trifluoromethyl, $(C_1-C_4)$-alkyl or $(C_1-C_4)$-alkoxy, and $R^{15}$ stands for hydrogen, halogen, cyano, $(C_1-C_4)$-alkyl or $(C_1-C_4)$-alkoxy, in which alkyl and alkoxy are optionally substituted with 1 to 3 fluorine atoms, whereby $R^{13}$ and $R^{14}$ cannot be hydrogen at the same time, or a salt, solvate or solvate of a salt thereof.

11. A method for the production of a compound of Formula (I) according to claim 1, which comprises reacting a compound of Formula (II):

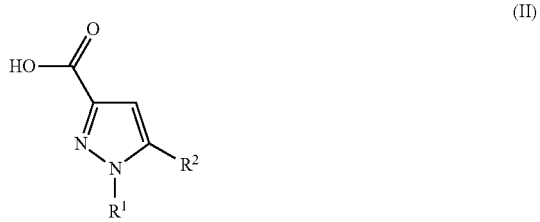

(II)

in which $R^1$ and $R^2$ have the above-indicated meaning, with a imidazolidine-1-yl, morpholin-4-yl, thiomorpholin-4-yl, 1,3-thiazolidin-3-yl, piperidin-1-yl, piperazin-1-yl or 1,4-oxazepan-4-yl compound as defined in claim 1 for A or a salt thereof.

12. A pharmaceutical composition which comprises at least one compound according to claim 1 in combination with at least one additional active ingredient.

13. A pharmaceutical composition which comprises at least one compound according to claim 1 in combination with at least one inert, non-toxic, pharmaceutically suitable adjuvant.

14. A method for treating a viral disease in a human or animal which comprises administering an antivirally effective amount of at least one compound according to claim 1 to a human or an animal suffering from said viral disease.

15. The method of claim 14, wherein the viral disease is a retrovirus.

* * * * *